United States Patent
Gertner et al.

(10) Patent No.: US 11,801,197 B2
(45) Date of Patent: *Oct. 31, 2023

(54) TREATMENT METHODS USING HANDHELD DEVICES FOR DISORDERS

(71) Applicant: Olympic Ophthalmics, Inc., Issaquah, WA (US)

(72) Inventors: Michael Gertner, Menlo Park, CA (US); Jimin Zhang, Bellevue, WA (US); Arash Sabet, Walnut Creek, CA (US)

(73) Assignee: Olympic Ophthalmics, Inc., Issaquah, WA (US)

( * ) Notice: Subject to any disclaimer, the term of this patent is extended or adjusted under 35 U.S.C. 154(b) by 65 days.

This patent is subject to a terminal disclaimer.

(21) Appl. No.: 17/450,493

(22) Filed: Oct. 11, 2021

(65) Prior Publication Data

US 2022/0023142 A1   Jan. 27, 2022

Related U.S. Application Data

(63) Continuation of application No. 16/057,787, filed on Aug. 7, 2018, now Pat. No. 11,141,348.
(Continued)

(51) Int. Cl.
*A61H 23/02* (2006.01)
*A61H 23/00* (2006.01)
(Continued)

(52) U.S. Cl.
CPC .......... *A61H 23/0263* (2013.01); *A61F 9/00* (2013.01); *A61H 23/006* (2013.01); *A61H 23/02* (2013.01);
(Continued)

(58) Field of Classification Search
CPC .... A61H 23/00; A61H 23/006; A61H 23/008; A61H 23/02; A61H 23/0236;
(Continued)

(56) References Cited

U.S. PATENT DOCUMENTS 2,809,631 A  10/1957 Smith et al.
3,075,527 A  1/1963 Bechtold
(Continued)

FOREIGN PATENT DOCUMENTS

CN  202015178  10/2011
CN  104837443  8/2015
(Continued)

OTHER PUBLICATIONS

Non-Final Office Action for U.S. Appl. No. 16/791,983 dated May 28, 2020.
(Continued)

*Primary Examiner* — Colin W Stuart
(74) *Attorney, Agent, or Firm* — Vista IP Law Group, LLP

(57) ABSTRACT

A method to treat a dry eye condition of an individual, includes: receiving a switch signal generated based on a manipulation of a control switch at a handheld device; and activating a motor in response to the switch signal to oscillate a member at an oscillation frequency, the member having an elongated configuration, and having a portion for placement outside the individual; wherein the oscillation frequency is sufficient to induce tear production when the portion of the member is applied towards a surface of a body portion of the individual.

52 Claims, 32 Drawing Sheets

Related U.S. Application Data

(60) Provisional application No. 62/659,582, filed on Apr. 20, 2018, provisional application No. 62/656,177, filed on Apr. 11, 2018, provisional application No. 62/635,471, filed on Feb. 26, 2018.

(51) Int. Cl.
*A61F 9/00* (2006.01)
*A61N 7/00* (2006.01)

(52) U.S. Cl.
CPC ...... *A61H 23/0218* (2013.01); *A61H 23/0236* (2013.01); *A61H 23/0245* (2013.01); *A61H 2201/0153* (2013.01); *A61H 2201/5025* (2013.01); *A61H 2201/5043* (2013.01); *A61H 2201/5061* (2013.01); *A61H 2201/5071* (2013.01); *A61H 2201/5076* (2013.01); *A61H 2201/5082* (2013.01); *A61H 2201/5084* (2013.01); *A61H 2201/5097* (2013.01); *A61H 2205/022* (2013.01); *A61H 2205/023* (2013.01); *A61H 2205/024* (2013.01); *A61N 7/00* (2013.01); *A61N 2007/0026* (2013.01)

(58) Field of Classification Search
CPC .............. A61H 23/004; A61H 23/0245; A61H 23/0254; A61H 23/0263; A61H 2023/0272; A61H 2023/029; A61H 2023/0281; A61H 2023/002; A61H 2201/0153; A61H 2201/0157; A61H 2201/0165; A61H 2201/12; A61H 2201/1215; A61H 2205/022; A61H 2205/024; A61H 2205/023
See application file for complete search history.

(56) References Cited

U.S. PATENT DOCUMENTS

| | | | |
|---|---|---|---|
| 3,672,355 A | 6/1972 | Ogawa et al. |
| 3,676,218 A | 7/1972 | Sawyer |
| 4,135,826 A | 1/1979 | Holm |
| 4,839,342 A | 1/1989 | Kaswan |
| 4,914,088 A | 4/1990 | Glonek et al. |
| 5,294,607 A | 3/1994 | Glonek et al. |
| 5,371,108 A | 12/1994 | Korb et al. |
| 5,578,586 A | 11/1996 | Glonek et al. |
| 5,925,002 A | 7/1999 | Wollman |
| 5,980,497 A | 11/1999 | Yavitz |
| 6,120,460 A | 9/2000 | Abreu |
| 6,152,916 A | 11/2000 | Bige |
| 6,254,562 B1 | 7/2001 | Fouere |
| 7,278,740 B1 | 10/2007 | Suzuki et al. |
| 7,976,573 B2 | 7/2011 | Korb et al. |
| 8,187,311 B2 | 5/2012 | Korb et al. |
| 8,403,954 B2 | 3/2013 | Santin et al. |
| 8,491,508 B2 | 7/2013 | Smith et al. |
| 8,676,324 B2 | 3/2014 | Simon et al. |
| 8,676,330 B2 | 3/2014 | Simon et al. |
| 8,764,688 B1 | 7/2014 | Nauman et al. |
| 8,996,137 B2 | 3/2015 | Ackermann et al. |
| 9,014,823 B2 | 4/2015 | Simon et al. |
| 9,020,598 B2 | 4/2015 | Simon et al. |
| 9,039,718 B2 | 5/2015 | Rynerson |
| 9,043,001 B2 | 5/2015 | Simon et al. |
| 9,233,246 B2 | 1/2016 | Simon et al. |
| 9,265,956 B2 | 2/2016 | Ackermann et al. |
| 9,440,065 B2 | 9/2016 | Ackermann et al. |
| 9,504,599 B2 | 11/2016 | Santin et al. |
| 9,510,972 B2 | 12/2016 | Badawi |
| 9,539,170 B1 | 1/2017 | Adaie |
| 9,579,247 B2 | 2/2017 | Juto et al. |
| 9,687,652 B2 | 6/2017 | Franke et al. |
| 9,717,627 B2 | 8/2017 | Kuzma et al. |
| 9,724,230 B2 | 8/2017 | Badawi |
| 9,737,702 B2 | 8/2017 | Ackermann et al. |
| 9,737,712 B2 | 8/2017 | Franke et al. |
| 9,764,150 B2 | 9/2017 | Loudin et al. |
| 9,770,583 B2 | 9/2017 | Gupta et al. |
| 9,782,320 B2 | 10/2017 | Juto et al. |
| 9,789,344 B2 | 10/2017 | Bujak et al. |
| 9,821,159 B2 | 11/2017 | Ackermann et al. |
| 9,844,459 B2 | 12/2017 | Badawi |
| 9,849,062 B2 | 12/2017 | Juto |
| 9,872,814 B2 | 1/2018 | Juto et al. |
| 9,956,397 B2 | 5/2018 | Loudin et al. |
| 10,022,511 B2 | 7/2018 | Avni |
| 10,045,907 B2 | 8/2018 | Harper et al. |
| 10,842,710 B2 | 11/2020 | Gertner et al. |
| 10,952,923 B2 | 3/2021 | Gertner et al. |
| 11,141,347 B2 | 10/2021 | Gertner et al. |
| 11,141,348 B2 * | 10/2021 | Gertner .................... A61F 9/00 |
| 2002/0049389 A1 | 4/2002 | Abreu |
| 2003/0108626 A1 | 6/2003 | Benita et al. |
| 2003/0143280 A1 | 7/2003 | El-Sherif et al. |
| 2003/0176898 A1 | 9/2003 | Gross et al. |
| 2003/0193644 A1 | 10/2003 | Schwebel |
| 2003/0233135 A1 | 12/2003 | Yee |
| 2004/0176749 A1 | 9/2004 | Lohmann et al. |
| 2004/0220644 A1 | 11/2004 | Shalev et al. |
| 2005/0022823 A1 | 2/2005 | Davison et al. |
| 2005/0054958 A1 | 3/2005 | Hoffmann |
| 2005/0075589 A1 | 4/2005 | Friedland |
| 2005/0119629 A1 | 6/2005 | Soroudi |
| 2006/0085027 A1 | 4/2006 | Santin et al. |
| 2006/0153885 A1 | 7/2006 | Korb et al. |
| 2007/0016254 A1 | 1/2007 | Grenon et al. |
| 2007/0060988 A1 | 3/2007 | Grenon et al. |
| 2007/0282405 A1 | 12/2007 | Wong, Jr. et al. |
| 2008/0081999 A1 | 4/2008 | Gravely et al. |
| 2008/0089480 A1 | 4/2008 | Gertner |
| 2008/0174733 A1 | 7/2008 | Chang et al. |
| 2008/0200848 A1 | 8/2008 | Avni |
| 2008/0249439 A1 | 10/2008 | Tracey et al. |
| 2008/0251085 A1 | 10/2008 | Schwebel |
| 2008/0269648 A1 | 10/2008 | Bock |
| 2009/0104248 A1 | 4/2009 | Rapacki et al. |
| 2009/0264861 A1 | 10/2009 | Jain et al. |
| 2009/0306577 A1 | 12/2009 | Akridge et al. |
| 2010/0092916 A1 | 4/2010 | Teixeira et al. |
| 2010/0106111 A1 | 4/2010 | Schwebel et al. |
| 2010/0189766 A1 | 7/2010 | Utkhede et al. |
| 2010/0274204 A1 | 10/2010 | Rapacki et al. |
| 2010/0292630 A1 | 11/2010 | Maskin |
| 2011/0087138 A1 | 4/2011 | Kahook |
| 2011/0190668 A1 | 8/2011 | Mishelevich |
| 2011/0196487 A1 | 8/2011 | Badawi et al. |
| 2011/0230701 A1 | 9/2011 | Simon et al. |
| 2011/0276107 A1 | 11/2011 | Simon et al. |
| 2011/0282251 A1 | 11/2011 | Baker et al. |
| 2011/0319794 A1 | 12/2011 | Gertner |
| 2012/0003296 A1 | 1/2012 | Shantha et al. |
| 2012/0016275 A1 | 1/2012 | Korb et al. |
| 2012/0016292 A1 | 1/2012 | Goldberg et al. |
| 2012/0065556 A1 | 3/2012 | Smith et al. |
| 2012/0130398 A1 | 5/2012 | Ackermann et al. |
| 2012/0157895 A1 | 6/2012 | Barlow et al. |
| 2012/0184801 A1 | 7/2012 | Simon et al. |
| 2012/0197176 A1 | 8/2012 | Badawi et al. |
| 2012/0213840 A1 | 8/2012 | Lim |
| 2012/0220905 A1 | 8/2012 | Avni |
| 2013/0006326 A1 | 1/2013 | Ackermann et al. |
| 2013/0158449 A1 | 6/2013 | Juto et al. |
| 2013/0158450 A1 | 6/2013 | Juto et al. |
| 2013/0158452 A1 | 6/2013 | Juto et al. |
| 2013/0172790 A1 | 7/2013 | Badawi |
| 2013/0172829 A1 | 7/2013 | Badawi |
| 2013/0253402 A1 | 9/2013 | Badawi et al. |
| 2013/0253403 A1 | 9/2013 | Badawi et al. |
| 2013/0253437 A1 | 9/2013 | Badawi et al. |
| 2013/0253438 A1 | 9/2013 | Badawi et al. |
| 2013/0274598 A1 | 10/2013 | Han |
| 2013/0296809 A1 | 11/2013 | Santin et al. |

(56) References Cited

U.S. PATENT DOCUMENTS

| | | |
|---|---|---|
| 2013/0331768 A1 | 12/2013 | Nichamin |
| 2013/0345808 A1 | 12/2013 | Badawi et al. |
| 2014/0031845 A1 | 1/2014 | Rynerson |
| 2014/0031866 A1 | 1/2014 | Fuhr et al. |
| 2014/0107397 A1 | 4/2014 | Simon et al. |
| 2014/0107398 A1 | 4/2014 | Simon et al. |
| 2014/0107444 A1 | 4/2014 | Liu |
| 2014/0121612 A1 | 5/2014 | Rubin et al. |
| 2014/0200425 A1 | 7/2014 | Etzkorn et al. |
| 2014/0207033 A1 | 7/2014 | Hillila |
| 2014/0213842 A1 | 7/2014 | Simon et al. |
| 2014/0257433 A1 | 9/2014 | Ackermann et al. |
| 2014/0277429 A1 | 9/2014 | Kuzma et al. |
| 2014/0316310 A1 | 10/2014 | Ackermann et al. |
| 2014/0316485 A1 | 10/2014 | Ackermann et al. |
| 2014/0323931 A1 | 10/2014 | Avni |
| 2014/0378878 A1 | 12/2014 | Sharma et al. |
| 2015/0012074 A1 | 1/2015 | Devine |
| 2015/0051699 A1 | 2/2015 | Badawi et al. |
| 2015/0073328 A1 | 3/2015 | Badawi et al. |
| 2015/0100001 A1 | 4/2015 | Bujak et al. |
| 2015/0119771 A1 | 4/2015 | Roberts |
| 2015/0141879 A1 | 5/2015 | Harper et al. |
| 2015/0148711 A1 | 5/2015 | Bujak et al. |
| 2015/0148774 A1 | 5/2015 | Yao |
| 2015/0157347 A1 | 6/2015 | Grenon et al. |
| 2015/0174425 A1 | 6/2015 | Toyos et al. |
| 2015/0164738 A1 | 7/2015 | Caropelo et al. |
| 2015/0182415 A1 | 7/2015 | Olkowski et al. |
| 2015/0238754 A1 | 8/2015 | Loudin et al. |
| 2015/0265830 A1 | 9/2015 | Simon et al. |
| 2015/0265836 A1 | 9/2015 | Simon et al. |
| 2015/0320590 A1 | 11/2015 | Whitehurst et al. |
| 2015/0320988 A1 | 11/2015 | Smith |
| 2016/0022992 A1 | 1/2016 | Franke et al. |
| 2016/0106576 A1 | 4/2016 | Badawi et al. |
| 2016/0121116 A1 | 5/2016 | Simon et al. |
| 2016/0121118 A1 | 5/2016 | Franke et al. |
| 2016/0158548 A1 | 6/2016 | Ackermann et al. |
| 2016/0361540 A9 | 12/2016 | Simon et al. |
| 2016/0367795 A1 | 12/2016 | Ackermann et al. |
| 2016/0367806 A1 | 12/2016 | Kahook |
| 2017/0007820 A9 | 1/2017 | Simon et al. |
| 2017/0014299 A1 | 1/2017 | Miller et al. |
| 2017/0071777 A1 | 3/2017 | Santin et al. |
| 2017/0079834 A1 | 3/2017 | Badawi |
| 2017/0079840 A1 | 3/2017 | Badawi |
| 2017/0087009 A1 | 3/2017 | Badawi et al. |
| 2017/0119311 A1 | 5/2017 | Iwasaki et al. |
| 2017/0128318 A1 | 5/2017 | Juto et al. |
| 2017/0165106 A1 | 6/2017 | Badawi |
| 2017/0181924 A1 | 6/2017 | Thorpe et al. |
| 2017/0239459 A1 | 8/2017 | Loudin et al. |
| 2017/0252563 A1 | 9/2017 | Franke et al. |
| 2017/0304110 A1 | 10/2017 | Badawi |
| 2017/0304145 A1 | 10/2017 | Pepe |
| 2017/0340884 A1 | 11/2017 | Franke et al. |
| 2018/0000499 A1 | 1/2018 | Altman et al. |
| 2018/0064942 A1 | 3/2018 | Franke et al. |
| 2018/0104514 A1 | 4/2018 | Gertner et al. |
| 2018/0133098 A1 | 5/2018 | Juto |
| 2018/0133100 A1 | 5/2018 | Park |
| 2018/0133507 A1 | 5/2018 | Malchano et al. |
| 2018/0161579 A1 | 6/2018 | Franke et al. |
| 2019/0070069 A1 | 3/2019 | Gertner et al. |
| 2019/0151604 A1 | 5/2019 | Harper et al. |

FOREIGN PATENT DOCUMENTS

| | | |
|---|---|---|
| EP | 1915186 | 12/2011 |
| JP | 2015077204 A | 4/2015 |
| WO | WO 2006129305 | 12/2006 |
| WO | WO 2006129305 A2 | 12/2006 |
| WO | WO 2006129305 A3 | 12/2006 |
| WO | WO 2013003594 | 1/2013 |
| WO | WO 2013003594 A2 | 1/2013 |
| WO | WO 2013003594 A3 | 1/2013 |
| WO | WO 2014/172693 | 10/2014 |
| WO | WO 2018071839 | 4/2018 |
| WO | WO 2018071839 A1 | 4/2018 |

OTHER PUBLICATIONS

Amendment Response to NFOA for U.S. Appl. No. 16/791,983 dated Jul. 27, 2020.
Notice of Allowance for U.S. Appl. No. 16/791,983 dated Oct. 19, 2020.
Dartt, DA., Neural regulation of lacrimal gland secretory processes: relevance in dry eye diseases. Prog Retin Eye Res. May 2009;28(3): 155-77. doi: 10.1016/j.preteyeres.2009.04.003. Epub Apr. 17, 2009.
Han, et al. Anatomy of the External Nasal Nerve. Plastic and Reconstructive Surgery: Oct. 2004—vol. 114—Issue 5—p. 1055-1059.
Levi; et al., "Levi, et al., Stimulation of the Sphenopalatine Ganglion Induces Reperfusion and Blood-Brain Barrier Protection in the Photothrombotic Stroke Model. Plos One, Jun. 22, 2012;".
PCT/US2017/056624 International Search Report and Written Opinion dated Mar. 8, 2018.
Reher, et al., Ultrasound stimulates nitric oxide and prostaglandin E2 production by human osteoblasts. Bone. Jul. 2002;31 (1):236-41.
Supplemental Search Report EP17861134 dated Feb. 7, 2020.
Sheppard et al. "Characterization of tear production in subjects with dry eye disease during intranasal tear neurostimulation: Results from two pivotal clinical trials." The Ocular Surface 17 (2019), pp. 142-150. (Year: 2019).
Non-Final Office Action for U.S. Appl. No. 16/250,571 dated Jan. 16, 2020.
Amendment Response to NFOA for U.S. Appl. No. 16/250,571 dated Sep. 17, 2019.
Non-Final Office Action for U.S. Appl. No. 16/250,571 dated Aug. 20, 2019.
Notice of Allowance for U.S. Appl. No. 16/250,571 dated Feb. 16, 2021.
Notice of Allowance for U.S. Appl. No. 16/802,346 dated Jun. 16, 2021.
Amendment Response to NFOA for U.S. Appl. No. 16/802,346 dated Jun. 3, 2021.
Non-Final Office Action for U.S. Appl. No. 16/802,346 dated Apr. 27, 2021.
Final Office Action for U.S. Appl. No. 16/802,346 dated Jan. 1, 2021.
Amendment Response to NFOA for U.S. Appl. No. 16/802,346 dated Sep. 14, 2020.
Non-Final Office Action for U.S. Appl. No. 16/802,346 dated Jun. 17, 2020.
Notice of Allowance for U.S. Appl. No. 16/057,790 dated Dec. 15, 2021.
Dartt, Darlene A. "Neural regulation of lacrimal gland secretory processes: relevance in dry eye diseases." Progress in retinal and eye research 28.3 (2009): 155-177.
Prendergast, Peter M. "Neurologic anatomy of the nose." Advanced Aesthetic Rhinoplasty. Springer, Berlin, Heidelberg, 2013. 17-23.
Han, Seung-Kyu, Young-Won Shin, and Woo-Kyung Kim. "Anatomy of the external nasal nerve." Plastic and reconstructive surgery 114.5 (2004): 1055-1059.
Extended European Search Report dated Feb. 7, 2020 for EP Appln. No. 17861134.9.
Non-Final Office Action for U.S. Appl. No. 16/057,785 dated Dec. 22, 2020.
Amendment Response to NFOA for U.S. Appl. No. 16/057,785 dated May 24, 2021.
Non-Final Office Action for U.S. Appl. No. 16/057,786 dated Dec. 24, 2021.
Amendment Response to NFOA for U.S. Appl. No. 16/057,786 dated May 24, 2021.
Non-Final Office Action for U.S. Appl. No. 16/057,788 dated Dec. 23, 2020.

(56) References Cited

OTHER PUBLICATIONS

Non-Final Office Action for U.S. Appl. No. 16/057,790 dated Jan. 21, 2021.
Amendment Response to NFOA for U.S. Appl. No. 16/057,790 dated May 21, 2021.
PCT International Search Report and Written Opinion for International Appln. No. PCT/US2019/019600, Applicant Olympic Ophthalmics, Inc., dated Jun. 28, 2019 (41 pages).
Amendment Response to NFOA for U.S. Appl. No. 16/250,571 dated Nov. 24, 2020.
PCT International Search Report and Written Opinion for International Appln. No. PCT/US17/56624 dated Mar. 8, 2018 (5 pages).
Levi; et ai, "Stimulation of the Sphenopalatine Ganglion Induces Reperfusion and Blood-Brain Barrier Protection in the Photothrombotic Stroke Model". Plos One, Jun. 22, 2012.
Non-Final Office Action for U.S. Appl. No. 16/057,789 dated Apr. 7, 2022.

\* cited by examiner

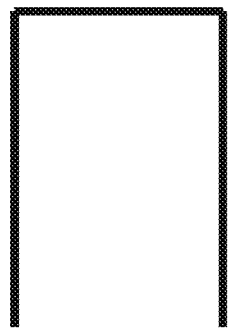
FIG. 29A  FIG. 29B
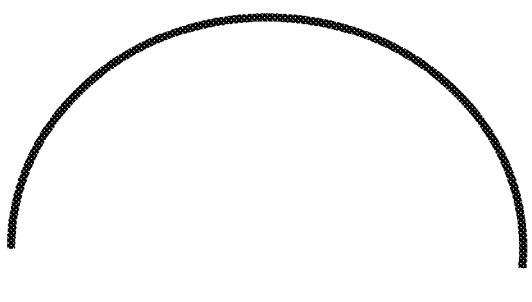
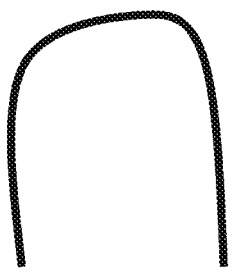
FIG. 30A  FIG. 30B

TREATMENT METHODS USING HANDHELD DEVICES FOR DISORDERS

CROSS-REFERENCE TO RELATED APPLICATIONS

This application is a continuation of U.S. patent application Ser. No. 16/057,787 filed on Aug. 7, 2018, pending, which claims priority to, and the benefit of, U.S. Provisional Patent Application No. 62/635,471 filed Feb. 26, 2018, lapsed, U.S. Provisional Patent Application No. 62/656,177 filed Apr. 11, 2018, lapsed, and U.S. Provisional Patent Application No. 62/659,582 filed Apr. 18, 2018, lapsed. The entire disclosures of the above applications are expressly incorporated by reference herein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

TECHNICAL FIELD

The present disclosure relates generally to medical devices and methods. More particularly, the present disclosure relates to devices and methods for stimulating or inhibiting nerves and/or treating conditions, such as congestion, keratoconjunctivitis sicca, sinusitis, carpal tunnel syndrome, eye conditions, a skin condition, acne, cysts, or any other condition.

BACKGROUND

New methods and devices for treating different medical conditions are described herein. One or more embodiments described herein utilize mechanical vibration (such as therapeutic sound, ultrasound, mechanical perturbation, etc.) in the treatment of one or more conditions, such as congestion, sinusitis, and/or dry eye.

SUMMARY

In an exemplary first aspect, the present disclosure provides a method for stimulating tear production in a patient. The method comprises positioning a vibratory surface at a bony region on the patient's face communicating with a parasympathetic nerve which innervates the lacrimal gland. The vibratory surface is vibrated at a frequency and a displacement selected to stimulate the lacrimal nerve to produce tears. Typically, the vibratory surface will stimulate an afferent nerve which communicates with a parasympathetic nerve which stimulates glands related to the tear film.

The vibratory surface may be vibrated at any frequency effective to stimulate the target nerves, typically being in a range from 10 Hz to 1000 Hz, 10 Hz to 500 Hz, 10 Hz to 400 Hz, 10 Hz to 300 Hz, 10 Hz to 200 Hz, 10 Hz to 100 Hz, 10 Hz to 50 Hz, 50 Hz to 1000 Hz, 50 Hz to 500 Hz, 50 Hz to 400 Hz, 50 Hz to 300 Hz, 50 Hz to 200 Hz, 50 Hz to 100 Hz, 200 Hz to 1000 Hz, 200 Hz to 500 Hz, 200 Hz to 400 Hz, 200 Hz to 300 Hz, 300 Hz to 1000 Hz, 300 Hz to 500 Hz, 300 Hz to 400 Hz, or 400 Hz to 1000. Similarly, the vibratory surface may be vibrated at any displacement effective to stimulate the target nerves, typically being in a range from 0.1 mm to 5 mm, 0.25 mm to 5 mm, 0.5 mm to 5 mm, 1 mm to 5 mm, 0.1 mm to 3 mm, 0.25 mm to 3 mm, 0.5 mm to 3 mm, 1 mm to 3 mm, 0.1 mm to 5 mm, 0.25 mm to 2 mm, 0.5 mm to 2 mm, 1 mm to 2 mm, or 2 mm to 3 mm.

The vibratory surface typically has a skin contact area in a range from 0.5 $mm^2$ to 20 $mm^2$, 0.5 $mm^2$ to 10 $mm^2$, 0.5 $mm^2$ to 5 $mm^2$, 0.5 $mm^2$ to 2 $mm^2$, 0.5 $mm^2$ to 1.5 $mm^2$, 0.5 $mm^2$ to 1 $mm^2$, 1 $mm^2$ to 20 $mm^2$, 1 $mm^2$ to 10 $mm^2$, 1 $mm^2$ to 5 $mm^2$, 1 $mm^2$ to 2 $mm^2$, 1 $mm^2$ to 1.5 $mm^2$, 1.5 $mm^2$ to 20 $mm^2$, 0.5 $mm^2$ to 10 $mm^2$, 1.5 $mm^2$ to 5 $mm^2$, 1.5 $mm^2$ to 2 $mm^2$, 2 $mm^2$ to 20 $mm^2$, 2 $mm^2$ to 10 $mm^2$, 2 $mm^2$ to 5 $mm^2$, 2.5 $mm^2$ to 20 $mm^2$, 2.5 $mm^2$ to 10 $mm^2$, 2.5 $mm^2$ to 5 $mm^2$, 5 $mm^2$ to 20 $mm^2$, or 5 $mm^2$ to 10 $mm^2$.

The vibratory surface typically has a hardness in a range from Shore A40 to Shore A80, Shore A50 to Shore A80, Shore A60 to Shore A80, Shore A70 to Shore A80, Shore A40 to Shore A70, Shore A50 to Shore A70, Shore A60 to Shore A70, Shore A40 to Shore A60, Shore A50 to Shore A60, or Shore A40 to Shore A50.

The vibratory surface is usually formed on a polymeric interface body and may have a thickness in a range from 1 mm to 10 mm, 2 mm to 10 mm, 3 mm to 10 mm, 4 mm to 01 mm, 5 mm to 10 mm, 6 mm to 10 mm, 7 mm to 10 mm, 8 mm to 10 mm, 9 mm to 10 mm, 1 mm to 5 mm, 2 mm to 5 mm, 3 mm to 5 mm, 4 mm to 5 mm, 1 mm to 4 mm, 2 mm to 4 mm, 3 mm to 4 mm, 1 mm to 3 mm, 2 mm to 3 mm, or 1 mm to 2 mm.

In some embodiments, the vibratory surface may be positioned on the patient's face at a location where the patient's upper lateral nasal cartilage meets the patient's nasal bone. In such cases, the vibratory surface may be engaged against the patient's face with an upward directionality.

In some embodiments, the vibratory surface may be positioned at a location from 6.5 mm to 8.5 mm lateral to the patient's nasal midline at the region.

In some embodiments, the vibratory surface may be positioned proximate or over the parasympathetic nerve which innervates the lacrimal gland and travels through the sphenopalatine ganglia located close to the maxillary bone in the sphenopalatine fossa.

In some embodiments, the vibratory surface may be positioned by engaging the vibratory surface on a handheld device against the bony region. Usually, a patient engages the vibratory surface of the handheld device against the bony region.

In some embodiments, the vibratory surface moves in a substantially linear direction in one dimension. For example, the vibratory surface may be driven in a substantially linear direction with an excursion of 0.5 to 2 mm.

In some embodiments, the vibratory surface may be placed in a position to stimulate the external nasal nerve.

In an exemplary second aspect, the present disclosure provides a handheld device for stimulating tear production in a patient. The device comprises a housing having a vibratory surface configured to engage a bony region on the patient's face over an afferent nerve which communicates with a parasympathetic nerve which innervates glands related to the tear film. Circuitry within the housing is configured to vibrate the vibratory surface at a frequency and a displacement selected to stimulate the afferent nerve, the lacrimal nerve to produce tears, goblet cells to secrete mucin, and the Meibomian glands to produce oils to maintain the tear film.

Exemplary frequencies, displacements, skin contact areas for the vibratory surfaces, and other design features of the vibratory surfaces and devices have been set forth above with respect to the first exemplary aspects of the present disclosure.

In other aspects of the methods and handheld device of the present disclosure, the device circuitry may be configured to vibrate vibratory surface with a pulsed duty cycle of 90%, 75%, 50%, 25%, or 10%. In specific embodiments, the circuitry may be configured to increase a peak displacement of the vibratory surface when the duty cycle is less than 100%.

The handheld device may be configured to be positioned by the patient so that the vibratory surface engages the vibratory surface against the bony region.

The circuitry may be configured to allow adjustment of the vibrational frequency. For example, the handheld device may include a manual frequency adjustment interface.

The vibrational transducer of the handheld device is typically at least one ultrasonic vibrational transducer, usually operating at a frequency in a range from 20 kHz to 30 MHz or from 3 MHz and 10 MHz. The hand held device may further comprise at least one non-ultrasonic vibrational transducer, typically operating at a frequency in a range from 10 Hz to 1000 Hz, 10 Hz to 500 Hz, 10 Hz to 400 Hz, 10 Hz to 300 Hz, 10 Hz to 200 Hz, 10 Hz to 100 Hz, 10 Hz to 50 Hz, 50 Hz to 1000 Hz, 50 Hz to 500 Hz, 50 Hz to 400 Hz, 50 Hz to 300 Hz, 50 Hz to 200 Hz, 50 Hz to 100 Hz, 200 Hz to 1000 Hz, 200 Hz to 500 Hz, 200 Hz to 400 Hz, 200 Hz to 300 Hz, 300 Hz to 1000 Hz, 300 Hz to 500 Hz, 300 Hz to 400 Hz, or 400 Hz to 1000 Hz.

In some embodiments, therapeutic sound or ultrasound or mechanical vibrations is utilized to treat dry eye by stimulating the lacrimal glands or the nasolacrimal duct.

In some embodiments, therapeutic ultrasound is utilized to stimulate nerves which travel to the lacrimal gland in the eye.

In some embodiments, therapeutic ultrasound is utilized to open up Meibomian glands inside an eyelid.

In some embodiments, therapeutic ultrasound or sound is utilized to stimulate a lacrimal duct via the nose in a patient.

In some embodiments, therapeutic sound or ultrasound is utilized to stimulate secretion of tears.

In some embodiments, therapeutic sound, ultrasound, or mechanical vibration is utilized to stimulate the external branch of the anterior ethmoidal nerve (external nasal nerve) to create tears or decongest the sinus or nasal cavities.

In some embodiments, therapeutic sound is coupled to skin covering bony structures and a frequency of sound is applied to the skin such that the bone underneath resonates in response to the sound and the resonation through the bone activates nerves in close proximity to the bone.

In some embodiments, therapeutic sound is delivered through end effectors which propagate the sound and transduce it to the bony structures of the head and neck with optimal safety and effectiveness.

In some embodiments, therapeutic sound is used to stimulate the sphenopalatine ganglia and associated nerves in the pterygopalatine fossa by transducing sound through the skin overlying the maxillary bone.

In some embodiments, therapeutic sound, vibration, or ultrasound is utilized to stimulate the external branch of the anterior ethmoidal nerve (external nasal nerve) at the region of the nose where the nasal bone meets the lateral process of the septal nasal cartilage.

In some embodiments, therapeutic sound or ultrasound is utilized to stimulate the sphenopalatine ganglia to treat cold symptoms such as stuffed or congested nasal passageways.

In some embodiments, therapeutic sound, vibration, or ultrasound is utilized to inhibit the sphenopalatine ganglia.

In some embodiments, external ultrasound and/or mechanical vibration are applied to the region where the nasal bone meets the nasal cartilage to stimulate the nerves related to the sphenopalatine ganglia or the ethmoidal nerves to increase tears and treat dry eye.

In some embodiments, external ultrasound and/or mechanical vibration are applied to the region where the nasal bone meets the nasal cartilage to stimulate the external nasal nerve to treat congestion, sinusitis, or a combination thereof.

In some embodiments, external ultrasound and/or mechanical vibration are applied to a region adjacent to or on top of the median nerve, for example on a ventral side of a wrist of an individual, to treat carpal tunnel syndrome.

In some embodiments, external ultrasound and/or mechanical vibration are applied to a skin surface to treat any skin condition, for example psoriasis, acne, aging, cysts (e.g., sebaceous cysts), eczema, rosacea, seborrheic dermatitis, hemangiomas, cold sores, warts, cutaneous Candidiasis, carbuncles, cellulitis, hypohidrosis, impetigo, canker sores, Herpes infections, seborrheic keratosis, actinic keratosis (i.e., age spots), corns, calluses, mouth ulcers, or any other skin condition known in the art.

For example, external ultrasound and/or mechanical vibration are applied to a skin surface to unplug follicles, for example plugged with accumulations of dead skin from the lining of the pore, to treat and/or prevent acne. Additionally or alternatively, external ultrasound and/or mechanical vibration are applied to disrupt acne forming bacteria, for example *Propionibacterium acnes*, in pores. Such bacteria accumulate in pores plugged or clogged with dead skin cells and/or accumulated sebum.

For example, external ultrasound and/or mechanical vibration are applied to a skin surface to unplug or inhibit sebaceous glands, for example that become plugged at the base of pores or that over-produce sebum, to treat and/or prevent acne.

For example, external ultrasound and/or mechanical vibration are applied to a skin surface to inhibit inflammation generated by the immune system which can cause redness, irritation, and swelling.

For example, external ultrasound and/or mechanical vibration are applied to a skin surface to induce firmness, collagen formation, and/or fibroblastic activity to increase skin youthfulness and reduce aging and wrinkles.

For example, external ultrasound and/or mechanical vibration are applied to a skin region adjacent to or on top of a cyst to disrupt the cyst and induce healing.

One aspect of the present disclosure relates to a method to treat a nerve of the facial region. In some embodiments, the method includes: applying a handheld device with an applicator tip to the skin of a face of a patient, the skin covering a facial bony region immediately thereunder; depressing the applicatory tip on the skin toward the bone of the face of the patient such that further depression is prevented; and delivering vibratory energy from the handheld device, through the applicator tip of the device, through the skin of the patient and through the bone of the patient to stimulate or inhibit a nerve of the head and neck region of the patient.

In some embodiments, the vibratory energy has a frequency from about 50 Hz to about 1 KHz. In some embodiments, the vibratory energy has a frequency from about 100 Hz to about 500 Hz.

In some embodiments, the handheld device is applied to the side of a nose of patient and depressed against the nasal bone along the side of the nose at the region where the cartilage meets the bone to stimulate tears in the patient. In some embodiments, the handheld device is applied to the side of a nose of the patient at the location where the nasal cartilage and the nasal bone meet. In some embodiments, the handheld device is depressed along the side of the nose at the location where the nasal cartilage and the nasal bone meet; and, applying a finger to the contralateral side of the nose concomitantly. In some embodiments, the handheld device is applied to both sides of the nose of the patient either simultaneously or sequentially during therapy.

In some embodiments, the handheld device delivers vibratory energy at a decibel (db) level less than about 20 db. In some embodiments, the handheld device delivers the vibratory energy at a decibel level less than about 10 db.

In some embodiments, the method includes stimulating a nerve of the head and neck region to create tearing from the eye. In some embodiments, the method includes stimulating a sphenopalatine ganglia of the patient to generate tears from the lacrimal gland of the patient. In some embodiments, the method includes stimulating the nasolacrimal duct to generate tears in the eye of the patient.

In some embodiments, the vibratory frequency is adjusted to optimize the stimulation or inhibition of the nerve. In some embodiments, the vibratory amplitude is adjusted to optimize the stimulation or inhibition of the nerve.

In some embodiments, the method includes attaching the applicator tip to a finger tip and pressing the fingertip to the skin of the nose in the region where the nasal bone meets the nasal cartilage. In some embodiments, the method includes attaching the applicator tip to two fingers; and, applying the vibratory energy to the bone by pinching the region of the nose with the two fingers.

In some embodiments, the method includes holding the applicator to one side of the nose with a first hand while adjusting its pressure on the skin by pressing against the other side of the nose with a different finger of the same hand. In some embodiments, the method includes one of: adjusting the angle of application, the pressure against the skin, and the type of applicator tip based on feedback from the patient of a sensation of tearing.

In some embodiments, the method includes touching the applicator tip to a region of the face to affect a change in a congestion condition such as one of: sinusitis, nasal congestion, and rhinitis.

Another aspect of the present disclosure is directed to a device to stimulate a nerve in the head and neck region of a patient. In some embodiments, the device includes: an applicator with a connected applicator handle, an actuator coupled to the handheld applicator, and a body surface interface mechanically coupled to the actuator, such that the actuator moves mechanically at a frequency driven by an electric current and voltage to generate vibrational energy, and the body surface interface is adapted to couple to a skin interface of the head and neck region of the patient to transmit vibrational energy to a bone through the skin, and to stimulate a nerve acoustically coupled to the bone through the skin.

In some embodiments, the actuator vibrates at a frequency of between 100 and 300 Hz. In some embodiments, the actuator is coupled to a material such that the material moves with a planar excursion of about 500 microns and not more than about 1500 microns.

In some embodiments, the body surface interface is adapted to couple to a nasal bridge. In some embodiments, the body surface interface is adapted to simultaneously couple to both sides of a nose. In some embodiments, the body surface interface has the compliance of a pencil eraser.

In some embodiments, the handheld applicator is adapted to be worn on a wrist and the actuator is separated from the handheld actuator by a flexible wire. In some embodiments, the handheld applicator further includes a portable battery.

In some embodiments, the nerve is part of, or communicates with, a sphenopalatine ganglia. In some embodiments, the vibrational energy is configured to resonate with the bone overlying the nerve to stimulate the nerve. In some embodiments, the skin surface interface is adapted to be grasped between the fingers of the patient. In some embodiments, the skin surface interface is connected to a pair of spectacles. In some embodiments, the skin surface interface further includes a combination of a rigid material and a malleable material. In some embodiments, the skin surface interface further is adapted to direct the vibrational energy preferentially in one direction to couple the vibrational energy to the bone underlying the skin and the handheld applicator is isolated from the movement and vibration.

In some embodiments, the nerve is a branch of facial nerve. In some embodiments, the nerve is a lacrimal nerve.

In some embodiments, the device includes an adjustment control to vary the vibration frequency and/or the amplitude of the actuator. In some embodiments, the applicator is handheld. In some embodiments, the applicator is configured to be attached to a finger. In some embodiments, the applicator is configured to be attached to two fingers such that the bridge of the nose can be pinched with two actuators to transmit vibration to the nerve of the head or neck region simultaneously. In some embodiments, the applicator is configured to be attached to the wrist of the patient. In some embodiments, the applicator is configured to be attached to a pair of spectacles. In some embodiments, the applicator is configured to be applied to an eyelid appliance.

In some embodiments, the body surface interface is adapted to couple vibrations from the actuator to the bone underneath the skin. In some embodiments, the body surface interface comprises a semi-rigid material. In some embodiments, the body surface interface is adapted to couple to the finger of a user and wherein the body surface interface further includes a second interface which couples to a second finger of a user. In some embodiments, the body surface interface includes or is formed of a shape memory material to facilitate form fitting to the tissue of the outer region of a nose of a user.

In some embodiments, the device includes a controller which enables modulation of the amplitude of the vibration of the body surface interface.

In some embodiments, the vibrational energy is adapted to activate a pressure sensitive nerve. In some embodiments, the actuator imparts motion to the body surface interface in which the motion is linear and is adapted to apply to the skin surface so that the motion is approximately perpendicular to the skin surface. In some embodiments, the actuator imparts motion to the body surface interface in which the motion is linear and is adapted to apply to the skin surface so that the motion is perpendicular to the skin surface and can be adjusted so that the motion is applicable at an angle to the skin surface. In some embodiments, the actuator imparts motion to the body surface interface in which the motion is linear and is adapted to apply to the skin surface while vibrations to the hand of the user are minimized. In some embodiments, the actuator is electrically connected to a controller in which the controller imparts an adjustable frequency control. In some embodiments, the actuator is electrically connected to a controller in which the controller imparts an adjustable amplitude control. In some embodiments, the actuator is a solenoid with an electromagnet to impart linear direction to the body surface interface. In some embodiments, the actuator is a speaker or a voice activated coil. In some embodiments, the actuator has a linear actuator component such that vibrations are isolated from the user of the device.

In some embodiments, the body surface interface is rigid with an edge of approximately 1-2 mm width and configured to fit in the ridge at the junction of the nasal bone and nasal cartilage. In some embodiments, the body surface interface further includes an edge adapted to at least partially retract an eyelid.

In some embodiments, the actuator is connected to cam, and the cam drives a piston to create a linear motion.

In some embodiments, the cam is attached to a rod which connects to a position offset from the central axis of the motor so as to create a linear motion of the piston, the excursion of which is proportional to the offset from the central axis. In some embodiments, the offset results in a 1 mm excursion of the piston. In some embodiments, the offset results in a 2 mm excursion of the piston. In some embodiments, the offset results in a 0.5 mm excursion of the piston.

In some embodiments, the device includes an electronic control circuit, such that the electronic control circuit outputs a programmable voltage which determines the revolutions per minute of the motor and therefore the excursion frequency of the piston. In some embodiments, the linear motion applicator is adapted to apply a force of about 1 N to 5 N to a region of the face overlying a nerve to activate the nerve with periodic application of this force through the skin to reach the nerve underlying the skin to create a clinical effect in a patient.

In some embodiments, the method includes: placing the handheld device on the region along the skin along the side of the nose where the nasal bone and the nasal cartilage meet; firmly pressing into this region; and, applying vibratory energy from the handheld device with a frequency of about 100-300 Hz and an excursion of the device tip of about 0.5 mm to about 1.5 mm.

In some embodiments, the method includes targeting the anterior ethmoidal nerve.

In some embodiments, the method includes: setting the handheld device to generate ultrasound pressure waves with frequency of about 500 kHz to about 5 MHz.

In some embodiments, the method includes activating the anterior ethmoidal nerve.

In some embodiments, the method includes applying pressure to the handheld device along the skin of the patient so that the patient feels a sneezing or tearing sensation. In some embodiments, the method includes applying a range of frequencies of pressure waves to determine the optimal frequency and degree of pressure to achieve the effect of sneezing or tear production.

In some embodiments, a sphenopalatine ganglia is activated by applying the handheld device to the external nasal nerve.

Another aspect of the present disclosure is directed to a method to treat a nerve of the facial region. In some embodiments, the method includes: applying a handheld device with an applicator tip to the skin of a face of a patient, the skin covering a bony region of the face; depressing the applicator tip on the skin toward the bone of the face of the patient; and delivering vibratory energy from the handheld device, through the applicator tip of the device, through the skin of the patient and through the bone of the patient to create a biologic effect in a mucosal region underlying the bone.

In some embodiments, the method includes: delivering the vibratory energy via applicator tip with a frequency of approximately 100-300 Hz and an excursion of 0.5 m to 2.0 mm. In some embodiments, the method includes: delivering vibratory energy via applicator tip with a frequency of approximately 300 Hz to 50 kHz. In some embodiments, the method includes: delivering vibratory energy via applicator tip with a frequency of approximately 50 kHz to 10 MHz.

Another aspect of the present disclosure is directed to a method to treat a nerve of the facial region. In some embodiments, the method includes: applying a handheld device with an applicator tip to the skin of a face of a patient, the skin covering a bony region of the face, the bony region coupled to an autonomic nerve; depressing the application tip on the skin toward the bone of the face of the patient; and delivering vibratory energy from the handheld device, through the applicator tip of the device, through the skin of the patient and through the bone of the patient to create a biologic effect in a mucosal region underlying the bone.

In some embodiments, the mucosal region is a sinus cavity or a nasal passage.

In some embodiments, the vibratory energy has a frequency of between 50 Hz and 5 MHz.

In some embodiments, the method includes: cycling the vibratory power with a duty cycle, a peak power, and/or an average power.

In some embodiments, the method includes performing a surgical procedure prior to, during or after delivery of the vibrational energy. In some embodiments, the method includes locating a sinus or a region of congestion using an acoustic impulse. In some embodiments, the method includes: simultaneously utilizing multiple vibratory frequencies.

In some embodiments, the method includes: applying one vibratory energy with a frequency between 50 and 300 Hz and a second vibratory energy of between about 1 MHz and 30 MHz.

In some embodiments, the method includes: mapping the nerve anatomy of the nasal region prior to applying the vibratory energy.

In some embodiments, the method includes: activating the activator tip to deliver vibratory energy with a frequency between 1 MHz and 10 MHz. In some embodiments, the method includes: activating the activator tip to deliver vibratory energy with a frequency between 0.5 MHz and 5 MHz. In some embodiments, the method includes: activating the activator tip to deliver a vibratory energy with a frequency between 50 Hz and 500 Hz.

In some embodiments, the method includes: stimulating a parasympathetic nerve to create a tearing response.

Another aspect of the present disclosure is directed to a method to treat patient with dry eye. In some embodiments, the method includes: applying a handheld device with an applicator tip to the skin of a face of a patient, the skin covering a bony region of the face; depressing the applicator tip on the skin toward the bone of the face of the patient in the region where the nasal cartilage meets the nasal bone; and delivering vibratory energy from the handheld device with a frequency between 100 Hz and 400 Hz and an amplitude of the applicator tip greater than 500 microns to the region where the nasal cartilage meets the nasal bone to stimulate tears in the eyes of the patient.

In some embodiments, the method includes: setting the frequency to a frequency between 150 and 200 Hz.

Another aspect of the present disclosure is directed to a method to treat a patient with nasal or sinus disease. In some embodiments, the method includes: applying a sound or ultrasound applicator to the skin surrounding the nasal sinuses; setting an amplitude and a frequency of the applicator applied to the skin; and delivering sound or ultrasound energy from the applicator to the skin of the patient and through the skin of the patient to the nasal or sinus mucosa of the patient.

In some embodiments, the disease is an allergic disease and the sound or ultrasound overstimulates the nerves to inhibit their function in the allergic disease.

In some embodiments, the method includes delivering the sound or ultrasound prior to, during, or after balloon sinuplasty. In some embodiments, the sound or ultrasound comprises frequency between 50 Hz and 300 Hz. In some embodiments, the method includes delivering sound or ultrasound just prior to, during, or after a functional endoscopic sinus surgery procedure (FESS). In some embodiments, the sound and ultrasound are delivered to the region of the external nasal nerve at the junction of the nasal cartilage and nasal bone.

Another aspect of the present disclosure is directed to a method of creating tears in a patient. In some embodiments, the method includes: gripping a device with one hand and applying it to provide for vibration at 100 to 300 Hz with an approximately linear excursion of the tip of the device of about 500 to 1500 microns; applying the device to the region of the external part of the nose where the nasal cartilage meets the nasal bone; and activating the external nasal nerve.

In some embodiments, the method includes applying a force of about 0.5 N to about 3.0 N to the external nasal nerve. In some embodiments, the method includes applying a force of about 0.5 N to about 5.0 N.

Another aspect of the present disclosure is directed to a method to treat dry eye. In some embodiments, the method includes: applying a vibrating implement to a region proximate an eyelid or nose of a patient; determining a set of test vibration parameters of the implement; determining a location and optimal range of vibration frequency and amplitude of the implement based on patient and operator feedback; and setting the vibration frequency and amplitude of the implement based on the patient and/or operator feedback.

In some embodiments, the implement further comprises ultrasound with frequency between 1 MHz and 30 MHz and the optimal frequency is determined by the patient/user.

In some embodiments, the location is set to the region where the nasal bone meets the nasal cartilage.

In some embodiments, the user further depresses the skin on the side of the face opposite the side where the implement is being applied.

In some embodiments, the user depresses the skin on the nose on the side opposite the placement of the implement and depresses the implement simultaneously to transmit vibrations and activate nerves on both sides of the face.

In some embodiments, the location is proximate an infraorbital nerve. In some embodiments, the location is proximate to a sphenopalatine ganglia. In some embodiments, the location is proximate an ethmoidal nerve. In some embodiments, the location is a lacrimal gland. In some embodiments, the location is an accessory lacrimal gland. In some embodiments, the location is the skin of the eyelid and the amplitude and frequency are chosen to eliminate wrinkles in the eyelid.

In some embodiments, the vibration frequency is chosen from a frequency between 50 Hz and 300 Hz; and the amplitude is chosen from about 0.1 mm to about 1.5 mm; and wherein the amplitude is sinusoidal; and wherein the implement moves with a substantially linear motion.

Another aspect of the present disclosure is directed to a method to generate tears in a human subject. In some embodiments, the method includes: applying an applicator to an external region of a nose of a subject, the region located where the external branch of the anterior ethmoidal nerve exits to the skin alongside the nose; and activating the applicator to generate mechanical vibration at a frequency of between 100 and 300 Hz, the vibration generating a force on the skin and underlying nerve sufficient to activate the nerve.

In some embodiments, the method includes: actively mapping nerves in the skin distributions on the face of a subject to determine the optimum location for stimulation of the exterior anterior ethmoidal nerve. In some embodiments, the active mapping includes stimulating the nerves in the skin distributions on the face of the subject with a range of frequencies of between 50 Hz and 300 Hz, a range of amplitudes between 0.5 mm and 3.0 mm and a range of forces between 0.5 N and 3 N. In some embodiments, the active mapping further includes monitoring the effect of the stimulation of the nerves.

In some embodiments, the active mapping includes monitoring one of: tearing, sneezing, blood flow, nasal mucosa fullness, and itching.

In some embodiments, the method includes determining one of: optimum frequency, position, force, amplitude, duration, power, and duty cycle. In some embodiments, the method includes: positioning the applicator specifically along the mapped regions.

Another aspect of the present disclosure is directed to a method to generate tears in a human subject. In some embodiments, the method includes: applying an applicator to an external region of a nose of a subject, the region located where the external branch of the anterior ethmoidal nerve exits to the skin alongside the nose; activating the applicator to generate mechanical vibration at a frequency of between 50 Hz and 300 Hz; and applying a force over an area of about 1 $mm^2$ to about 5 $mm^2$ on the skin and underlying nerve of approximately 0.5 N to about 2 N to activate the nerve.

Another aspect of the present disclosure is directed to device configured to activate tears in a human patient. In some embodiments, the device includes: an end effector configured to interface with the external skin over the region of the nose where the external nasal nerve exits the nasal bone; a main body configured to be handheld; and an actuation mechanism coupled to the end effector and configured to produce mechanical vibration of the end effector.

In some embodiments, the end effector is configured to apply 0.5 N to 3.0 N force over an area of about 1 $mm^2$ to about 5 $mm^2$. In some embodiments, the end effector includes an edge radius of curvature of 0.5 mm to 2.0 mm. In some embodiments, the end effector includes a notch to fit in the region of the interface of the nasal cartilage and nasal bone. In some embodiments, the end effector further includes or is formed of a biocompatible material with a durometer between 20 A and 60 A. In some embodiments, the end effector is actuated to move a distance of between 5 mm and 30 mm. In some embodiments, the end effector is actuated to move a distance of between 5 mm and 30 mm while maintaining relatively constant force of between 0.5 N and 3.0 N.

In some embodiments, the actuator includes a linear resonance actuator. In some embodiments, the actuator includes an eccentrically weighted motor. In some embodiments, the actuator includes a voice coil. In some embodiments, the actuator comprises an electromagnet. In some embodiments, the actuator includes a piezoelectric crystal.

In some embodiments, the actuator is configured to accelerate the end effector with a linear motion. In some embodiments, the actuator is configured to accelerate the end effector in a circular motion. In some embodiments, the actuator is configured to accelerate the end effector in a sinusoidal pattern. In some embodiments, the actuator is configured to accelerate the end effector in a programmable pattern. In some embodiments, the actuator is configured to accelerate the end effector in a pattern which is programmable with a smart phone application.

Another aspect of the present disclosure is directed to a method for treating rhinitis. In some embodiments, the method includes: delivering a vibratory stimulus via a probe to treat rhinitis in a patient in need thereof, such that the probe is in contact with one or more tissues of the nose of the patient during delivery of the vibratory stimulus.

In some embodiments, the electrical stimulus is delivered in response to one or more symptoms of rhinitis. In some embodiments, the one or more symptoms of rhinitis include one or more of itching, sneezing, congestion, runny nose, post-nasal drip, mouth breathing, coughing, fatigue, headache, anosmia, phlegm, throat irritation, periorbital puffiness, watery eyes, ear pain, and fullness sensation.

In some embodiments, the vibratory stimulus is delivered more than once per day on a scheduled basis.

In some embodiments, the one or more tissues of the nose is the nasal mucosa. In some embodiments, the one or more tissues of the nose is skin on the outside of the nose. In some embodiments, the one or more nasal tissues is the mucosa adjacent to the nasal septum.

In some embodiments, the vibratory stimulus is a linear motion with an oscillation frequency of about 100 to 300 Hz.

Another aspect of the present disclosure is directed to a method of treating rhinitis. In some embodiments, the method includes: delivering a vibratory stimulus to a nasal tissue of a subject to improve rhinitis of the subject, such that the vibratory stimulus is delivered via a probe comprising a control subsystem to control the vibratory stimulus.

In some embodiments, the vibratory stimulus is delivered in response to one or more symptoms of rhinitis. In some embodiments, the one or more symptoms of rhinitis comprise one or more of itching, sneezing, congestion, runny nose, post-nasal drip, mouth breathing, coughing, fatigue, headache, anosmia, phlegm, throat irritation, periorbital puffiness, watery eyes, ear pain, and fullness sensation.

In some embodiments, the vibratory stimulus is delivered at least once daily during a treatment period. In some embodiments, the vibratory stimulus is delivered on a scheduled basis during the treatment period.

Another aspect of the present disclosure is directed to a method for treating ocular allergy. In some embodiments, the method includes: delivering a vibratory stimulus via probe to treat ocular allergy in a patient in need thereof, wherein the probe is in contact with nasal tissue of the patient during delivery of the vibratory stimulus.

In some embodiments, the vibratory stimulus is delivered in response to one or more symptoms of ocular allergy.

In some embodiments, the one or more symptoms of ocular allergy comprise one or more of swelling, puffiness, itching, tearing, and discharge.

In some embodiments, the nasal tissue is nasal mucosa. In some embodiments, the nasal tissue is the external skin of the nose.

In some embodiments, the vibratory stimulus is a linear motion at approximately 100 Hz to 300 Hz.

Another aspect of the present disclosure is directed to a method of treating ocular allergy, including: delivering a vibratory stimulus to a nasal tissue of a subject to improve ocular allergy of the subject, such that the vibratory stimulus is delivered by a probe of a stimulator comprising a control subsystem to control the vibratory stimulus.

In some embodiments, the electrical stimulus is delivered in response to one or more symptoms of ocular allergy. In some embodiments, the one or more symptoms of ocular allergy comprise one or more of swelling, puffiness, itching, tearing, and discharge.

Another aspect of the present disclosure is directed to a method to treat sinusitis. In some embodiments, the method includes: positioning a vibratory surface at a bony region on the patient's face communicating with a parasympathetic nerve; and vibrating the vibratory surface at a frequency and a displacement selected to stimulate the external nasal nerve.

Another aspect of the present disclosure is directed to a method to treat rhinitis. In some embodiments, the method includes: positioning a vibratory surface at a bony region on the patient's face communicating with a parasympathetic nerve; and vibrating the vibratory surface at a frequency and a displacement selected to stimulate the external nasal nerve.

Another aspect of the present disclosure is directed to a handheld device for applying ultrasound or mechanical vibration to a body portion of an individual to treat a condition of the individual. In some embodiments, the device includes: an effector tip configured to oscillate in substantially one dimension; a motor in contact with the effector tip, such that the motor induces the substantially one-dimensional oscillation of the effector tip; and a power source electrically coupled to the motor. In some embodiments, the effector tip is formed of a material that has a durometer sufficient to induce therapeutic effects without abrading the body portion of the individual.

In some embodiments, the effector tip is part of a cantilevered beam and the motor induces reciprocal motion in the cantilevered beam to induce effector tip oscillation. In some embodiments, the cantilevered beam bends when a force is applied to the effector tip, wherein bending the cantilevered beam slows the motor, reduces effector tip oscillation, and unbalances the motor oscillation so that the end effector moves in a preferential direction.

In some embodiments, the device further includes a housing, such that the cantilevered beam is coupled to the housing via a coupling element, and a natural frequency of a combination of the cantilevered beam and the coupling element match an oscillation frequency of the motor. In some embodiments, the coupling element is a bracket or joint.

In some embodiments, the cantilevered beam includes a characteristic height dimension, width dimension, and length dimension.

In some embodiments, a frequency of oscillation of the effector tip is dampable when a force of substantially 1 N is applied to the effector tip.

In some embodiments, the device further includes a housing, such that the power source and motor are housed in the housing and the effector tip at least partially protrudes from the housing.

In some embodiments, the device further includes a port configured to receive an adapter therein for charging the power source. In some embodiments, the power source is a rechargeable battery.

In some embodiments, the effector tip oscillates with a substantially fixed amplitude in air. In some embodiments, the substantially fixed amplitude is between about 0.25 mm and 1.5 mm.

In some embodiments, the amplitude of oscillation is dampable when a force of substantially 2 N is applied to the effector tip.

In some embodiments, the durometer is between 40 A to 60 A.

In some embodiments, the effector tip oscillates with a force of 1 N to 3 N.

In some embodiments, a frequency of oscillation of the effector tip is 50 Hz to 300 Hz.

In some embodiments, the condition is one or more of: congestion, keratoconjunctivitis sicca, sinusitis, carpal tunnel syndrome, a skin condition, acne, and cysts.

In some embodiments, the device further includes a storage medium configured to store information related to one or more of: a treatment duration, a treatment start time, a treatment end time, applied force against skin, and a treatment frequency.

In some embodiments, the device further includes a housing and a retractor coupled to the housing, such that the retractor is configured to retract an eyelid of the individual so that effector tip oscillation is applied to an eye structure. In some embodiments, the eye structure is one or more of: an eyelid, an eyeball, and a structure in or around an eye.

In some embodiments, the therapeutic effect is stimulation of a nerve, wherein the nerve is one of: an external nasal nerve, a media nerve, an optic nerve, a lacrimal nerve, and a parasympathetic nerve.

In some embodiments, the body portion is one of: an eye structure, a wrist, a nose region, and a facial region.

In some embodiments, the substantially one-dimensional oscillation of the effector tip is perpendicular to the body portion. In some embodiments, a subset of the oscillations of the effector tip is parallel to the body portion. In some embodiments, for every four perpendicular oscillations there is one parallel oscillation.

Another aspect of the present disclosure is related to an apparatus for quantifying one or more of: a motion, a frequency, and a force of an oscillating device. In some embodiments, the apparatus includes: a sensor coupled to one or more members, such that the sensor is configured to measure the force exerted by the oscillating device in at least on direction; a processor electrically coupled to the sensor, such that the processor is configured to collect one or more readings from the sensor; and a holder configured to position the oscillating device in contact with the sensor.

In some embodiments, the one or more sensor readings collected by the processor are transmitted (e.g., via BlueTooth, RF, NFC, wireless protocol, etc.) to an electronic device communicatively coupled to the apparatus.

In some embodiments, the apparatus further includes a frame, such that the one or more members are also coupled to the frame and are configured to suspend the sensor in the frame.

In some embodiments, the one or more readings are collected at greater than 200 Hz. In some embodiments, the one or more readings are collected at 3.95 kHz. In some embodiments, the one or more readings are collected at greater than 1 kHz.

In some embodiments, the apparatus is configured to estimate a force output of the oscillating device in at least one direction when the oscillating device is pre-loaded in the one or more members and allowed to reach equilibrium with the one or more members prior to the sensor being turned on.

In some embodiments, the apparatus further includes a plate, such that the sensor is coupled to the plate which is coupled to the one or more members.

In some embodiments, the one or more members are stretchable or elastic.

In some embodiments, the sensor is an accelerometer.

In some embodiments, the oscillating device includes an oscillating effector tip, such that the oscillating effector tip is positioned in contact with the sensor.

A handheld device for applying mechanical vibration to a body portion of an individual to treat a dry eye condition of the individual, includes: a housing; a member having a first portion accommodated in the housing, and a second portion that is moveable relative to the housing, wherein the second portion is for placement outside the individual, and is configured to oscillate to apply the mechanical vibration to the body portion, the member having an elongated configuration; and a motor in the housing, the motor configured to oscillate the member at an oscillation frequency sufficient to induce tear production when the second portion of the member is applied towards a surface of the body portion.

Optionally, the motor is configured to cause the member to undergo bending action in a reciprocating manner.

Optionally, the motor is carried by the member.

Optionally, the motor is fixedly attached to the member so that the motor and the member can move together.

Optionally, the member comprises a cantilevered beam having a free end, the second portion being at the free end of the cantilevered beam.

Optionally, the motor is configured to cause the cantilevered beam to undergo bending action in a reciprocating manner.

Optionally, a speed of the motor is variable based on an amount of force applied at the second portion of the member.

Optionally, the oscillation frequency of the member is variable based on an amount of force applied at the second portion of the member.

Optionally, the first portion of the member is fixedly coupled to the housing via a coupling element, and wherein a natural frequency of a combination of the member and the coupling element corresponds with an oscillation frequency of the motor.

Optionally, the coupling element comprises a bracket or joint.

Optionally, an oscillation of the second portion is dampable when a force of 1 N is applied to the second portion of the member.

Optionally, the handheld device further includes a power source accommodated in the housing.

Optionally, the handheld device further includes a port configured to receive an adapter for charging the power source.

Optionally, the power source is a rechargeable battery.

Optionally, the second portion of the member is configured to oscillate with a substantially fixed amplitude in air.

Optionally, the substantially fixed amplitude is anywhere between 0.25 mm and 1.5 mm.

Optionally, an oscillation of the second portion is dampable when a force of 2 N is applied to the second portion of the member.

Optionally, the second portion of the member has a durometer that is anywhere between 40 A to 60 A.

Optionally, the second portion of the member is configured to oscillate with a force that is anywhere from 1 N to 3 N.

Optionally, the oscillation frequency of the member is anywhere from 50 Hz to 300 Hz.

Optionally, the handheld device further includes a storage medium configured to store information related to a treatment duration, a treatment start time, a treatment end time, an applied force, a treatment frequency, or any combination of the foregoing.

Optionally, the motor is configured to oscillate the member at the oscillation frequency to stimulate a nasal nerve to induce the tear production.

Optionally, the body portion comprises a nose region, and the second portion of the member is configured to apply the mechanical vibration to the nose region.

Optionally, the body portion comprises a facial region, and the second portion of the member is configured to apply the mechanical vibration to the facial region.

Optionally, the second portion of the member is configured for placement over an infraorbital nerve.

Optionally, the second portion of the member is configured for placement over an anterior ethmoidal nerve.

Optionally, the second portion of the member is configured for placement over an external nasal nerve.

Optionally, the second portion of the member is configured for placement over an eyelid or on a sclera of an eye.

Optionally, the second portion of the member is configured for placement along a sensory portion of an ophthalmic nerve division of a trigeminal nerve.

Optionally, the second portion of the member is configured to apply a vibrational force having a first directional component that is perpendicular to a surface of the body portion.

Optionally, the vibrational force has a second directional component that is parallel to the surface of the body portion.

Optionally, a first frequency of the first directional component is higher than a second frequency of the second directional component.

Optionally, the second portion has a curvilinear surface for contacting the body portion.

Optionally, the second portion has a convex exterior surface.

Optionally, the handheld device further includes a power switch operable by the individual to activate the handheld device.

Optionally, the power switch comprises a button, wherein the handheld device is configured to be activated in response to a pressing of the button, and is configured to be deactivated when the button is un-pressed.

Optionally, the second portion of the member is outside the housing.

Optionally, the housing comprises an opening, and the second portion of the member is configured to oscillate within the opening.

Optionally, the second portion has a thickness measured in a direction that is parallel to a skin against which the second portion is to be applied, the thickness being between 0.5 mm and 3 mm.

Optionally, the second portion has a tissue-contacting surface, a side wall, and a dull corner between the tissue-contacting surface and the side wall.

A handheld device for applying mechanical vibration to a body portion of an individual to treat a dry eye condition of the individual, includes: a housing; a member having a first portion accommodated in the housing, and a second portion that is moveable relative to the housing, wherein the second portion is for placement outside the individual, and is configured to oscillate to apply the mechanical vibration to the body portion; and a motor in the housing, the motor configured to cause the member to undergo bending action in a reciprocating manner to oscillate the second portion of the member at an oscillation frequency sufficient to induce tear production when the second portion of the member is applied towards a surface of the body portion.

Optionally, the motor is carried by the member.

Optionally, the motor is fixedly attached to the member so that the motor and the member can move together.

Optionally, the member comprises a cantilevered beam having a free end, the second portion being at the free end of the cantilevered beam.

Optionally, a speed of the motor is variable based on an amount of force applied at the second portion of the member.

Optionally, the oscillation frequency of the member is variable based on an amount of force applied at the second portion of the member.

Optionally, the first portion of the member is fixedly coupled to the housing via a coupling element, and wherein a natural frequency of a combination of the member and the coupling element corresponds with an oscillation frequency of the motor.

Optionally, the coupling element comprises a bracket or joint.

Optionally, an oscillation of the second portion is dampable when a force of 1 N is applied to the second portion of the member.

Optionally, the handheld device further includes a power source accommodated in the housing.

Optionally, the handheld device further includes a port configured to receive an adapter for charging the power source.

Optionally, the power source is a rechargeable battery.

Optionally, the second portion of the member is configured to oscillate with a substantially fixed amplitude in air.

Optionally, the substantially fixed amplitude is anywhere between 0.25 mm and 1.5 mm.

Optionally, an oscillation of the second portion is dampable when a force of 2 N is applied to the second portion of the member.

Optionally, the second portion of the member has a durometer that is anywhere between 40 A to 60 A.

Optionally, the second portion of the member is configured to oscillate with a force that is anywhere from 1 N to 3 N.

Optionally, the oscillation frequency of the member is anywhere from 50 Hz to 300 Hz.

Optionally, the handheld device further includes a storage medium configured to store information related to a treatment duration, a treatment start time, a treatment end time, an applied force, a treatment frequency, or any combination of the foregoing.

Optionally, the motor is configured to oscillate the member at the oscillation frequency to stimulate a nasal nerve to induce the tear production.

Optionally, the body portion comprises a nose region, and the second portion of the member is configured to apply the mechanical vibration to the nose region.

Optionally, the body portion comprises a facial region, and the second portion of the member is configured to apply the mechanical vibration to the facial region.

Optionally, the second portion of the member is configured for placement over an infraorbital nerve.

Optionally, the second portion of the member is configured for placement over an anterior ethmoidal nerve.

Optionally, the second portion of the member is configured for placement over an external nasal nerve.

Optionally, the second portion of the member is configured for placement over a nasociliary nerve.

Optionally, the second portion of the member is configured for placement over an eyelid or on a sclera of an eye.

Optionally, the second portion of the member is configured for placement along a sensory portion of an ophthalmic nerve division of a trigeminal nerve.

Optionally, the second portion of the member is configured to apply a vibrational force having a first directional component that is perpendicular to a surface of the body portion.

Optionally, the vibrational force has a second directional component that is parallel to the surface of the body portion.

Optionally, a first frequency of the first directional component is higher than a second frequency of the second directional component.

Optionally, the second portion has a curvilinear surface for contacting the body portion.

Optionally, the second portion has a convex exterior surface.

Optionally, the handheld device further includes a power switch operable by the individual to activate the handheld device.

Optionally, the power switch comprises a button, wherein the handheld device is configured to be activated in response to a pressing of the button, and is configured to be de-activated when the button is un-pressed.

Optionally, the second portion of the member is outside the housing.

Optionally, the housing comprises an opening, and the second portion of the member is configured to oscillate within the opening.

Optionally, the second portion has a thickness measured in a direction that is parallel to a skin against which the second portion is to be applied, the thickness being between 0.5 mm and 3 mm.

Optionally, the second portion has a tissue-contacting surface, a side wall, and a dull corner between the tissue-contacting surface and the side wall.

A method to treat a dry eye condition of an individual, includes: receiving a switch signal generated based on a manipulation of a control switch at a handheld device; and activating a motor in response to the switch signal to oscillate a member at an oscillation frequency, the member having an elongated configuration, and having a portion for placement outside the individual; wherein the oscillation frequency is sufficient to induce tear production when the portion of the member is applied towards a surface of a body portion of the individual.

Optionally, the motor is activated to cause the member to undergo bending action in a reciprocating manner.

Optionally, the member comprises a cantilevered beam having a free end, the portion being at the free end of the cantilevered beam.

Optionally, the motor is activated to cause the cantilevered beam to undergo bending action in a reciprocating manner.

Optionally, the method further includes varying a speed of the motor in response to an amount of force received at the portion of the member.

Optionally, the method further includes varying the oscillation frequency of the member in response to an amount of force received at the portion of the member.

Optionally, the method further includes receiving power from a power source located in a housing of the handheld device.

Optionally, the power source is a rechargeable battery.

Optionally, the portion of the member oscillates with a substantially fixed amplitude in air.

Optionally, the substantially fixed amplitude is anywhere between 0.25 mm and 1.5 mm.

Optionally, the portion of the member has a durometer that is anywhere between 40 A to 60 A.

Optionally, the portion of the member oscillates with a force that is anywhere from 1 N to 3 N.

Optionally, the oscillation frequency of the member is anywhere from 50 Hz to 300 Hz.

Optionally, the method further includes storing information related to a treatment duration, a treatment start time, a treatment end time, an applied force, a treatment frequency, or any combination of the foregoing.

Optionally, the motor oscillates the member at the oscillation frequency to stimulate a nasal nerve to induce the tear production.

Optionally, the body portion comprises a nose region.

Optionally, the body portion comprises a facial region.

Optionally, the portion of the member is configured for placement over an infraorbital nerve.

Optionally, the portion of the member is configured for placement over an anterior ethmoidal nerve.

Optionally, the portion of the member is configured for placement over an external nasal nerve.

Optionally, the portion has a curvilinear surface for contacting the body portion.

Optionally, the portion has a convex exterior surface.

Optionally, the control switch comprises a button, wherein the switch signal is generated in response to a pressing of the button, and wherein the method further comprises de-activating the handheld device when the button is un-pressed.

Optionally, the portion of the member oscillates outside a housing of the handheld device.

Optionally, the handheld device has a housing with an opening, and the portion of the member oscillates within the opening.

A method to treat a dry eye condition of an individual, includes: receiving a switch signal generated based on a manipulation of a control switch at a handheld device; and activating a motor in response to the switch signal to cause a member to undergo bending action in a reciprocating manner to oscillate a portion of the member at an oscillation frequency, the member having a portion for placement outside the individual; wherein the oscillation frequency is sufficient to induce tear production when the portion of the member is applied toward a surface of a body portion of the individual.

Optionally, the portion of the member is moveable into a housing in response to a force applied to the portion of the member.

Optionally, the member comprises a cantilevered beam having a free end, the portion being at the free end of the cantilevered beam.

Optionally, the member comprises a cantilevered beam having a fixed end, wherein the fixed end affects an oscillation property of the cantilevered beam.

Optionally, the method further includes varying a speed of the motor in response to an amount of force received at the portion of the member.

Optionally, the method further includes varying the oscillation frequency of the member in response to an amount of force received at the portion of the member.

Optionally, the method further includes receiving power from a power source located in a housing of the handheld device.

Optionally, the power source is a rechargeable battery.

Optionally, the portion of the member oscillates with a substantially fixed amplitude in air.

Optionally, the substantially fixed amplitude is anywhere between 0.25 mm and 1.5 mm.

Optionally, the portion of the member has a durometer that is anywhere between 40 A to 60 A.

Optionally, the portion of the member oscillates with a force that is anywhere from 1 N to 3 N.

Optionally, the oscillation frequency of the member is anywhere from 50 Hz to 300 Hz.

Optionally, the method further includes storing information related to a treatment duration, a treatment start time, a treatment end time, an applied force, a treatment frequency, or any combination of the foregoing.

Optionally, the motor oscillates the member at the oscillation frequency to stimulate a nasal nerve to induce the tear production.

Optionally, the body portion comprises a nose region.

Optionally, the body portion comprises a facial region.

Optionally, the portion of the member is configured for placement over an infraorbital nerve.

Optionally, the portion of the member is configured for placement over an eyelid or directly on a sclera of an eye.

Optionally, the portion of the member is configured to be inserted intra-nasally.

Optionally, the portion of the member is configured for placement along a distribution of a sensory portion of an ophthalmic nerve division of a trigeminal nerve.

Optionally, the portion of the member is configured for placement over an anterior ethmoidal nerve.

Optionally, the portion has a curvilinear surface for contacting the body portion.

Optionally, the portion has a convex exterior surface.

Optionally, the portion has a thickness that is anywhere from 0.5 mm to 3 mm, and an edge forming an angle that is anywhere from 65 degrees to 125 degrees.

Optionally, the control switch comprises a button, wherein the switch signal is generated in response to a pressing of the button, and wherein the method further comprises de-activating the handheld device when the button is un-pressed.

Optionally, the portion of the member oscillates outside a housing of the handheld device.

Optionally, the handheld device has a housing with an opening, and the portion of the member oscillates within the opening.

A handheld device for applying mechanical vibration to a body portion of an individual to treat a condition of the individual, includes: a housing; a member having a portion that is moveable relative to the housing, wherein the portion of the member is configured to oscillate to apply the mechanical vibration to the body portion, the member having an elongated configuration; and a motor having a weight that is supported by the member.

Optionally, the motor is fixedly attached to the member.

Optionally, the motor has a motor housing, and the motor housing is attached to the member.

Optionally, the motor comprises a shaft, and the handheld device further comprises an eccentric mass secured to a shaft of the motor.

Optionally, the motor and the portion of the member are configured to move together.

Optionally, the handheld device further includes an electrical wire connected to the motor, wherein at least a portion of the electrical wire is coupled to the member.

Optionally, the member has a first bending stiffness in a first bending direction, and a second bending stiffness in a second bending direction, the second bending stiffness being higher than the first bending stiffness.

Optionally, the first bending direction corresponds with a direction of oscillation by the portion of the member.

Optionally, the member has a cross section with a first side and a second side, the first side being longer than the second side, and wherein the motor is attached to the first side.

Optionally, the motor configured to oscillate the member at an oscillation frequency sufficient to induce tear production or a sinus effect when the portion of the member is applied towards a surface of the body portion.

Optionally, the motor is configured to cause the member to undergo bending action in a reciprocating manner.

Optionally, the member comprises a cantilevered beam having a free end, the portion of the member being at the free end of the cantilevered beam.

Optionally, the motor is configured to cause the cantilevered beam to undergo bending action in a reciprocating manner.

Optionally, the handheld device further includes a power source accommodated in the housing.

Optionally, the portion of the member is configured to oscillate with an amplitude that is anywhere between 0.25 mm and 1.5 mm.

Optionally, the portion of the member has a durometer that is anywhere between 40 A to 60 A.

Optionally, the portion of the member is configured to oscillate with a force that is anywhere from 1 N to 3 N.

Optionally, an oscillation frequency of the member is anywhere from 50 Hz to 300 Hz.

Optionally, the handheld device further includes a storage medium configured to store information related to a treatment duration, a treatment start time, a treatment end time, an applied force, a treatment frequency, or any combination of the foregoing.

Optionally, the motor is configured to oscillate the member at an oscillation frequency sufficient to stimulate a nasal nerve to induce the tear production.

Optionally, the body portion comprises a nose region, and the portion of the member is configured to apply the mechanical vibration to the nose region.

Optionally, the body portion comprises a facial region, and the portion of the member is configured to apply the mechanical vibration to the facial region.

Optionally, the portion of the member is configured for placement over an infraorbital nerve.

Optionally, the portion of the member is configured for placement over an anterior ethmoidal nerve.

Optionally, the portion of the member is configured for placement over an external nasal nerve.

Optionally, the portion of the member is configured for placement over an eyelid or on a sclera of an eye.

Optionally, the portion of the member is configured for placement along a sensory portion of an ophthalmic nerve division of a trigeminal nerve.

Optionally, the portion of the member is configured for placement inside a nasal opening.

Optionally, the portion of the member is configured to apply a vibrational force having a first directional component that is perpendicular to a surface of the body portion.

Optionally, the vibrational force has a second directional component that is parallel to the surface of the body portion.

Optionally, the portion of the member has a curvilinear surface for contacting the body portion.

Optionally, the portion of the member has a convex exterior surface.

Optionally, the handheld device further includes a power switch operable by the individual to activate the handheld device.

Optionally, the power switch comprises a button, wherein the handheld device is configured to be activated in response to a pressing of the button, and is configured to be de-activated when the button is un-pressed.

Optionally, the portion of the member is outside the housing.

Optionally, the housing comprises an opening, and the portion of the member is configured to oscillate within the opening.

Optionally, the portion of the member has a thickness measured in a direction that is parallel to a skin against which the portion of the member is to be applied, the thickness being between 0.5 mm and 3 mm.

Optionally, the portion of the member has a tissue-contacting surface, a side wall, and a dull corner between the tissue-contacting surface and the side wall.

A handheld device for applying mechanical vibration to a body portion of an individual to treat a condition of the individual, includes: a housing; a member having a portion that is moveable relative to the housing, wherein the portion of the member is configured to oscillate to apply the mechanical vibration to the body portion, the member having an elongated configuration; and a motor having a motor housing that is fixed in position with respect to the member, and wherein the motor and the member are configured to move relative to the housing together as one unit.

A handheld device for applying mechanical vibration to a body portion of an individual to treat a condition of the individual, includes: a housing; a member having a portion that is moveable relative to the housing, wherein the portion of the member is configured to oscillate to apply the mechanical vibration to the body portion, the member having an elongated configuration; and a motor carried by the member.

A handheld device for applying mechanical vibration to a body portion of an individual to treat a condition of the individual, includes: a housing; a member having an exterior surface for contacting the individual, the member configured to oscillate to apply the mechanical vibration to the body portion; and a motor in the housing, the motor configured to cause the member to oscillate at an oscillation frequency for inducing tear production or a sinus effect; wherein the handheld device has an operational sound level that is 40 dB or less.

Optionally, the motor is configured to cause the member to oscillate without using mechanical linkage to move the member relative to the motor, thereby allowing the handheld device to have the operational sound level that is 40 dB or less.

Optionally, the motor has a weight that is supported by the member.

Optionally, the motor is fixedly attached to the member.

Optionally, the motor has a motor housing, and the motor housing is attached to the member.

Optionally, the motor comprises a shaft, and the handheld device further comprises an eccentric mass secured to a shaft of the motor.

Optionally, the motor and a portion of the member are configured to move together.

Optionally, the handheld device further includes an electrical wire connected to the motor, wherein at least a portion of the electrical wire is coupled to the member.

Optionally, the member has a first bending stiffness in a first bending direction, and a second bending stiffness in a second bending direction, the second bending stiffness being higher than the first bending stiffness.

Optionally, the first bending direction corresponds with a direction of oscillation by the member.

Optionally, the member has a cross section with a first side and a second side, the first side being longer than the second side, and wherein the motor is attached to the first side.

Optionally, the motor is configured to cause the member to undergo bending action in a reciprocating manner.

Optionally, the member comprises a cantilevered beam having a free end, the exterior surface being at the free end of the cantilevered beam.

Optionally, the motor is configured to cause the cantilevered beam to undergo bending action in a reciprocating manner.

Optionally, a speed of the motor is variable based on an amount of force applied at the exterior surface.

Optionally, the oscillation frequency of the member is variable based on an amount of force applied at the exterior surface.

Optionally, the handheld device further includes a power source accommodated in the housing.

Optionally, the handheld device further includes a port configured to receive an adapter for charging the power source.

Optionally, the power source is a rechargeable battery.

Optionally, the member is configured to oscillate with an amplitude that is anywhere between 0.25 mm and 1.5 mm.

Optionally, the member has a durometer that is anywhere between 40 A to 60 A.

Optionally, the member is configured to oscillate with a force that is anywhere from 1 N to 3 N.

Optionally, the oscillation frequency of the member is anywhere from 50 Hz to 300 Hz.

Optionally, the handheld device further includes a storage medium configured to store information related to a treatment duration, a treatment start time, a treatment end time, an applied force, a treatment frequency, or any combination of the foregoing.

Optionally, the motor is configured to oscillate the member at the oscillation frequency to stimulate a nasal nerve.

Optionally, the body portion comprises a nose region, and the member is configured to apply the mechanical vibration to the nose region.

Optionally, the body portion comprises a facial region, and the member is configured to apply the mechanical vibration to the facial region.

Optionally, a portion of the member is configured for placement over an infraorbital nerve.

Optionally, a portion of the member is configured for placement over an anterior ethmoidal nerve.

Optionally, a portion of the member is configured for placement over an external nasal nerve.

Optionally, a portion of the member is configured for placement over an eyelid or on a sclera of an eye.

Optionally, a portion of the member is configured for placement along a sensory portion of an ophthalmic nerve division of a trigeminal nerve.

Optionally, a portion of the member is configured for placement inside a nasal opening.

Optionally, the exterior surface has a curvilinear surface.

Optionally, the exterior surface has a convex configuration.

Optionally, the convex configuration of the exterior surface allows an area of contact with the individual to be adjustable.

Optionally, the exterior surface has a convex exterior surface.

Optionally, the handheld device further includes a power switch operable by the individual to activate the handheld device.

Optionally, the power switch comprises a button, wherein the handheld device is configured to be activated in response to a pressing of the button, and is configured to be de-activated when the button is un-pressed.

Optionally, the member has a portion located inside the housing.

Optionally, the housing comprises an opening, and the member is configured to oscillate within the opening.

Optionally, the member is configured to be selectively placed on either a right side or a left side of the individual.

Optionally, the housing comprises an opening, wherein the member is configured to oscillate within the opening, and wherein the member is configured to elastically retract into the housing with a spring constant in response to external force applied against the member.

Optionally, the member is configured to simultaneously apply the mechanical vibration to a right side and a left side of the individual.

Optionally, a portion of the member has a thickness measured in a direction that is parallel to a skin against which the second portion is to be applied, the thickness being between 0.5 mm and 3 mm.

Optionally, a portion of the member has a tissue-contacting surface, a side wall, and a dull corner between the tissue-contacting surface and the side wall.

A method to treat a condition of an individual, includes: receiving a switch signal generated based on a manipulation of a control switch at a handheld device; and activating a motor in response to the switch signal to oscillate a member at an oscillation frequency; wherein the oscillation frequency is sufficient to induce tear production or a sinus effect when the portion of the member is applied towards a body portion of the individual; and wherein the handheld device generates sound that is less than 40 dB when the member oscillates.

Optionally, the motor causes the member to oscillate without using mechanical linkage to move the member relative to the motor, thereby allowing the handheld device to have the operational sound level that is 40 dB or less.

A handheld device for applying mechanical vibration to a body portion of an individual to treat a condition of the individual, includes: a housing; a member having an exterior surface for contacting the individual, the member configured to oscillate to apply the mechanical vibration to the body portion; and a motor in the housing, the motor configured to cause the member to oscillate at an oscillation frequency for inducing tear production or a sinus effect; wherein the motor is configured to cause the member to oscillate without using mechanical linkage to move the member relative to the motor, thereby allowing the handheld device to have an operational sound level that is 40 dB or less.

A handheld device for applying mechanical vibration to a body portion of an individual to treat a condition of the individual, includes: a housing; a cantilever beam having a first portion accommodated in the housing, and a second portion that is moveable relative to the housing, wherein the second portion is configured to apply the mechanical vibration to the body portion; and a motor in the housing, the motor configured to oscillate the second portion of the cantilever beam at an oscillation frequency.

Optionally, the motor is fixedly attached to the cantilever beam.

Optionally, the motor has a motor housing, and the motor housing is attached to the cantilever beam.

Optionally, the motor comprises a shaft, and the handheld device further comprises an eccentric mass secured to a shaft of the motor.

Optionally, the motor and the second portion of the cantilever beam are configured to move together.

Optionally, the handheld device further includes an electrical wire connected to the motor, wherein at least a portion of the electrical wire is coupled to the cantilever beam.

Optionally, the cantilever beam has a first bending stiffness in a first bending direction, and a second bending stiffness in a second bending direction, the second bending stiffness being higher than the first bending stiffness.

Optionally, the first bending direction corresponds with a direction of oscillation by the second portion of the cantilever beam.

Optionally, the cantilever beam has a cross section with a first side and a second side, the first side having a larger dimension than the second side, and wherein the motor is attached to the first side.

Optionally, the motor configured to oscillate the cantilever beam at an oscillation frequency sufficient to induce tear production or a sinus effect when the second portion of the cantilever beam is applied towards a surface of the body portion.

Optionally, the motor is configured to cause the cantilever beam to undergo bending action in a reciprocating manner.

Optionally, the cantilever beam has a free end, the second portion being at the free end of the cantilever beam.

Optionally, the cantilever beam has a fixed end, the first portion being at the fixed end of the cantilever beam.

Optionally, the second portion of the cantilever beam is configured to oscillate with an amplitude that is anywhere between 0.25 mm and 1.5 mm.

Optionally, the second portion of the cantilever beam has a durometer that is anywhere between 40 A to 60 A.

Optionally, the second portion of the cantilever beam is configured to oscillate with a force that is anywhere from 1 N to 3 N in free air.

Optionally, an oscillation frequency of the cantilever beam is anywhere from 50 Hz to 300 Hz.

Optionally, an oscillation frequency of the cantilever beam is anywhere from 200 Hz to 300 Hz.

Optionally, the handheld device further includes a storage medium configured to store information related to a treatment duration, a treatment start time, a treatment end time, an applied force, a treatment frequency, or any combination of the foregoing, and wherein the information is for tailoring a patient specific treatment.

Optionally, the motor is configured to oscillate the second portion of the cantilever beam at an oscillation frequency sufficient to stimulate a nerve to induce the tear production.

Optionally, the body portion comprises a nose region, and the second portion of the cantilever beam is configured to apply the mechanical vibration to the nose region.

Optionally, the body portion comprises a facial region, and the second portion of the cantilever beam is configured to apply the mechanical vibration to the facial region.

Optionally, the second portion of the cantilever beam is configured for placement over an infraorbital nerve.

Optionally, the second portion of the cantilever beam is configured for placement over an anterior ethmoidal nerve.

Optionally, the second portion of the cantilever beam is configured for placement over an external nasal nerve.

Optionally, the second portion of the cantilever beam is configured for placement over an eyelid or on a sclera of an eye.

Optionally, the second portion of the cantilever beam is configured for placement along a sensory portion of an ophthalmic nerve division of a trigeminal nerve.

Optionally, the second portion of the cantilever beam is configured for placement along a maxillary portion of an ophthalmic nerve.

Optionally, the second portion of the cantilever beam is configured for placement inside a nasal opening.

Optionally, the second portion of the cantilever beam is configured to apply a vibrational force having a first directional component that is perpendicular to a surface of the body portion.

Optionally, the vibrational force has a second directional component that is parallel to the surface of the body portion.

Optionally, the second portion has a curvilinear surface for contacting the body portion.

Optionally, the second portion has a convex exterior surface.

Optionally, the handheld device further includes a power switch operable by the individual to activate the handheld device, wherein the power switch comprises a button, wherein the handheld device is configured to be activated in response to a pressing of the button, and is configured to be de-activated when the button is un-pressed.

Optionally, the second portion has a thickness measured in a direction that is parallel to a skin against which the second portion is to be applied, the thickness being between 0.5 mm and 3 mm.

A handheld device for applying mechanical vibration to a body portion of an individual to treat a condition of the individual, includes: a housing; a cantilever beam having a first portion accommodated in the housing, and a second portion that is moveable relative to the housing, wherein the second portion is configured to apply the mechanical vibration to the body portion; and a motor in the housing, wherein the motor and the second portion of the cantilever beam are configured to move together.

Optionally, the motor has a motor housing, and the motor housing is attached to the cantilever beam.

Optionally, the motor comprises a shaft, and the handheld device further comprises an eccentric mass secured to a shaft of the motor.

A handheld device for applying mechanical vibration to a body portion of an individual to treat a condition of the individual, includes: a housing; a cantilever beam having a first portion accommodated in the housing, and a second portion that is moveable relative to the housing, wherein the second portion is configured to apply the mechanical vibration to the body portion; and a motor in the housing, wherein the motor has a motor housing, and the motor housing is attached to the cantilever beam.

Optionally, the motor comprises a shaft, and the handheld device further comprises an eccentric mass secured to a shaft of the motor.

Other features and aspects will be described in the detailed description.

BRIEF DESCRIPTION OF THE DRAWINGS

The novel features are set forth with particularity in the appended clauses. A better understanding of the features and advantages will be obtained by reference to the following detailed description that sets forth illustrative embodiments and the accompanying drawings of which:

FIG. 29A depicts a side view of an end effector of a clinically effective device according to Table 1.

FIG. 29B depicts a top view of an end effector of a clinically effective device according to Table 1.

FIG. 30A depicts a side view of an end effector of a clinically ineffective device according to Table 1.

FIG. 30B depicts a top view of an end effector of a clinically ineffective device according to Table 1.

DETAILED DESCRIPTION

Figure 1:
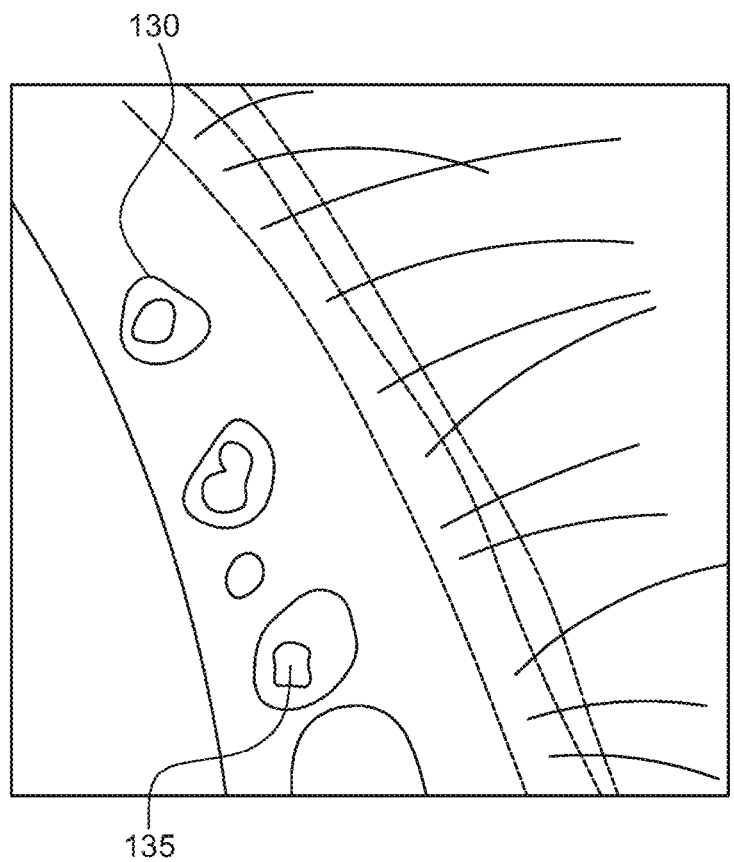
FIG. 1 depicts a tear duct with inspissated material.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

One or more of the embodiments described herein pertain to utilizing mechanical force to treat disorders of the eye including disorders of the front of the eye and the back of the eye.

Sound, ultrasound, and vibration are utilized interchangeably in this disclosure. Mechanical vibration at audible frequencies (20 to 20,000 Hz) may or may not actually transmit audible sound waves but may transmit force to a surface and is included in the broad definition of sound and ultrasound. Vibration, or mechanical vibration, is the broadest term and encompasses all sound or ultrasound regardless of whether pressure waves are created. Sound is simply mechanical vibration which transmits pressure waves through a medium which is then processed and "heard." Vibration as a category encompasses ultrasound and sound as well as mechanical vibration which may not result in sound. For example, mechanical vibration may be delivered by a probe with a linear motion, a planar motion, or motion in all three axes. The important aspect of mechanical vibration is the motion and a frequency of at least a few Hertz (Hz). The underlying mechanism of purposeful vibration (as opposed to unwanted vibration created incidentally to another mechanism such as a running motor) is to and from motion intentionally created by a moving mechanism along with transduction to another medium, for example, a body tissue of a human subject. The motion of the vibration can be created by a number of different mechanisms including motors with a gear and camshaft to create an offset, an eccentric motor, a linear resonant actuator, a voice coil, and a piezoelectric mechanism. In this respect, mechanical vibration is easier to create than sound.

The frequency of the sound waves may range from the low frequency sub audible range to the higher frequency inaudible ultrasound range. Devices described herein treat dry eye by increasing the amount of tears in the eye or treat congestion by activating nerves in the nose region. These devices act synergistically with devices which improve the quality of the tear film. These devices create tears by activating the sphenopalatine ganglion (indirectly or directly) and/or facial nerve branches, and/or ethmoidal nerves with ultrasound or sound or mechanical vibration externally applied through the skin of the nose. An example of a direct stimulation of the sphenopalatine ganglia is through stimulation of the ganglia itself. An example of indirect stimulation of the sphenopalatine ganglia is through activation of a sensory pathway which then communicates via reflex neural circuit to the sphenopalatine ganglia to increase output or tears. Another embodiment can treat a variety of disorders utilizing sound and/or ultrasound and/or vibration which is externally applied to the skin of the head and neck and activates nerves or nerve ganglia under the skin. Another embodiment applies vibratory energy to the mucosa inside of the nose or to the mucosa on the inside of the eyelids to treat dry eye.

The nasolacrimal apparatus is the physiological system containing the orbital structures for tear production and drainage. It consists of the lacrimal gland, the lacrimal canaliculi, and the nasolacrimal duct which communicates with the cavity of the nose. The innervation of the lacrimal apparatus involves both the sympathetic supply through the carotid plexus of nerves around the internal carotid artery, and parasympathetically from the lacrimal nucleus of the facial nerve in the brainstem. Signals travel from sensory (afferent) fibers around the face to the area of the salivary nucleus in the brainstem to activate the parasympathetic fibers which travel back to the sphenopalatine ganglia to synapse and then send terminal nerve fibers to innervate the lacrimal gland.

As shown in FIG. 1, tear ducts 130 may contain inspissated oils, or may be otherwise blocked with material 135 preventing tears or tear components (e.g. oils, lipids, etc.) from being excreted into the tear film of the eye. In one example, a disease which is treated by the methods and devices described herein is dry eye.

In another embodiment, eyelash growth is stimulated with mechanical vibration. For example, it has been shown in previous models in bone tissue that ultrasound delivered at 50 kHz and 1 MHz stimulates prostaglandin release (Bone 2002 Jul. 31; 236-41). Prostaglandin release has been considered the main mechanism of action for the pharmaceutical agent bimatoprost, an FDA approved agent to stimulate eye lash growth. Therefore, in one embodiment, a vibratory stimuli is utilized to upregulate prostaglandin synthesis and increase thickness of eyelashes in a subject. Indeed, any of the embodiments herein may be combined with pharmaceuticals.

Ultrasound, sound, or vibration can be used to heat and/or vibrate the material 135 to remove it from the duct 130, as shown in FIG. 1. In some embodiments, the ultrasound frequency chosen is one which resonates at the interface of the duct and the inspissated material to dislodge or heat the material in the duct so that the secretions from the duct can reach the eye and prevent dry eye. For example, early work has shown that sound frequencies in the 100 Hz to 500 Hz range will lead to break up of the material in the inspissated ducts. When combined with higher frequency ultrasound energy (e.g. 1 MHz to 3 MHz), the material can be heated to improve the efficiency of the unblocking of the ducts. In some embodiments, temperature measurement is utilized to facilitate the safety and efficacy of the treatment; a temperature range of between 40 and 48 Celsius is the preferred temperature. The temperature can be controlled with closed loop control in which a thermistor is utilized to measure temperature and then the feedback through a control circuit is utilized to control the power output so as to maintain the temperature in a pre-specified range.

Figure 2:
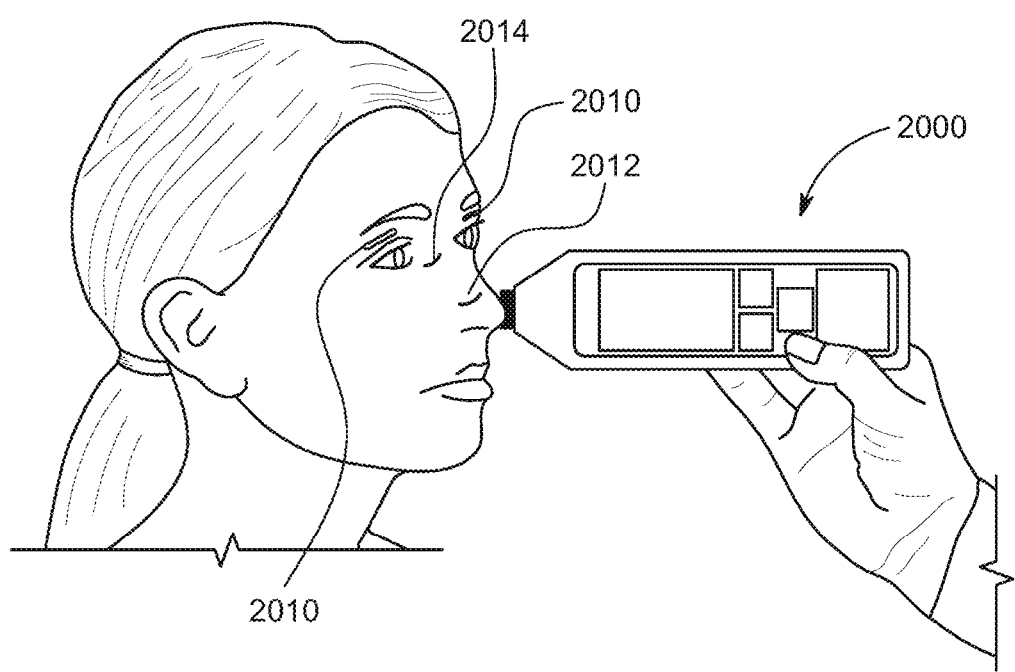
FIG. 2 depicts a device to deliver vibrational energy to the nasal turbinates and nerves inside the nasal cavity via contact through the skin and bony structures of the nose.

FIG. 2 depicts an embodiment of a device to stimulate the lacrimal gland or other nerves or ganglia transcutaneously through the skin to the nerves and ganglia. Regions 2012, 2014, and 2010 have been shown experimentally to produce the greatest amount of nerve stimulation by way of vibration of the facial bones which in turn stimulate the nerves such as sphenopalatine ganglia, lacrimal nerve, external nasal nerve, infratrochlear nerve, supratraochlear nerve, infraorbital nerve, supraorbital nerve etc. For example, region 2012, when exposed to direct skin vibration at approximately 100 Hz-300 Hz vibration produces copious bilateral tear formation and relieves congestion when just a single side is stimulated. In some embodiments, vibrations from about 50 Hz to about 500 Hz are utilized to stimulate the bones of the face to, in turn, transmit vibrations to the nerves which stimulate tear production. The treatment works best at the resonant frequency of the bone so that the vibration of the bone is maximal and affects the nerve maximally due to the greatest amount of mechanical movement of the nerve and subsequent stimulation. The resonant frequency of the bone is to some extent individualized per patient. This frequency has been experimentally determined and subsequently proven to be in the range of about 100-300 Hz.

Region 2014 (FIG. 2) includes the bottom eyelid (inner and outer eyelid), the medial canthus of the eye along the nasolacrimal duct. External stimulation along these regions in some embodiments stimulates the nerves through bony resonance and, in some embodiments, stimulates the glands in the lower eyelid region directly.

Figure 3:
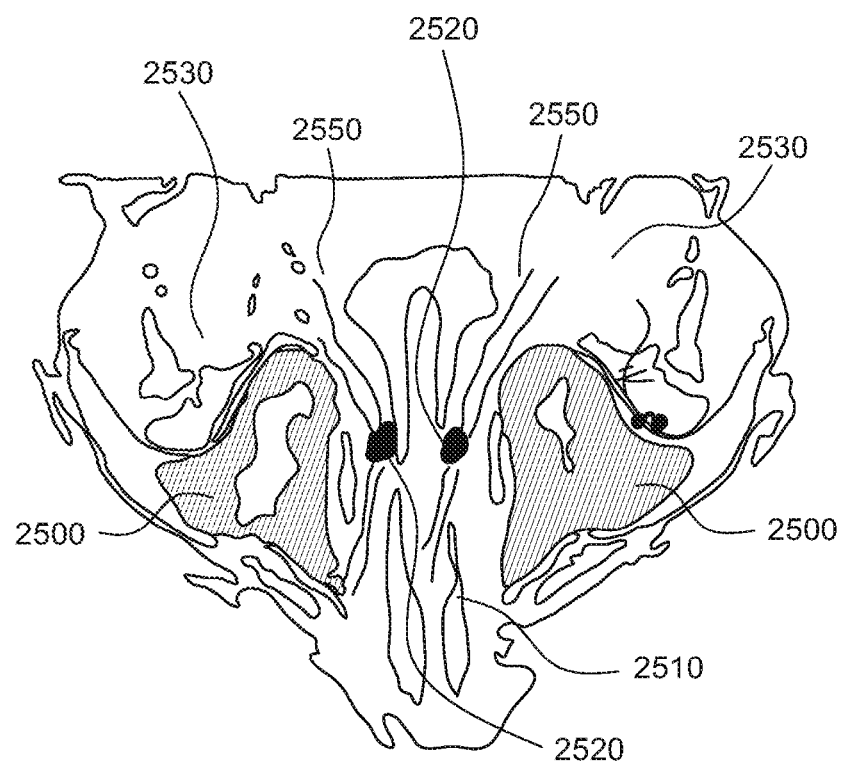
FIG. 3 depicts a coronal section through the sinuses

FIG. 3 depicts neural pathways involved in the transduction of vibration from the skin to the lacrimal gland when vibrations are applied through the preferred external location 2012 in FIG. 2. Ganglia 2520 projects nerves to the lacrimal nerve 2550 which courses to the orbit to stimulate the main lacrimal gland in the superior portion of the orbit. Bone 2530 transmits vibrations to the lacrimal nerve 2550 and around the maxillary sinus 2500 via the sphenopalatine ganglia. The sphenopalatine ganglia 2520 is covered by mucosa and sits between the turbinates which are accessible transnasally through the external nasal passageways 2510. The external nasal nerve is a terminal branch of the ophthalmic branch of the trigeminal nerve and is directly stimulated with vibration as it is compressed against its exit from underneath the nasal bone at the junction of the nasal bone and the anterior lateral nasal cartilage. In another embodiment, an ultrasound or sound producing probe is inserted through the external nasal passageways 2510 and applied to the mucosa in proximity to the sphenopalatine ganglia 2520 to stimulate tear production through direct stimulation or via the nasolacrimal reflex. In another embodiment, a vibratory probe with vibration at approximately 100-300 Hz is inserted into the nasal passage to directly stimulate the sphenopalatine ganglia and/or the interior anterior ethmoidal nerves on the interior of the nasal passage. In another embodiment, electrical stimulation of the external nasal nerve accomplishes tearing by activating the lacrimal nucleus in the pons and subsequently pre-gangliotic fibers within the maxillary nerve which synapse in the sphenopalatine ganglia and then stimulate the lacrimal nerve to produce tears.

In one embodiment, a method to stimulate neural pathways through the application of sound or ultrasound energy transcutaneously is described. An applicator is disposed to the face of the patient, the applicator comprising one or more vibratory elements capable of generating vibrations from about 50 Hz to about 50 kHz. The vibration is applied to a region close to a nerve under the skin or to a region with a bony prominence which communicates via bone structure with a nerve region located close to the skin. For example, an applicator 2000 disposed to the region 2010, 2012 (FIG. 2) or 2014 (FIGS. 2, 4) will transmit the vibratory energy to the lacrimal glands and produce tears. The resonant frequency is different for each person as is the exact location and direction of the vibration. In one embodiment, the individual resonant frequency is determined and the device adjusted to this frequency for each person. An interface between the device and the patient's skin is similarly adjustable so that the vibrations are transmitted to the nerves in the head and neck region to be stimulated. For example, the parasympathetic nerve which innervates the lacrimal gland travels within the maxillary bone and the sphenopalatine ganglia is located close to the maxillary bone in the sphenopalatine fossa. At a resonant frequency of the maxillary bone, it has been discovered that the ganglia can be stimulated and tears produced. The resonant frequency is achieved through a combination of material, vibration frequency, and amplitude. For example, a material with a durometer between Shore A40 and Shore A60 vibrating over a surface area of between 5 mm$^2$ and 20 mm$^2$ with an amplitude of about 0.5 to 5 mm and frequency of between 50 Hz and 400 Hz results in copious tears. With a directionality upward and at a location approximately along the nasal bone where it meets the cartilage, tears can be produced without discomfort or sneezing or other nasal symptoms. The total force applied over the surface area in some embodiments is about 1 N (Newton). In other embodiments, the total force is from about 0.5 N to bout 2 N. In other embodiments, the force is about 0.25 N to about 4 N.

In some embodiments, the device is connected to an iTEAR application on a smart phone. For example, the device communicates with a smart phone through a Bluetooth application or via wifi. The application on the smart phone might track usage of the device, the force applied to the cantilever of the device, the remaining power charge, the and the frequency of the device. In one embodiment, the application on the smart device takes a picture of the eye or eyes of the patient during the stimulation of the lacrimal glands. A subsequent or sequential set of images are compared to one another and the thickness of the tear film determined. The change in the tear film is determined based on a reflectance from the tear film as the result of a camera flash. Alternatively, a filter is utilized to determine the difference between pre-stimulation and post-stimulation. A custom light source can be driven by the smart device and the reflected light collected by the device. For example, an infrared, red, or blue light source can be hard wired to the device. A baseline picture is obtained and stimulation begun. The light is projected to the tear film and the tear film quantified through a series of baseline and during treatment pictures are obtained. In one embodiment, interferometry is obtained after the light is applied to the tear film.

Figure 9:
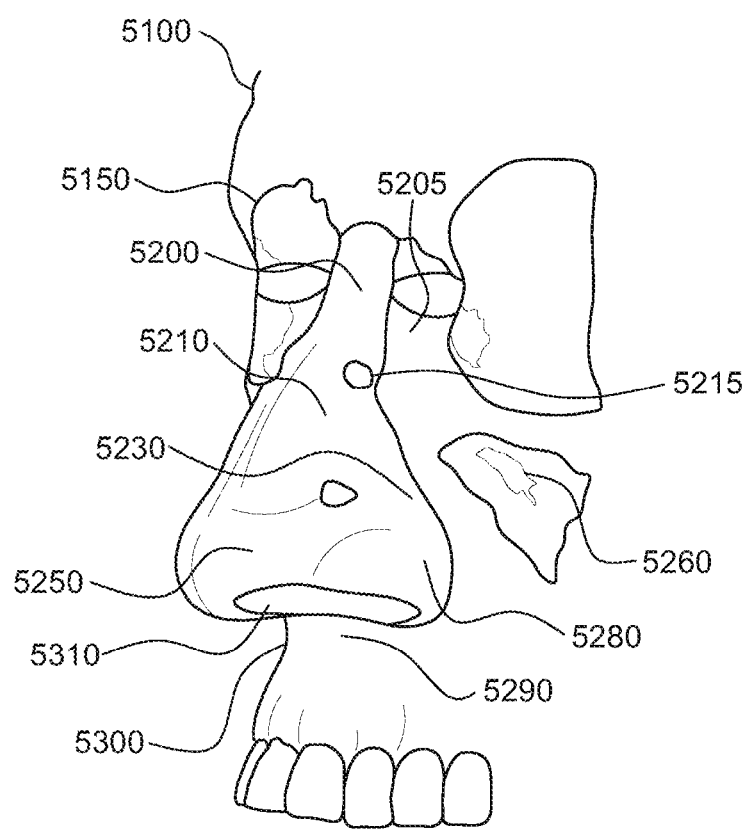
FIG. 9 depicts the boney and soft tissue structures in and around the nose.
Figure 10:
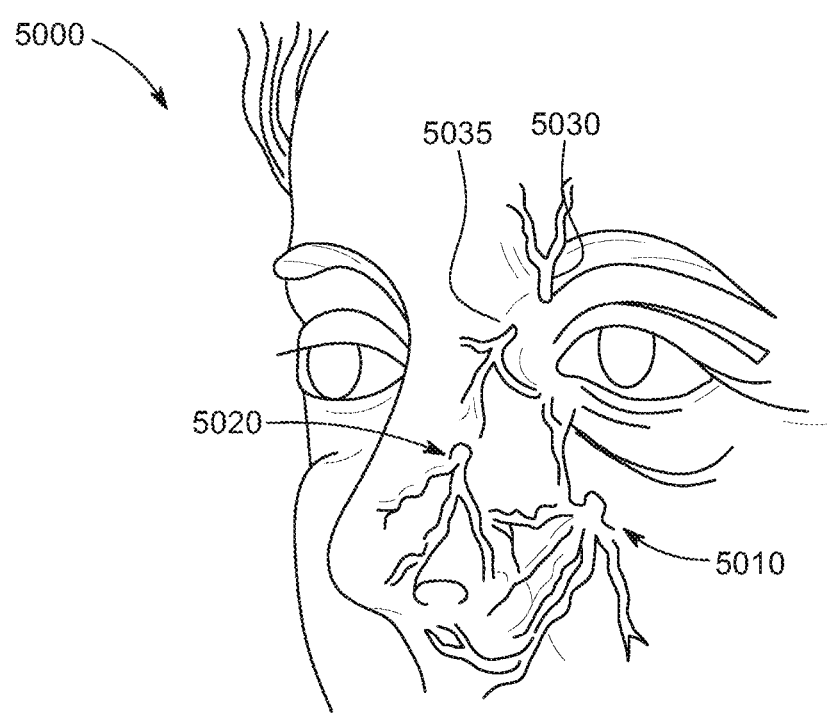
FIG. 10 depicts the nerve anatomy in and around the nose.

FIG. 9 depicts the bony anatomy of the face. FIG. 10 depicts the nervous anatomy of the face. In FIG. 10, at the point where the upper lateral cartilage meets the nasal bone, the external branch of the anterior ethmoidal nerve penetrates the nasal bone is depicted. This location is where the lateral process of the septal nasal cartilage meets the nasal bone (FIG. 9) and 2012 in FIG. 5. This is the location, located on the skin, which has been discovered through experimentation to produce tears when mechanical vibration is applied at a frequency of 50-300 Hz with a vibration amplitude of approximately 0.5 mm to 1.5 mm and/or force of about 0.5 to 1.5 N.

Furthermore, it has been discovered that direct stimulation of the infratrochlear and infraorbital nerves with mechanical vibration also induces lacrimation. Mechanical vibration can also stimulate lacrimation by direct contact with the mucosal surfaces inside the nose.

FIG. 10 depicts the neural anatomy of this region underneath the skin. The anterior ethmoidal nerve, a direct continuation of the nasociliary nerve, splits into two branches to supply the nasal mucosa, medial and lateral, as it enters the nasal cavity where is supplies the nasal mucosa. The nasociliary nerve continues to the caudal region of the nasal bone and appears 6.5 mm to 8.5 mm from the midline as the external nasal nerve The infraorbital nerve 5010 exits the bone and travels into the skin approximately 1-2 cm below the lower eyelid. It is the external nasal nerve which has been determined to induce tearing when vibrations at 50-300 Hz are applied. Electrical stimulation (bipolar or monopolar) of the external nasal nerve in this region also can be utilized to induce lacrimation.

A well described pathway for lacrimation is called the nasolacrimal reflex in which stimulation of afferent fibers of the anterior ethmoidal nerve (accessible inside the nose) travel through the ophthalmic nerve to the salivary nucleus in the brain stem, then parasympathetic nerve signals travel via the maxillary branch of the trigeminal synapse in the sphenopalatine ganglia to innervate the lacrimal nerve and stimulate the lacrimal glands. Parasympathetic fibers generally stimulate the lacrimal glands and also partially innervate the Meibomian glands.

In addition to the specific descriptions set forth herein, it has been discovered through extensive experimentation that stimulation of the external nasal nerve achieves lacrimation. As described above, the external nasal nerve 5020 exits to the surface of the skin from deep to the layers of the skin through an orifice at the junction of the nasal cartilage and nasal bone. It is not accessible by electrical stimulation. As described herein, certain vibrational parameters result in stimulation of lacrimation similar to the nasolacrimal reflex.

The external nasal nerve is a continuation of the nasociliary nerve which originates from the ophthalmic branch of the trigeminal nerve. Prior to its exit from the inner portion of the nose to the external portion of the nose, it gives off two branches to the inner portion of the nose. The external nasal branch is the terminal nerve of the nasociliary nerve. After exiting the inner portion of the nose between the nasal bone and the upper lateral cartilage (through a notch in the nasal bone), the external nasal nerve dips into the fibrofatty tissue to ultimately branch and supply the skin and fatty tissues of the distal nose. In an anatomic study, the exit of the nerve was consistently 6.5-8.5 mm lateral to the nasal midline independent of the width of nose. There were three branching patterns identified. The first was a single nerve exiting the nasal bone. The second pattern was splitting of the nerve upon exit from the nasal bone, and the third pattern was splitting of the nerve distal to the exit from the nasal bone close to the cartilage of the distal region of the nose. The nerve size in this study was consistently 0.3 mm to 0.4 mm diameter.

Therefore, in one embodiment, a device is placed approximately 6.5 to 8.5 mm lateral to the nasal midline at the region where the upper lateral cartilage meets the nasal bone. The device is placed unilaterally or bilaterally or unilaterally and then sequentially on the contralateral side for bilateral treatment. The device applies a force over an area of 1-2 mm² on the nose at frequency of 100-300 Hz. In some embodiments, approximately 0.5 to about 2.0 N of force is applied to the external nasal nerve as it leaves the nasal bone. In other embodiments, a force of approximately 2 to about 5 N is applied to the nose to activate the external nasal nerve. Despite extensive anatomic descriptions, until the current invention, there has been no description of the function of the nerve beyond the sensory distribution to the skin of the nose.

Figure 4:
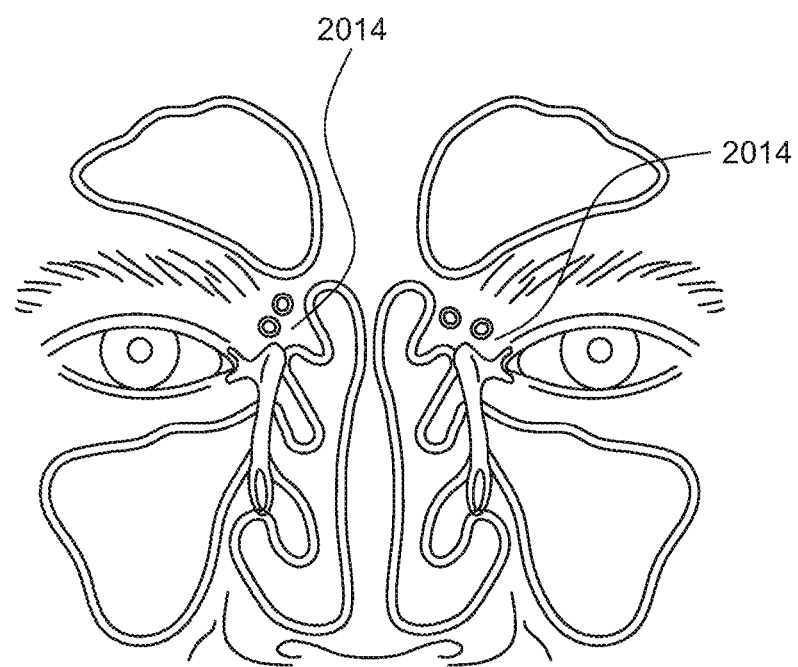
FIG. 4 depicts a coronal section through the face with the tear duct anatomy outlined.

In another embodiment in FIG. 4, the nasolacrimal duct is the target. It has been found in clinical work that stimulation of this duct internally along its length leads to stimulation of tear production. The mechanism is thought to be direct stimulation of the nasolacrimal reflex. It has been further discovered that vibration at 100-500 Hz externally through the skin in the region of the bone through which the duct travels (e.g. nasal bone) also stimulates this reflex. Similar to the external nasal nerve, electrical stimulation has been found to be ineffective in the stimulation of the reflex through this anatomy The effector interface with the face of the patient is a very important component of the energy transmission to promote safety and tolerability of the procedure. Through experimentation, the optimal durometer is somewhere between Shore 40 A (pencil eraser) and Shore 80 A (leather). Shore 60 A is about a car tire tread and Shore 70 A is a running shoe sole. With an interface which is too hard, the skin is abraded and with an interface which is too soft, the nerve is not effectively stimulated.

It has been determined that unfocused vibration at 50 Hz to about 300 Hz leads to general activation of the sphenopalatine ganglion, lacrimal nerve, external nasal nerve, infratrochlear nerve, infraorbital nerve, supraorbital nerve, or internal nasal nerve leading to inhibition of rhinitis like symptoms by overstimulation and/or relief from nasal congestion, migraines, narcolepsy, dry mouth, dry eye, and elevated intra-ocular pressure via neuromodulation. Focused, or directed vibration, be it sound in which the vibrating waves are directed toward the skin and bone by way of positioning the probe toward the nasopalatine ganglia, external nasal nerves, or eyelids, or lacrimal nerves have been determined to be more effective in eliciting specific pathways such as lacrimation.

Figure 5:
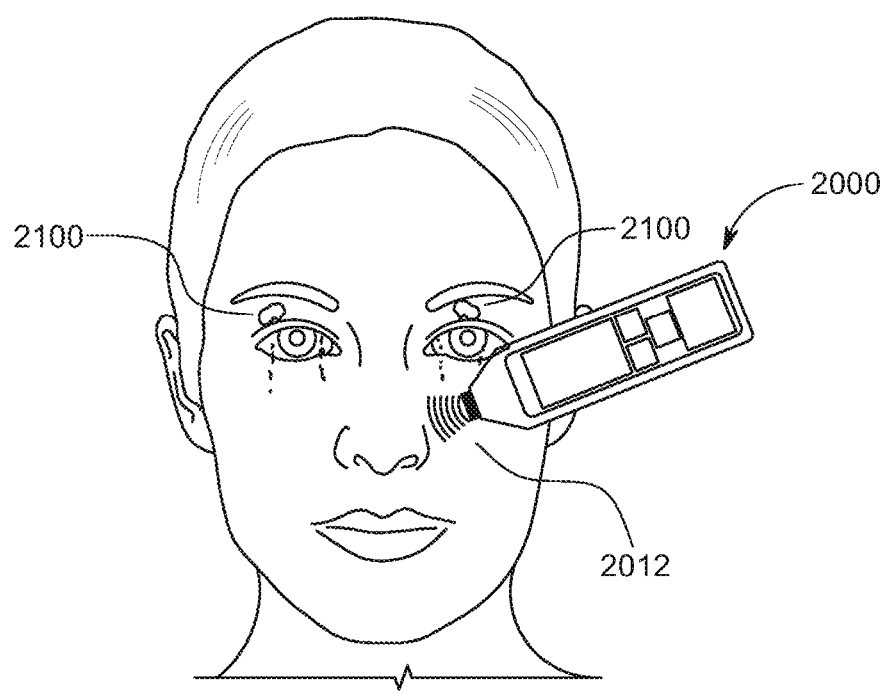
FIG. 5 illustrates an ultrasound transducer adapted to apply ultrasound energy to the tissues of the nasal cavity.

FIG. 5 depicts a device usable to activate the lacrimation pathway by applying vibration to the side of the nose and/or lacrimal pathway to activate the external nasal nerve as it exits the nasal bone onto the skin of the nose. Vibratory energy at 100-300 Hz with 1 mm excursion and 1-4 N of force stimulates the external nasal nerve when the energy is applied to the region with a sufficiently rigid biocompatible material.

In another preferred embodiment, the vibration is applied directly to the conjunctival region of the eyelid to stimulate tears directly by stimulating the accessory lacrimal glands in the lower lid and the small muscles that surround each of the Meibomian glands.

In one embodiment, the end effector of device 2000 is applied directly to the lacrimal gland 2100 or to the mucosa of the inner eyelid. Device 2000 is configured in one embodiment to run along the inner eyelid while the eyelid is being retracted to create tears, stimulate Meibomian glands, etc.

Therefore, in one embodiment, a vibratory device is applied to the skin/mucosa of the inner eyelid, applying an end effector moving at about 50-300 Hz with the end effector moving approximately 250 microns to 2 mm in excursion with 0.5 to 2 N of force, the end effector having a biocompatible material with durometer between about 60 A and 100 A and a tip which applies the force to the skin over an area of about 1 mm² to 5 mm². Pulsed frequencies (on-off) can enhance the effect. For example, the vibration can be applied with a 50% duty cycle or a 25% duty cycle with a peak amplitude greater than the base amplitude. In one embodiment, device 2000 is depressed against the skin of the nose in the region where the nasal cartilage meets the nasal bone (aka the nasal ala) 2012 where the cartilage and nasal bone meet along the side of the nose of the patient at the region where the external nasal nerve exits the nasal bone.

Figure 6:
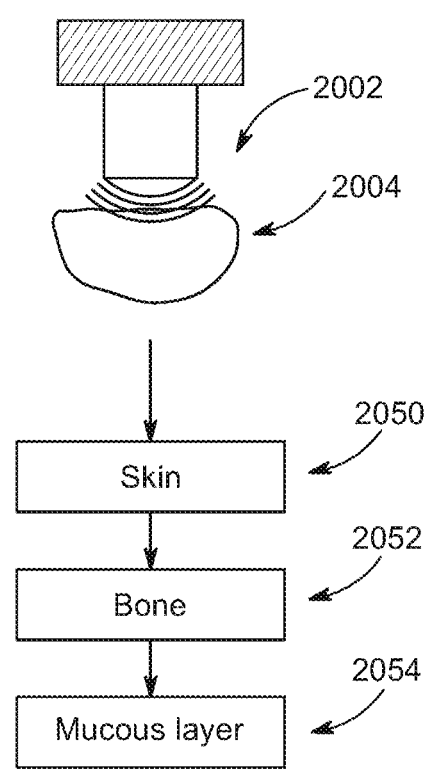
FIG. 6 depicts the interface between an ultrasound device and the tissues of the face.

FIG. 6 depicts the structural details of the ultrasound transmission from the skin through the bone and to the nerves which lie beneath the bones of the face. The end effector 2004 of the device 2002 communicates with the skin 2050 and from there, the vibrations travel through the skin 2050 to the bone 2052 and to the mucous layer 2054 underneath. From the bone, the vibration can be transmitted to the nerves in other regions of the face such as the sphenopalatine ganglia, the infraorbital nerve, the orbital nerve, the facial nerve, the trigeminal nerve, the ethmoidal nerve, and ultimately, the lacrimal nerve.

Direct stimulation of the mucous layer through bone also will accomplish direct treatment of sinus disease in addition to its effect on the nerves. Vibration and/or ultrasound stimulation of the mucosal layers will affect congestion directly by unplugging the outflow pathways and equalizing pressure.

Figure 7:
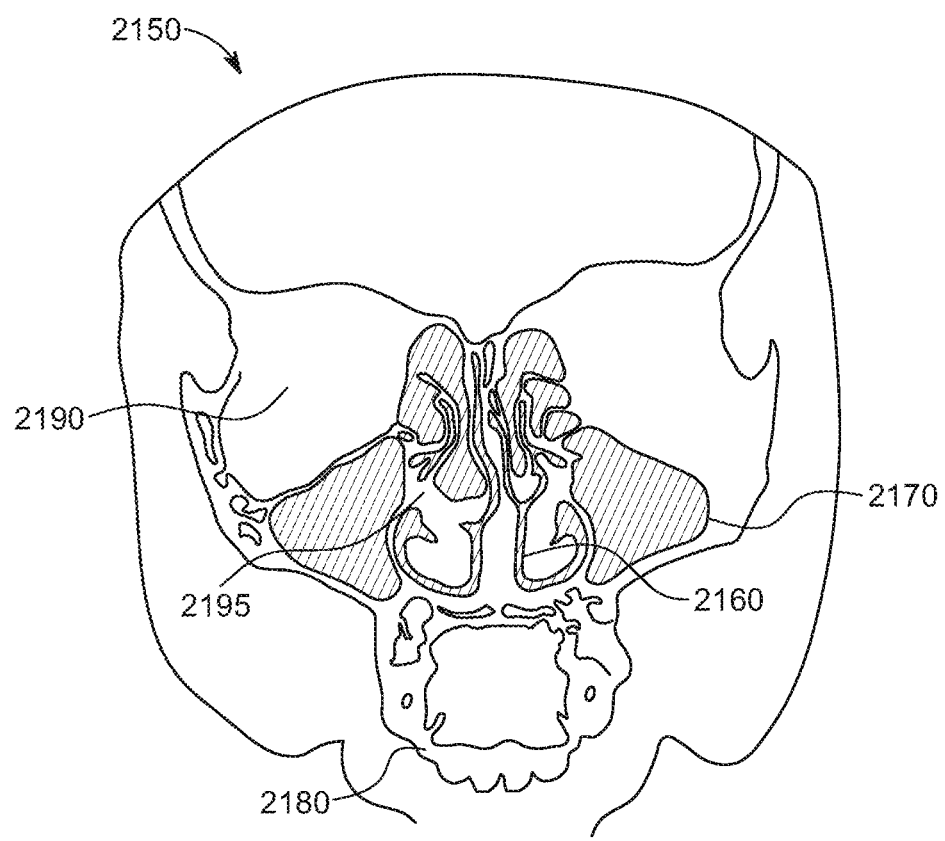
FIG. 7 depicts a coronal view of the sinuses.

FIG. 7 depicts several of the bony pathways which can communicate with nerve pathways via neuroacoustic conduction present inside the cranium 2150 and facial bones. The maxillary sinus and bone 2170 are the predominant pathway for transmission of vibratory energy to the sphenopalatine ganglia and ultimately the lacrimal nerve and gland. The conchae 2195 are folds of the maxillary bone which protrude partially into the nasal cavity. The conchae protect the olfactory bulb as well as the sphenopalatine ganglia but also play a role in transmission of sounds. The maxillary bone and its conchae communicate with the zygomatic bone 2190. The inferior turbinates 2160 are covered with respiratory mucosa. The sphenopalatine ganglia sits behind the inferior turbinates. The mandible 2180 represents an additional, albeit less direct pathway, for stimulation of the nerves of the facial region. In a preferred embodiment, a resonant frequency for these bones is utilized in order to transmit vibrational energy to the nerves within or below the bone to achieve a clinical end such as generating tears in the eye, stopping cluster headaches, migraines, seizures, rhinitis, and nasal congestion.

Figure 8:
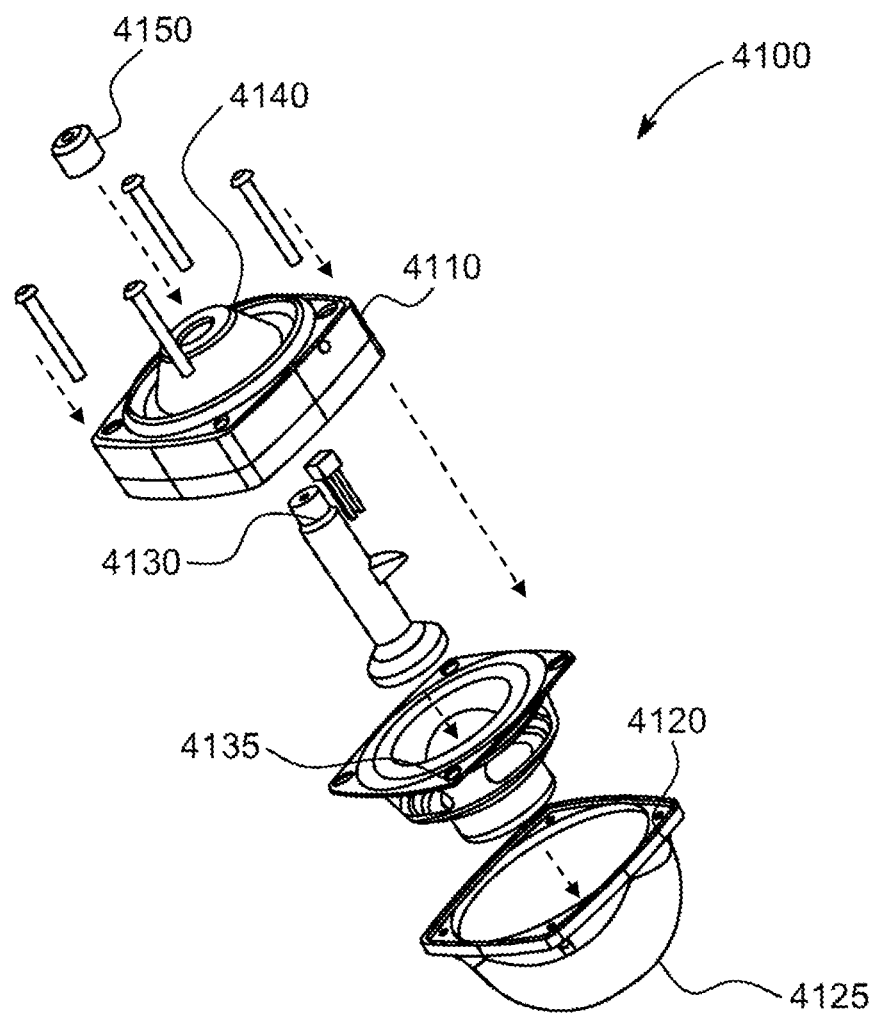
FIG. 8 depicts an assembly schematic for a device to apply vibrating energy to nerve trigger points on a face.

FIG. 8 depicts the expanded components of one embodiment of a device 4100 to stimulate tears. Item 4120 is the housing with an advanced user interface to allow for gripping the device and then applying to the external nasal nerve of a patient. Grip 4125 is a user interface for the device which contacts the palm of the user to allow for manipulation of the device while the biocompatible tip 4150 is manipulated and applied to the skin of the patient. The material is biocompatible and firm. Speaker or voice coil 4135 is the heart of the system, allowing for a continuous spectrum of frequencies, from 50 Hz all the way to kHz frequency as well as modulation of driving amplitude. Skin interface 4150 is stabilized by frame 4110. Frame 4110 also enables finger grips for further manipulation of the device. The skin interface 4150 is a biocompatible skin interface which allows for the application of cyclic force to the external nasal nerve, compressing the nerve against the nasal bone at a frequency of approximately 175 Hz to stimulate the nerve to generate tears. Shaft 4130 underneath the end effector is driven by the speaker to then drive the end effector element 4150. Interface 4140 provides the transduction interface between the speaker 4135 and the end effector 4150.

FIG. 9 depicts nasal anatomy. The frontal bone 5150 forms the upper boundary of the orbit and maxillary bone 5205 forms the medial boundary of the orbit. The frontal bone forms the roof of the frontal sinus. Maxillary bone forms the roof of the maxillary sinus 5260. The nares 5310 is the communication between the outside and the internal mucosa of the nose. The external nasal nerve leaves the nasal cavity through an orifice between the nasal bone 5200 and the lateral processes of the septal nasal cartilage 5210. It has been discovered that stimulation of the external nasal nerve in this region 5215 with force between 1-4 N using vibration at 100-300 Hz results in several clinical effects including creation of tears, abrogation of allergic and vasomotor rhinitis, relief from sinusitis, stimulation of meibomian glands, treatment of headaches, and narcolepsy. Stimulation in the region 5100, 5290, 5300, 5310, 5230, 5250, 5280, 5300 in some patients have the same effect as stimulation of the external nasal nerve. Region 5300 is the region underneath the skin of the upper lip . . . i.e. direct mucosa contact above the gum line of the teeth.

FIG. 10 depicts the cutaneous nervous anatomy 5000 in and around the nasal cavity. Cutaneous, or subcutaneous, generally refers to nerves covered by skin, dead stratified squamous, keratinized epithelial cells. In contrast, mucosa or sub-mucosal, nerves are covered by non-keratinized mucosal epithelial cells which are generally ciliated and columnar. Cutaneous nerves are more difficult to reach with certain energy forms (e.g. electrical stimulation) because the dead stratified layers broadly diffuse the current. However, vibratory stimulation can be directed to the nerves underlying the skin by transmission of pressure waves. The external branch of the anterior ethmoidal nerve 5020, also referred to as the external nasal nerve, exits at the caudal portion of the nasal bone and supplies the ipsilateral side of the nose with cutaneous nerve fibers. Infraorbital nerve 5010 supplies cutaneous fibers to the lower eyelid, upper lip, and a portion of the nasal vestibule; the vestibule is the most anterior part of the nose, lined by the same epithelium as the skin. Its epithelium transitions to the respiratory epithelium of the nasal cavity proper. The infra-trochlear nerve 5035 supplies the skin of the upper eyelids, bridge of the nose, the conjunctiva, lacrimal sac, and the caruncle (small, pink, globular nodule at the inner corner of the eye made of skin covering the sebaceous and sweat glands). The supratrochlear nerve 5030 supplies the skin of the lower forehead, the conjunctiva and the skin of the upper eyelid. It has been discovered through experimentation described herein that vibratory stimuli (e.g. 50 Hz to approximately 300 Hz) of these nerves and nerve endings stimulate the lacrimal nerve to secrete tears and the meibomian glands to secrete oils and lipid. In these embodiments, the vibratory stimuli contact the stratified epithelium of the skin not the mucosa, and energy is transferred by mechanical waves. In some patients, the mechanical stimuli is effective along the dermatomes of the skin in an around the external nasal nerve. For example, in some patients, tear stimulation is possible by applying vibratory stimulation at approximately 150-300 Hz with the patient interface as specifically designed herein along the tip of the nose, along the upper lip, along the skin of the lower eyelid, etc. In these patients, tolerance to the treatment can in some cases be completely avoided by applying the treatment to different dermatomes for each application.

In one embodiment, the lacrimal gland is activated by stimulating the infraorbital nerve, the infra-trochlear nerve, the supratrochlear nerve, the caruncle, or the conjunctiva inside the eyelids. Indeed, the conjunctiva inside the eyelids or on the surface of the eye is mucosa and the upper layers are non-keratinized. Stimulation of these tissues is optionally performed with vibratory energy including sound, ultrasound, mechanical vibration, electrical sparking, puff of air, puff or water or other liquid, or other mechanically sharp stimulation impulse. In the mucosal tissues, electrical stimulation is also more possible because of the lack of stratified epidermis diffusing the current. Therefore, in one embodiment, energy is passed through the conjunctiva of the eye to stimulate tears.

Figure 11:
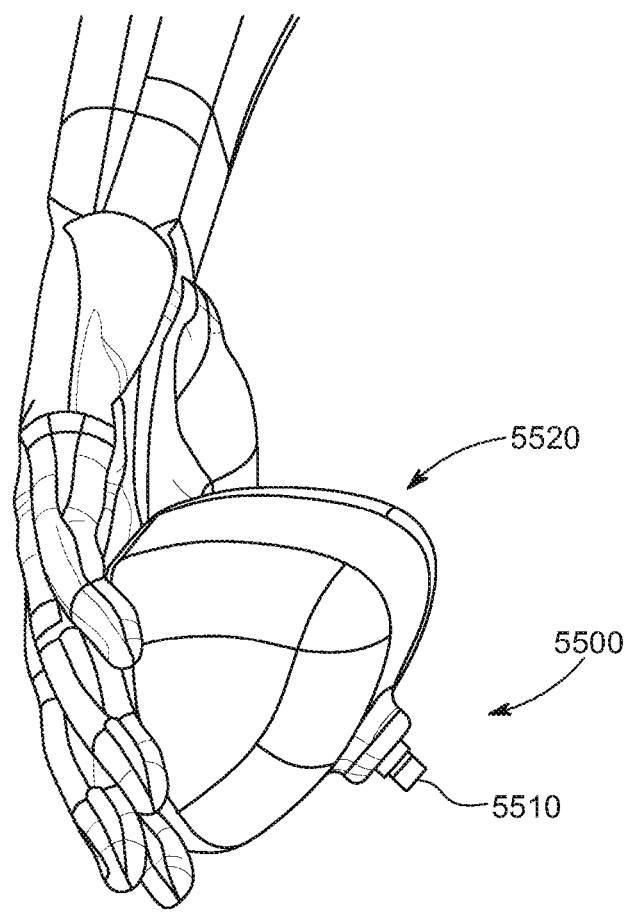
FIG. 11 depicts an embodiment of a handheld tear stimulator.

FIG. 11 depicts a handheld embodiment of a device 5500 to apply vibrational energy to the facial region in which there is an underlying parasympathetic nerve or a circuit which ultimately results in stimulation of a parasympathetic nerve. Interface 5510 moves with linear excursion substantially perpendicular to the housing 5520. Housing 5520 is configured to be handheld and self-contained, produced from a comfortable, biocompatible plastic or aluminum material. Interface 5510 is fairly rigid with a rounded yet firm tip. The radius of curvature of the tip is such that it can firmly push into the junction of the nasal cartilage and nasal bone, vibrate a 100-300 Hz, preferably between 180 and 220 Hz or at least between 75 Hz and 300 Hz with maintenance of a constant speed despite the force being applied by the user to the nerve.

Figure 12:
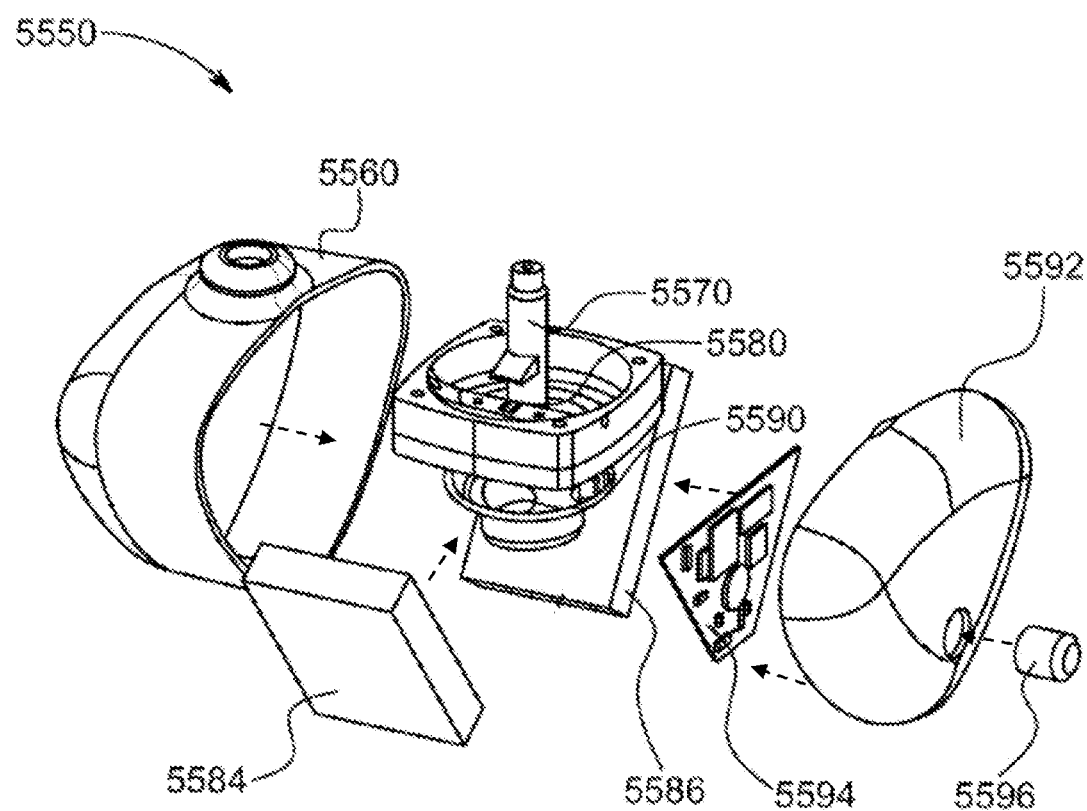
FIG. 12 depicts an expanded view of a handheld neurostimulator to create tears.

FIG. 12 depicts a detailed view 5550 of the handheld device in FIG. 11. The basic mechanism of this device is a voice coil 5590 which provides for a linear driving motion of the tip 5570. Plastic body 5560, 5592 surrounds the device. An optical distance sensor 5580 is calibrated to detect movement of the linear vibrating component 5570. Printed circuit board assembly 5594 comprises an amplifier and battery charging circuitry as well as an optional control system so that the tip 5570 vibrates at a near constant frequency. Power button 5596 and cover 5592 as well as lithium ion batteries 5584 and 5586 complete the unit. This unit is self-contained, and the lithium ion batteries are rechargeable.

Figure 13:
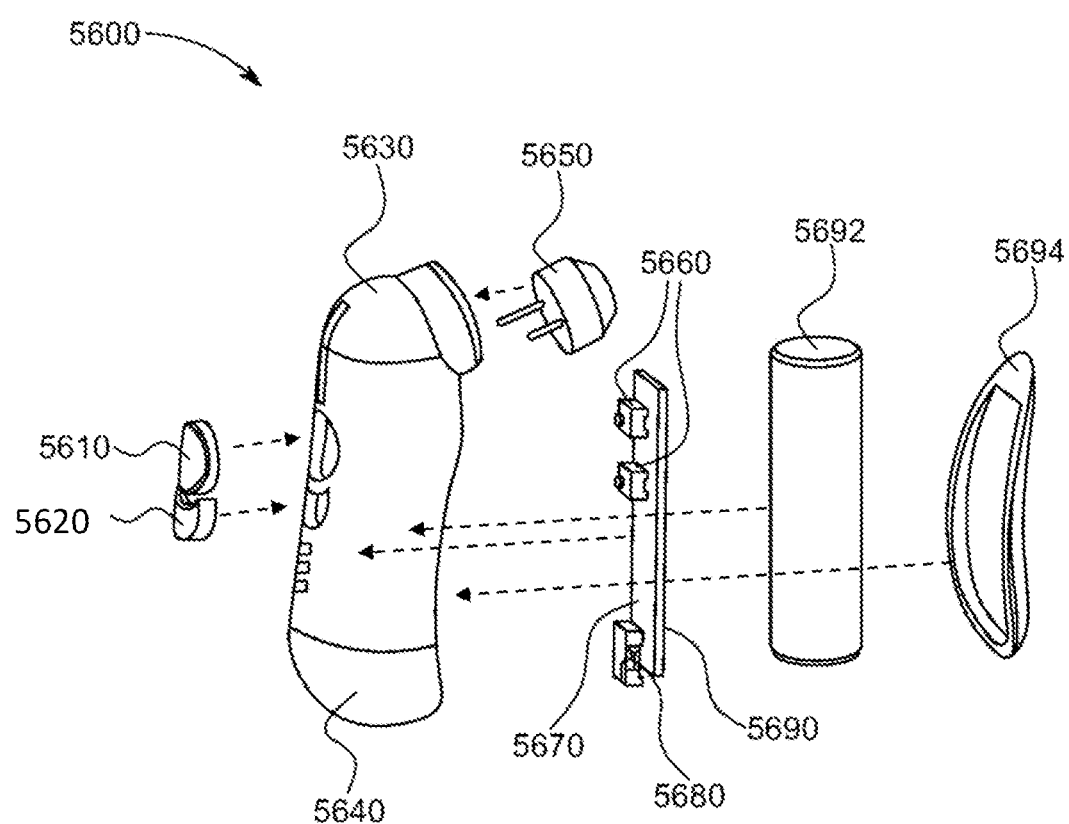
FIG. 13 depicts an expanded view of a neurostimulator device.

FIG. 13 depicts the components of a vibratory device 5600 which is configured to be held in the palm of the hand of the user with an interface 5610, 5620 with the tip of a finger of a user. Body surface interface 5650 is configured to be handheld and comfort grip 5694 is configured from a biocompatible material. Lithium ion 5692 battery is inserted into the main body housing 5630 (top) 5640 (bottom). Linear vibration motor travels with linear motion and is connected to the body surface interface to create linear motion as well. The surface interface is applied to the skin with perpendicular application to the skin to stimulate the external nasal nerve and the parasympathetic nervous system to open Meibomian glands, create secretions of oils, and produce tears from the lacrimal glands, treat migraines, epilepsy, narcolepsy, headaches, open blood brain barrier, equalize pressure, treat rhinitis and sinusitis, and nasal polyps. Tactile switches 5660, 5680 enable user guided feedback to increase or decrease stimulation level, either by signaling adjustment of the vibration amplitude and/or frequency. Structures 5670 and 5690 house the tactile sensors and transmits the signals to the use.

Figure 14:
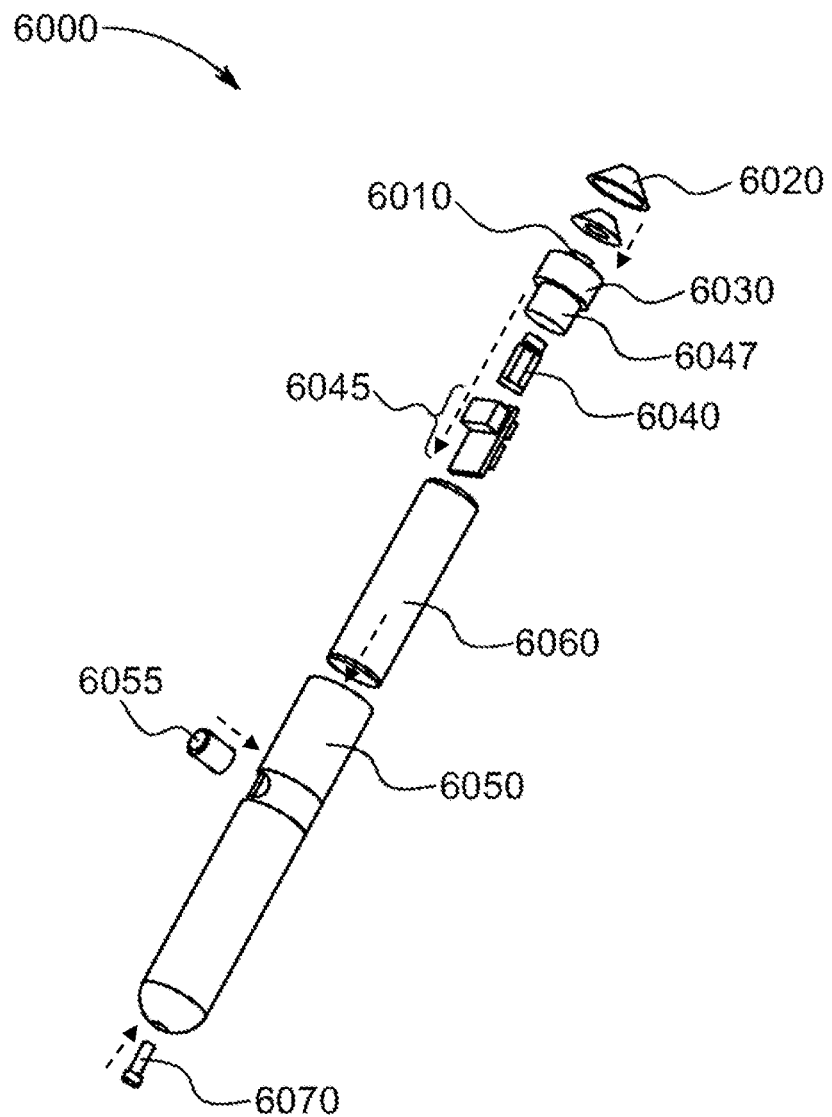
FIG. 14 depicts an expanded view of another neurostimulator device.

FIG. 14 depicts another embodiment of a device 6000 configured to apply vibrational energy to a nerve overlying a parasympathetic nerve of the face. Interface 6020 is a biocompatible skin interface designed to transfer force from the vibratory element to the skin overlying the bone of the patient and to the nerve underlying the bone. A snap element 6010 allows for quick placement and removal of the skin interface 6020. The vibration is generated by eccentric motor 6040 which vibrates the biocompatible interface with an approximately planar and perpendicular vibratory direction to the long axis of the device 6000. Contacting motor 6040 are components 6030, 6047 which are intermediate between the motor 6040 and the skin interface 6020. In some embodiments, these components are flexible or rigid which determines the flexibility or rigidity of the skin interface. In some embodiments, these components are even adjustable to create flexible patient interfaces. Switch 6055 powers the device on and off. Rechargeable battery 6060 and electrical access port 6070 enable power delivery to the device 6000. Additional electronics 6045 may include a lockout timer so that a user does not over use the device. A control system to maintain a pre-specified motor and vibration speed is also an optional feature of the circuitry. The electronics are housed in shell 6050.

Figure 15:
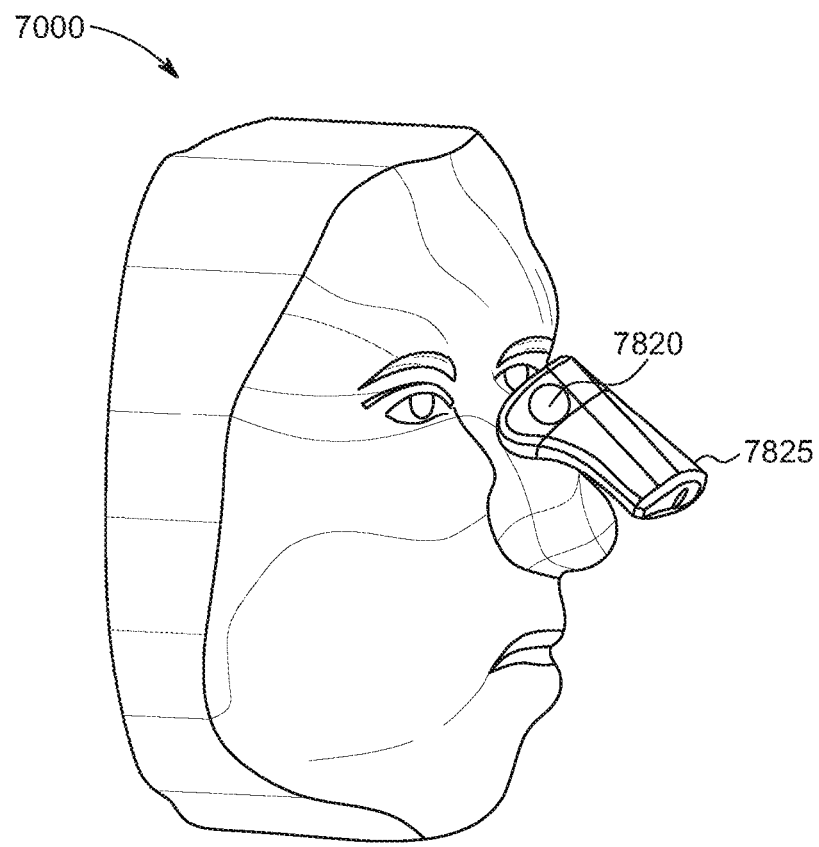
FIG. 15 depicts a device which applies mechanical vibration bilaterally to a patient.

FIG. 15 depicts a device 7000 which can be applied bilaterally to the nose of a patient to stimulate the external nasal nerve simultaneously or individually depending on patient preference. A feature of this device is that it has haptic feedback 7825 such that as the patient presses down on the device switch 7820 and on the nose, the device responds by applying a greater force or displacement to ensure nerve stimulation. In other embodiments of FIG. 15, device 7000 functions as a strip that is applied bilaterally to the nose of a patient such that each end of the strip contacts the region on the left and right side of the nose where the nasal bone meets the anterior lateral nasal cartilage where the external nasal nerve is located.

Figure 16:
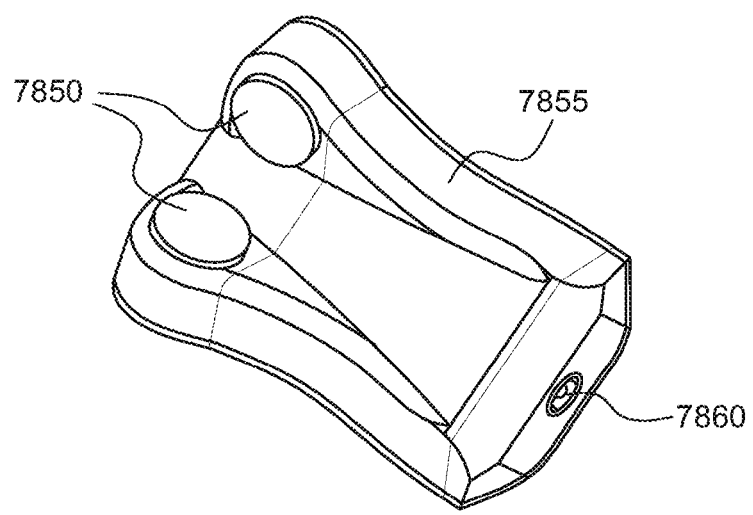
FIG. 16 depicts the device in FIG. 15 in more detail.

FIG. 16 depicts the underside of the device shown in FIG. 15. Pressure sensors 7850 sense the force being applied by the user. Material 7855 is preferably flexible so that the user can squeeze the device and compress the external nasal nerve and apply increasing vibrational force, the degree of which is dictated by the force the pressure sensor senses on the skin. The device is rechargeable via port 7860 which can also potentially serve as a data port.

Figure 17:
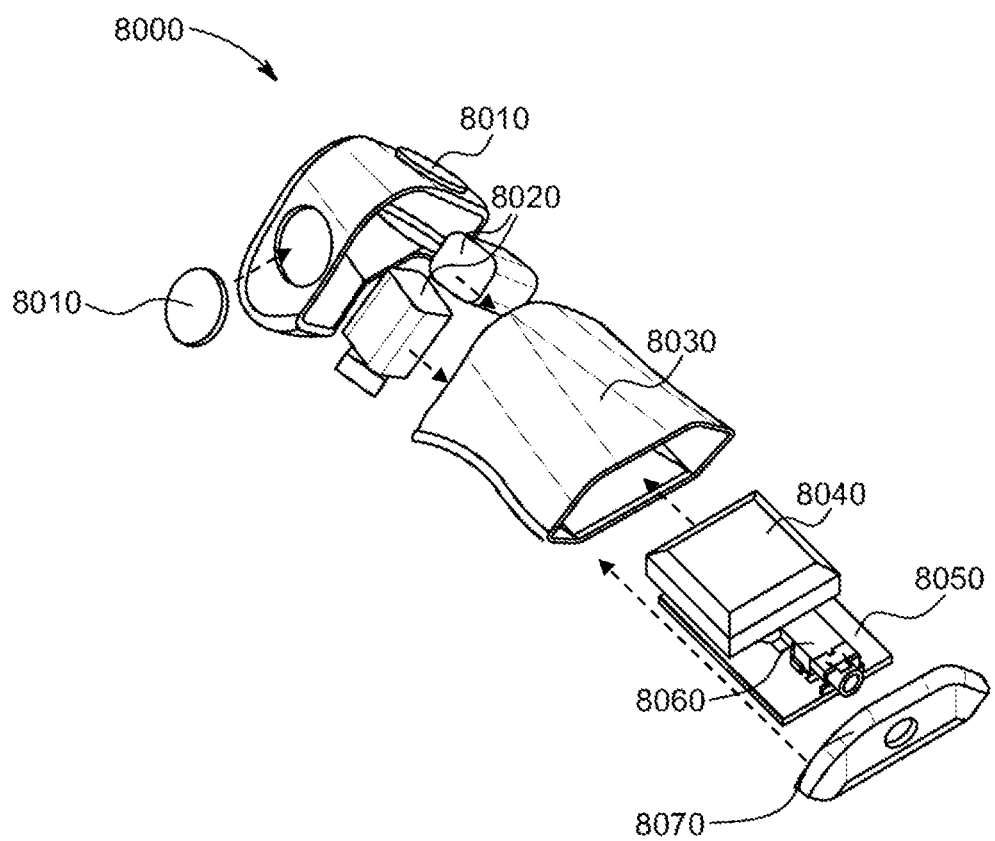
FIG. 17 depicts the inner mechanism of a device to create tears in a patient.

FIG. 17 depicts a schematic of the individual components of the device 8000 shown in FIG. 15. Pressure sensors 8010 enable coupling between the force applied by the user and the speed, torque, and force of the eccentric motors 8020 which create the vibratory effect to stimulate the external nasal nerve and parasympathetic pathway. Element 8030 is a housing for electronics and for the patient to grip while applying the vibration to the external nasal nerve and parasympathetic pathway. Battery 8040 is preferably rechargeable but also may be a replaceable battery. Cover 8070 seals the electronic circuit board 8050 and charge port 8060.

Figure 18:
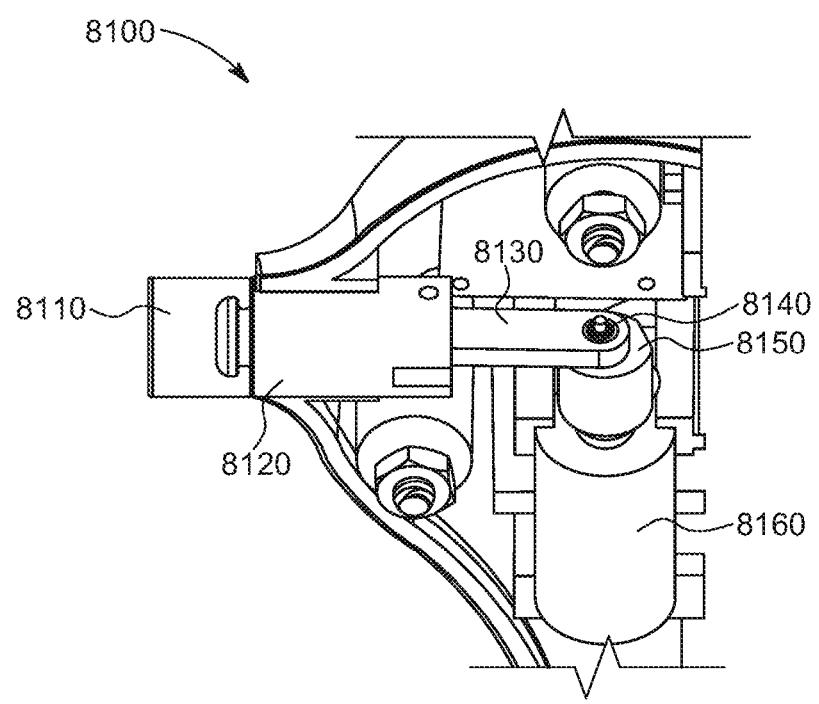
FIG. 18 depicts a device which generates linear vibratory motion to be applied to the skin or eye of a patient.

FIG. 18 depicts an embodiment 8100 in which the end effector interface 8110 moves in a linear direction, actuated by a cam 8150 mechanically connected 8140 to an electric motor 8160. Rotation of the motor linked to the cam 8150 drives a piston 8120 with an end 8110 which also serves as the biocompatible interface with an edge adapted to activate a nerve such as the external nasal nerve. The piston 8120 and biocompatible interface 8110 move at an optimal frequency between 100 and 300 Hz or between 50 Hz and 400 Hz. The cam 8150 can be offset from the central axis 8140 to determine the excursion of the piston (e.g. 1 mm) and interface which then applies force to the skin of the patient and then to the nerve to be stimulated. In some embodiments, a governor is included to ensure that the frequency that is set by the user or pre-determined before delivery to the user is the actual frequency of the piston excursion. For example, in one embodiment, a photodiode or other detector is utilized to detect motion of the electric motor, linkages, or the piston; if the revolutions per minute (RPM) are not as pre-specified, additional current is added or subtracted from the motor. Electronic circuitry is also included which enables the device to record the time of treatment, time between treatments as well as a lock out time in between treatments (e.g. to ensure that the device is not overused or underused). Such data is stored in memory and is downloadable offline to a PC as a record of usage and compliance with the device in real world practice or in a clinical trial setting. The circuit further controls the voltage to ensure a constant power to the motor and constant rotation which can be pre-set or varied by the user.

Figure 19A:
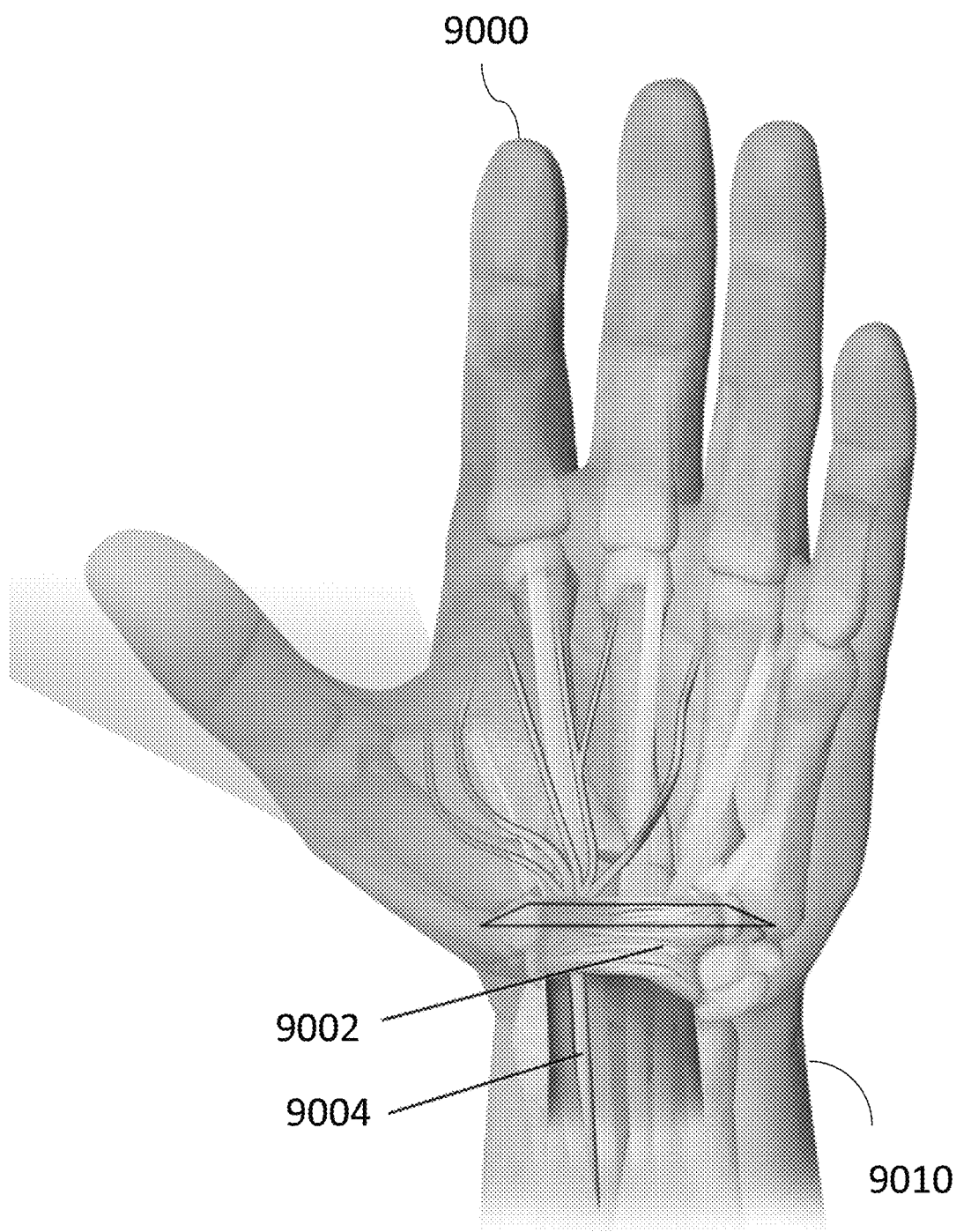
FIG. 19A depicts a carpal ligament and median nerve of a wrist.
Figure 19B:
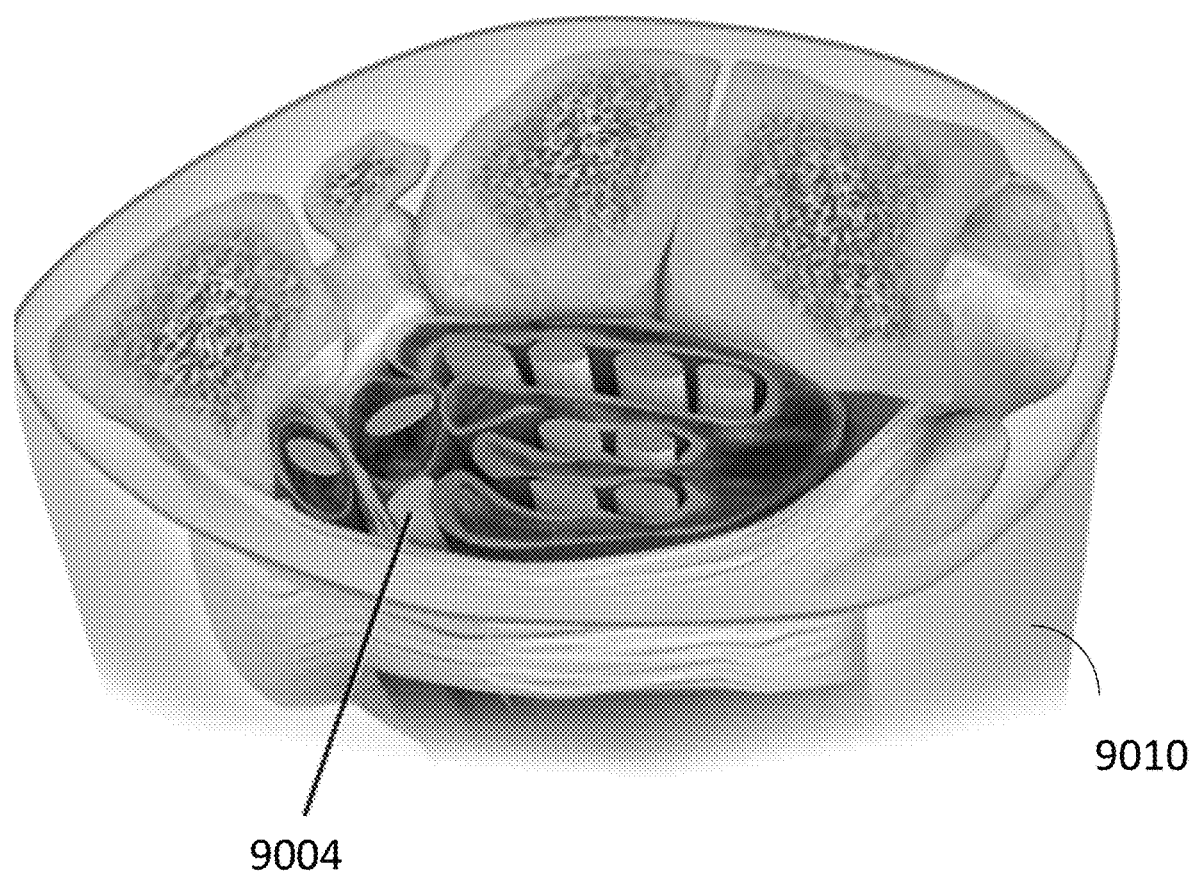
FIG. 19B depicts a transverse section of a wrist.

FIGS. 19A-19B depict a carpal ligament 9002 and median nerve 9004 of a hand 9000 and wrist 9010 of an individual. Carpal Tunnel Syndrome (CTS) is a medical condition due to compression of the median nerve 9004 as it travels through the wrist 9010 at the carpal tunnel. The main symptoms are pain, numbness, and tingling, in the thumb, index finger, middle finger, and the thumb side of the ring fingers. In some embodiments, the devices and methods described herein may be used to stimulate or decompress the median nerve 9004 as it travels through the wrist 9010, for example by providing external ultrasound and/or mechanical vibration to a region adjacent to or on top of the median nerve 9004.

Figure 20:
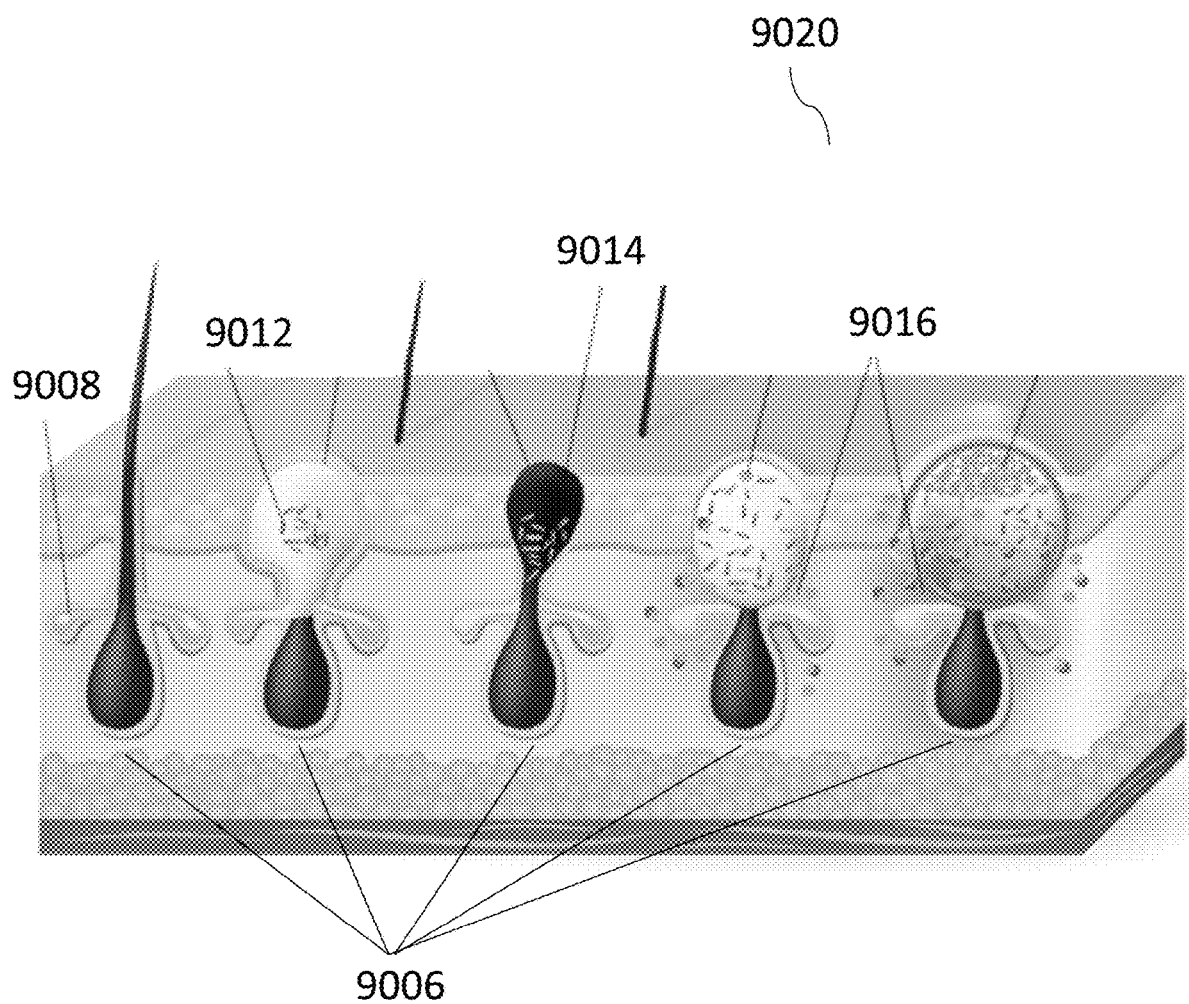
FIG. 20 depicts various mechanisms through which a pore becomes plugged.

FIG. 20 depicts various mechanisms through which a pore on a skin surface 9020 becomes plugged. A skin surface 9020 includes numerous pores 9006, and these pores 9006 can become plugged for any variety of reasons, for example overactive sebaceous glands 9008, bacteria 9012, deadline skin cells 9014, and inflammation 9016, among other mechanisms. In some embodiments, the devices and methods described herein may be used to disrupt the causative agent of the plugged pore, for example by providing external ultrasound and/or mechanical vibration to a region adjacent to or on top of the pore.

Figure 21:
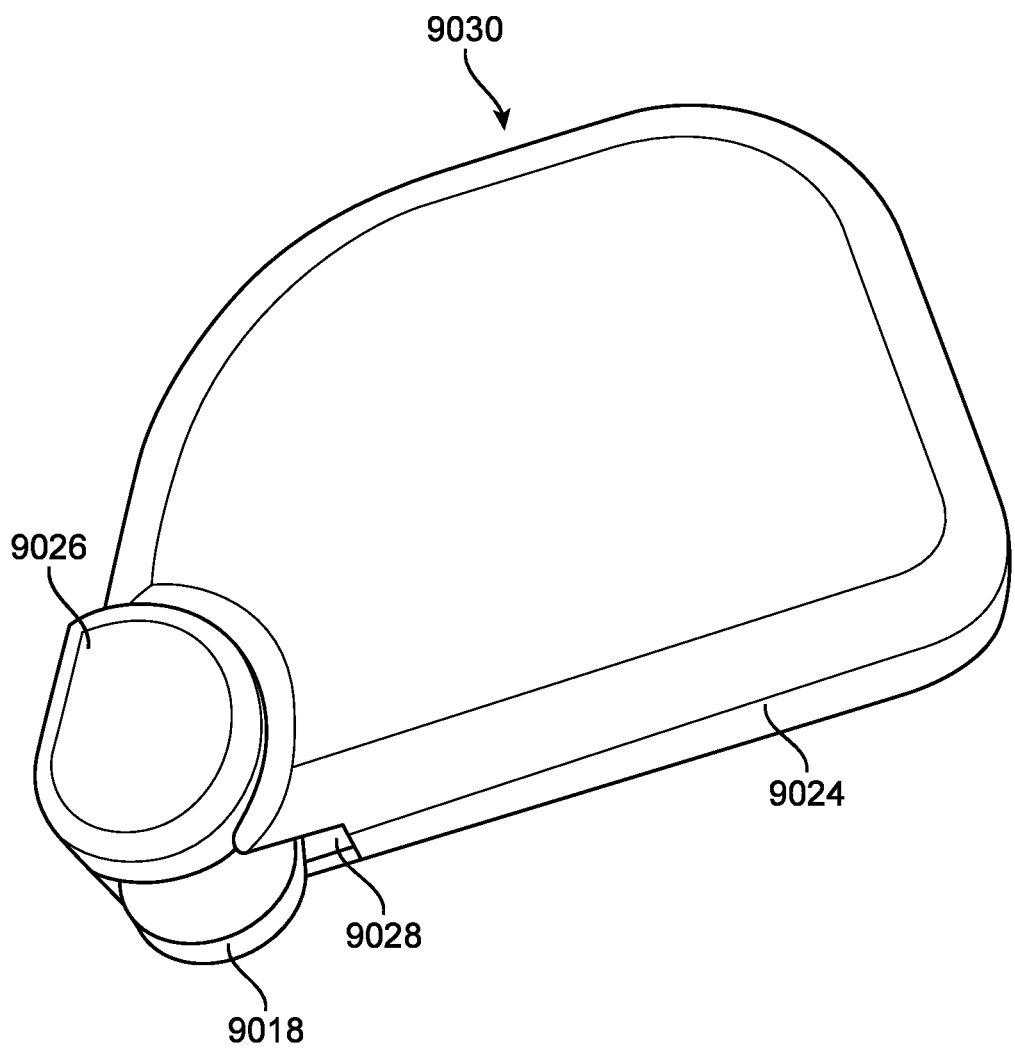
FIG. 21 depicts another embodiment of a device which generates vibratory motion to be applied to the skin or eye of a patient.
Figure 22:
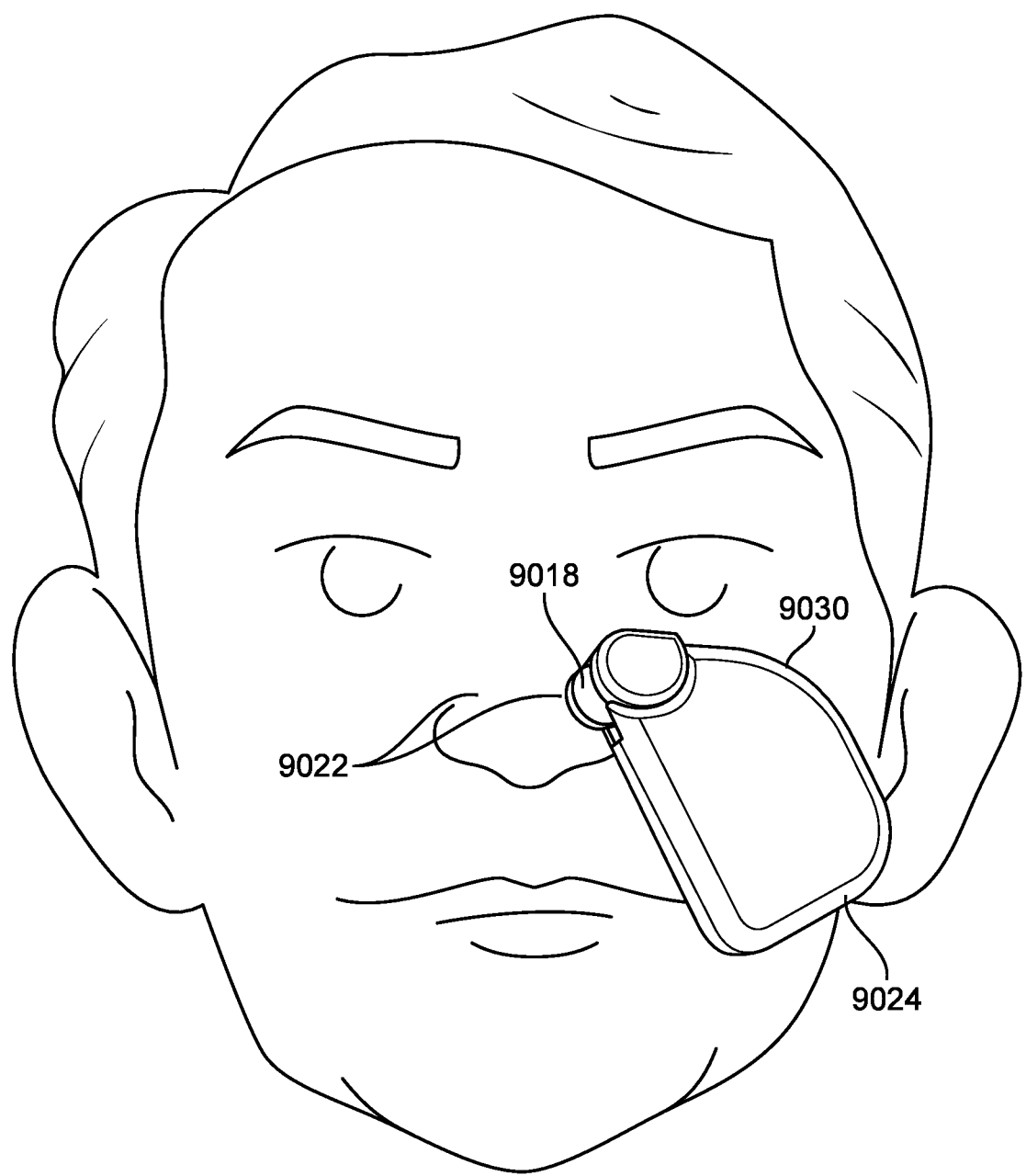
FIG. 22 depicts the device of FIG. 21 being applied to the junction of the nasal bone and the anterior lateral nasal cartilage

Turning to FIG. 21. FIG. 21 depicts another embodiment of a device 9030 which generates substantially one-dimensional vibratory or oscillatory motion to be applied to the skin or eye structure of a patient, as described elsewhere herein. Device 9030 uses effector tip 9018 to provide mechanical vibration to a skin surface or eye structure to stimulate a nerve (e.g., external nasal nerve, median nerve, etc.), inhibit a nerve, treat a skin condition, induce tear production, clear congestion, treat sinusitis, or any other condition known in the art and/or described elsewhere herein. For example, as shown in FIG. 22, oscillation of effector tip 9018 of device 9030 is applied to the junction of the nasal bone and the anterior lateral nasal cartilage where the external nasal nerve 9022 is located. In some embodiments, effector tip 9018 of device 9030 is applied to the external nasal nerve to treat, for example, congestion or sinusitis.

In some embodiments, device 9030 is incorporated into a phone case, for example insertable into a pocket of a case or attachable to a case.

In some embodiments, device 9030 is associated with an application configured to run on another user device, for example a mobile device, smart watch, or computer, to track, monitor, and/or modulate device 9030 performance.

In some embodiments, as shown in FIGS. 21-22, device 9030 includes housing 9024. Housing 9024 functions to at least partially encapsulate or house one or more components of device 9030. For example, effector tip 9018 is partially housed within housing 9024 but also protrudes or extends from housing 9024 via aperture 9028 defined by one or more sidewalls of housing 9024. Alternatively, in some embodiments, device 9030 does not include a housing, but rather includes a plate or surface (e.g., flat or irregular) to which one or more components of device 9030 are coupled, attached, adhered, or otherwise fastened. Further, the housing 9024 of some embodiments includes or is formed of two or more halves or pieces such that the two or more halves or pieces are coupled, attached, bonded, adhered, or otherwise fastened together. The two or more halves may be reversibly coupled or irreversibly coupled. In other embodiments, housing 9024 is formed of a monolithic piece or structure (i.e., consisting of one piece). Housing 9024 includes or is formed of a plastic, for example polyamide, polycarbonate, polyester, polyethylene, polypropylene, polystyrene, polyurethane, polyvinyl chloride, polyvinylidene chloride, acrylonitrile butadiene styrene, or any other plastic or material known in the art. In some embodiments, as shown in FIG. 21, housing 9024 includes a beveled or contoured region 9026 to accommodate effector tip 9018. Contoured region 9026 may be sized and shaped similar to effector tip 9018, for example substantially circular in shape or partially circular in shape (e.g., semi-circular).

Figure 26:
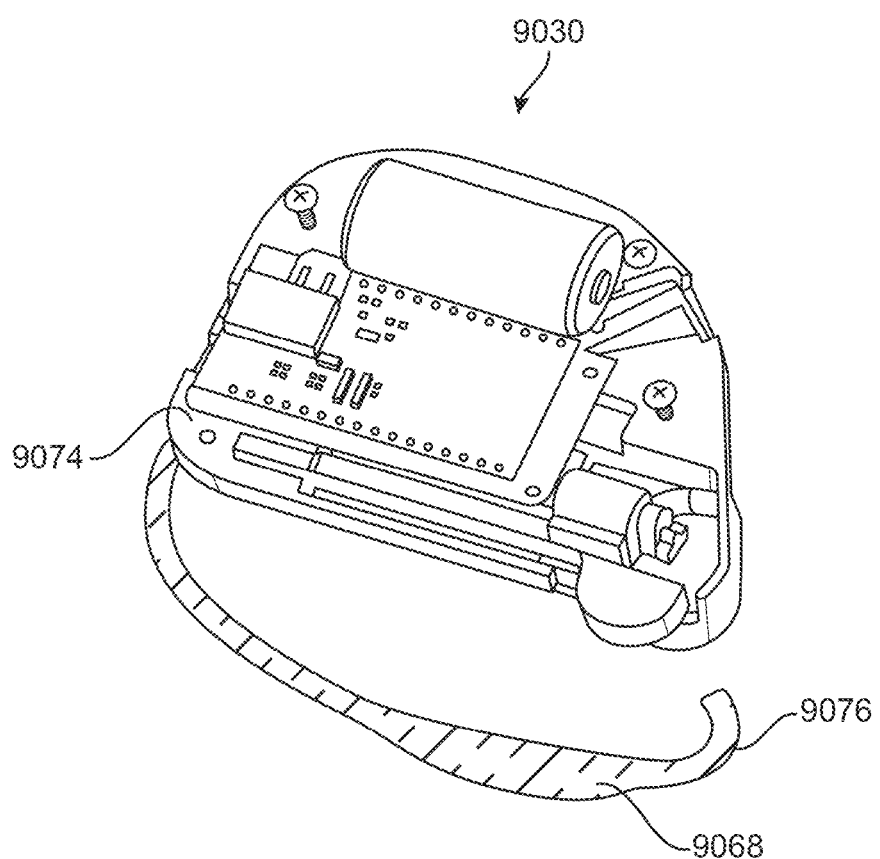
FIG. 26 depicts another embodiment of a device which generates vibratory motion to be applied to an eye structure (e.g., lid, eyeball, etc.) of a patient.

In some embodiments, device 9030 further includes retractor 9068, as shown in FIG. 26. Retractor 9068 functions to retract an eye lid or another body portion or structure of a user so that ultrasound and/or vibration can be applied to a surface of the lid, eye, or an eye structure in or around the eye of the user. A first end 9074 of retractor 9068 may be movably coupled to housing 9024, for example via a hinge, joint, or pivot point. In other embodiments, retractor 9068 is coupled to a plate or other surface to which components of device 9030 are coupled. A second end 9076 of retractor may have a curved shaped with an atraumatic surface for contacting and retracting an eye lid or other body portion or structure of the user.

Figure 23:
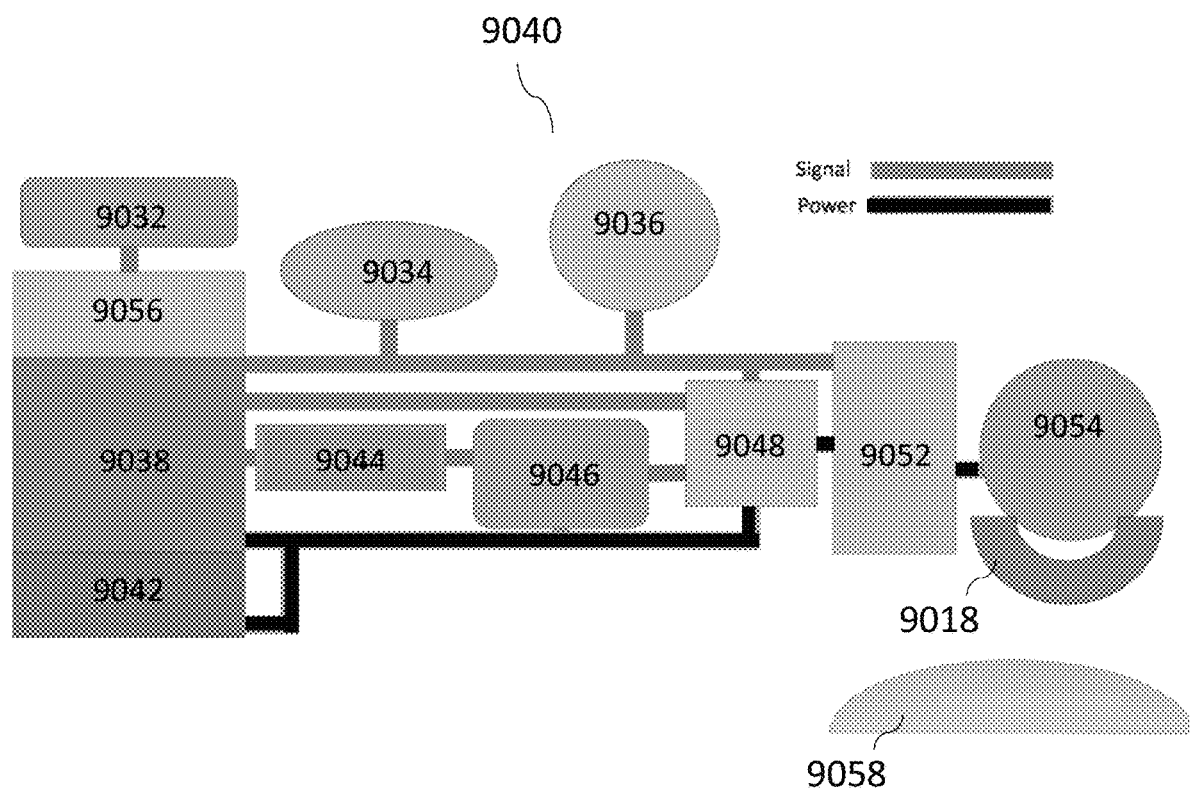
FIG. 23 is a schematic representation of one embodiment of the device of FIG. 21.
Figure 24:
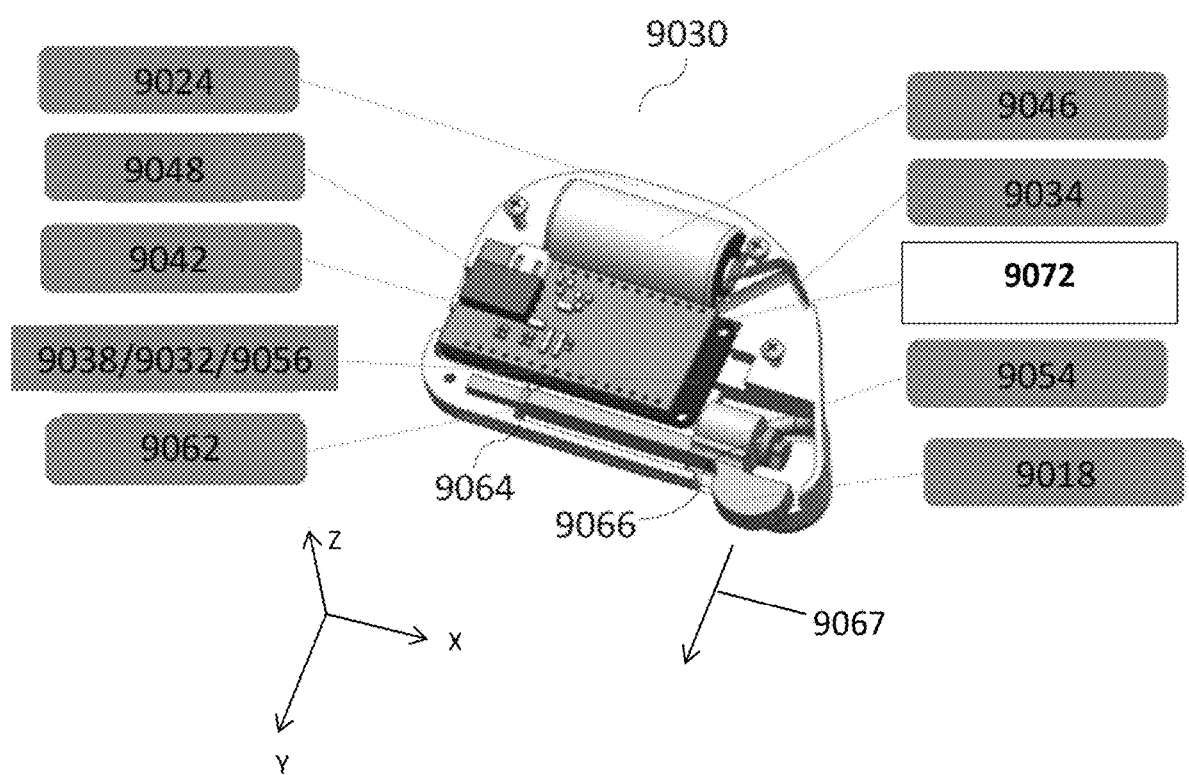
FIG. 24 depicts a cross-sectional view of one embodiment of the device of FIG. 21.

Turning now to FIGS. 23-24. FIG. 23 is a schematic representation of one embodiment of device 9030 of FIG. 21, and FIG. 24 depicts a cross-sectional view of one embodiment of the device of FIG. 21. FIGS. 23-24 shows various components 9040 of device 9030. For example, one or more components of device 9030 may include: memory or storage medium 9032, a power switch 9034, a charge indicator 9036, a controller 9038, a power source charging port 9042, a battery voltage detector 9044, a power source 9046, a direct current (DC)-to-DC converter 9048, a driver 9052, a motor 9054, I/O device 9056 (e.g., non-volatile medium reader/writer), circuit board 9072, effector tip 9018, and cantilever beam 9062. Each component will be described in detail with reference to FIGS. 23-24.

One or more components 9040 described herein are mounted to circuit board 9072, for example a printed circuit board, and electrically interconnected via the circuit board 9072, as shown in FIG. 24.

In some embodiments, as shown in FIGS. 23-24, device 9030 includes storage medium 9032 (e.g., SD card). Storage medium 9032 includes one or more of RAM, ROM, flash memory, EEPROM, a hard disk drive, a solid-state drive, or any other suitable device. In some embodiments, data is stored in non-volatile memory on storage medium 9032; in other embodiments, data is stored in volatile memory on storage medium 9032. Storage medium 9032 stores data, for example use data, battery voltage data, DC-to-DC converter data, etc. In some embodiments, storage medium 9032 is removable from device 9030 to extract and/or analyze use data; in other embodiments, storage medium 9032 is not accessible but rather data is removed from the storage medium through a port (e.g., IEEE 1934, thunderbolt, lightning, etc.) on the device 9030. Data is written to and from storage medium 9032 via I/O device 9056. For example, the I/O device 9056 of some embodiments may be an SD reader/writer.

In some embodiments, as shown in FIGS. 23-24, device 9030 includes power switch 9034 accessible by a user on an exterior of housing 9024 of device 9030. Power switch 9034 activates or deactivates device 9030. Power switch 9034 may be a button, toggle switch, or any other switch known in the art. When power switch 9034 is selected by a user to activate device 9030, driver 9052 (e.g., MOSFET driver) is activated to drive motor 9054 (e.g., eccentric motor) which oscillates cantilever beam 9062 and effector tip 9018, as described in further detail elsewhere herein.

In some embodiments, as shown in FIGS. 23-24, device 9030 includes a power source 9046. In some embodiments, power source 9046 is a rechargeable battery (e.g., Lithium ion battery); in other embodiments, power source 9046 is a disposable battery. In some such embodiments, for example, the device 9030 may be disposed of once the power source 9046 is depleted. Power source 9046 is configured to hold a charge for an extended period of time, for example greater than 1 week, 2 weeks, 3 weeks, or any range or subrange therebetween. During extended periods of non-use, power source 9046 enters into a low power mode, such that the current drops to the nanoamperes (nA) range, for example substantially 200 nA. In some embodiments, device 9030 enters a "deep sleep" mode during extended periods of non-use. Such modes are interrupted by activation or toggling of the power switch 9034. In some embodiments, power source 9046 is configured to maintain a small percentage of charge, for example 5%, 10%, 15%, or 20%, or to not drain power below a certain percentage or threshold so that data may be removed from storage medium 9032 and/or charge indicator 9036 may be illuminated to indicate an energy deficient, power required state of device 9030. In such states, the device 9030 does not function to provide a treatment session to protect a user from an incomplete or inefficient treatment session, for example due to insufficient voltage supplied to the motor.

In some embodiments, as shown in FIGS. 23-24, device 9030 includes a power source charger 9042. Power source charger 9042 is a port for receiving an adapter therein to charge or supply power to power source 9046. In some embodiments, power source charger 9042 is a USB port; in other embodiments, power source charge 9042 is an IEEE 1934, thunderbolt, lightning, etc. port. Alternatively, in some variations, power source charger 9046 is an inductive charging surface or a solar panel.

In some embodiments, as shown in FIGS. 23-24, device 9030 includes a charge indicator 9036 visible on an exterior of housing 9024 of device 9030. Charge indicator 9036 indicates whether device 9030 has sufficient charge to operate device 9030 or whether charging is required before a subsequent treatment cycle. In some embodiments, charge indicator 9036 is a light-emitting diode (LED) or a series of LEDs; in other embodiments, charge indicator 9036 is another type of light-emitting device (e.g., OLED) or color indicator. For example, charge indicator 9036 may fluoresce green or emit a green colored light when power source 9046 is fully charged and yellow, orange, or red when power source 9046 requires power input or recharging. In some embodiments, charge indicator 9036 includes a series of indicators such that in a fully charged state, all indicators are illuminated and/or a pre-determined color, and as charge is used, fewer indicators are illuminated and/or the indicators change color.

In some embodiments, as shown in FIGS. 23-24, the controller 9038 and I/O device 9056 are coupled, via one or more buses, to the storage medium 9032 in order to read information from, and write information to, the storage medium 9032. For example, controller 9038 receives information from one or more of: charge indicator 9036, driver 9052, DC-to-DC converter 9048, power source 9046, battery voltage detector 9044, power source charger 9042, power switch 9034, storage medium 9032, I/O device 9056, and/or any other component. In some embodiments, controller 9038 receives a treatment start time, a power source voltage when motor 9054 is in an off state; a power source voltage when motor 9054 is in an on state; a DC-to-DC converter voltage; a treatment top time; a number of treatment sessions; a treatment duration (e.g., instant, previous, average, median, etc.); or any other relevant information for any one or more of components 9040.

In some variations, device 9030 includes a search mode. For example, a search mode may include one or more presets, each representing a different frequency of effector tip oscillation. Once search mode is activated, for example by a user depressing the effector tip for a pre-determined period of time or selecting a user input element, device 9030 may cycle through each of the pre-sets to allow the user to determine which pre-set is the most effective for achieving the desired therapeutic response. In some embodiments, each pre-set has a slightly higher or lower frequency than the preceding pre-set. Alternatively or additionally, each pre-set has a slightly greater or lesser force than the preceding pre-set. Once the user has identified an ideal pre-set to achieve the desired therapeutic effect, the user selects the desired pre-set, for example by double pressing the effector tip when the device 9030 reaches the pre-set during the cycle, by selecting the pre-set using a user input element (e.g., button, switch, toggle, etc.), or by another method known in the art.

In some embodiments, device 9030 includes one or more intensity modes, for example ranging from soft to intermediate to intense. The user may select an intensity mode using a user input element (e.g., button, toggle, etc.) or, in some embodiments, device 9030 is preconfigured with an intensity based on the desired clinical application.

In some embodiments, device 9030 includes a pressure sensitive switch or a power switch 9034 of device 9030 is a pressure sensitive switch. For example, the pressure sensitive switch senses a continuum of force when pressed lightly to more firmly; this output can then be used to modulate the device's vibratory frequency, amplitude, or both. In some embodiments, multiple switch presses vary an output frequency of device 9030. In some embodiments, multiple switch presses vary an output amplitude of device 9030.

In some embodiments, device 9030 is disposable. For example, a number of treatments (e.g., 100, 200, 300, 400, 500, less than 500, more than 500 treatments, or any range or subrange there between) performed by device 9030 may be read by controller 9038 of the device 9030 and written to storage medium 9032, for example via I/O device 9056, such that the device becomes inactive or is in a permanent off state once a threshold number of treatments has been reached. In other embodiments, device 9030 is reusable. For example, a power source 9046 of device 9030 may be rechargeable and/or replaceable.

In some embodiments, as shown in FIGS. 23-24, device 9030 includes a battery voltage detector 9044. Battery voltage detector 9044 determines whether voltage coming from power source 9046 or power source charger 9042 is in a safe range (i.e., to prevent any current extremes), for example to protect a skin surface or eye of the user from effector tip frequencies or forces that may cause abrasions or ineffective treatment.

In some embodiments, as shown in FIGS. 23-24, device 9030 includes a voltage converter 9048, for example a DC-to-DC converter (e.g., buck-boost converter). Voltage converter 9048 produces an output voltage magnitude that is either greater than or less than the input voltage magnitude. In some embodiments, revolutions per minute (RPM) of the motor 9054 and ultimately a frequency of effector tip 9018 oscillation is increased or decreased when a voltage supplied to the motor 9054 is increased or decreased, respectively. In such embodiments, a manufacturer, healthcare provider of the user, or user of device 9030 can set or control an intensity of effector tip 9018 oscillation by controlling the voltage output by the voltage converter 9048.

In some embodiments, as shown in FIGS. 23-24, device 9030 includes motor 9054. Motor 9054 functions to oscillate effector tip 9018 via, for example, beam 9062, as will be described in further detail elsewhere herein. In some embodiments, motor 9054 is an eccentric rotating mass (ERM) motor using an unbalanced weight or mass 9066 but may also be any other type of motor known in the art, for example a linear resonant actuator. The ERM is configured to cause the beam 9062 to vibrate (oscillate) while the beam 9062 is carrying the motor 9054. In particular, because the beam 9062 is carrying the motor 9054, rotation of the mass 9066 by the motor 9054 will cause the beam 9062 together with the motor 9054 to oscillate in a desired direction, for example perpendicular to a surface 9058 of tissue. In some embodiments, the motor 9054 may be configured to rotate the ERM at a certain frequency that maximizes a vibrational amplitude of the effector tip 9018. In other embodiments, the motor 9054 may be configured to rotate the ERM at other frequencies, which do not necessarily maximize a vibrational amplitude of the effector tip 9018. Also, in some embodiments, the motor 9054 is configured to rotate the mass 9066 at a frequency that corresponds with the natural frequency of the beam 9062 (with the mass of the motor 9054). For example, the motor 9054 may rotate the mass 9066 at a frequency that is equal to, or near the natural frequency fn of the beam 9062 (with the mass of the motor 9054)—e.g., fn±0.1fn. In other embodiments, the motor 9054 may be configured to rotate the mass 9066 at other frequencies that may not correspond with the natural frequency of the beam 9062 (with the mass of the motor 9054). In some embodiments, device 9030 includes a modular motor that can be changed or altered by a user or prescribing health professional to better match a frequency or amplitude of device output to a user's needs.

In some embodiments, a majority of a length of the beam 9062 may have a cross section shaped with a certain orientation to ensure that the beam 9062 will undergoing bending action in a desired direction in response to the turning of the eccentric mass 9066 by the motor 9054. For example, the beam 9062 may have a rectangular cross section having a long side and a short side. The cross section may be oriented so that the long side of the rectangular cross section is perpendicular to a desired bending direction 9067 of the beam 9062 (e.g., is parallel to the Z-axis), and so that the short side is parallel to the desired bending direction (e.g., parallel to the Y-axis). This configuration orientates the beam 9062 so that its weaker bending stiffness is associated with bending action within the X-Y plane, and its stronger bending stiffness is associated with bending action within the X-Z plane. As a result, the beam 9062 is more easily bend within the X-Y plane than within the X-Z plane. In other embodiments, the beam 9062 may have other cross sectional shapes, such as an elliptical shape, a T-shape, or any of other shapes. Also, in some embodiments, a cross sectional moment of inertia of a cross section of the beam 9062 about the Z-axis is less than a cross sectional moment of inertia of the cross section of the beam 9062 about the Y-axis. This feature also provides an orientation of the beam 9062 so that its weaker bending stiffness is associated with bending action within the X-Y plane, and its stronger bending stiffness is associated with bending action within the X-Z plane. As a result the beam 9062 is more easily bend within the X-Y plane than within the X-Z plane.

Also, in some embodiments, electrical wires from the motor 9054 may be attached to the beam 9062 to avoid any relative movement between the beam 9062 and the electrical wires. For example, the beam 9062 may have one or more openings or frames for allowing the electrical wires to extend therethrough, thereby allowing the beam 9062 to carry the electrical wires, and allowing the beam 9062 and the electrical wires to move (vibrate) together. In some embodiments, a majority of a length of the electrical wires, or portion(s) of the electrical wires, may be coupled to an external surface of the beam 9062. In other embodiments, a majority of a length of the electrical wires, or portion(s) of the electrical wires, may be coupled internally within the beam 9062. In other embodiments, the electrical wires from the motor 9054 may not be attached to the beam 9062.

In the illustrated embodiments, the motor 9054 is attached to the beam 9062 so that the motor 9054 and the beam 9062 can move (e.g., vibrate) together in response to the motor 9054 turning an eccentric rotating mass 9066 attached to a shaft of the motor 9054. This feature is advantageous because it allows the device 9030 to operate more quietly. In particular, because the motor 9054 is configured to cause the beam 9062 to vibrate together with the motor 9054 without using any mechanical linkage that moves and touches against the beam 9062, there is no noise generated from any moving part touching the beam 9062. Also, for this same reason, the chance of the beam 9062 having wear and tear and having mechanical failure is substantially reduced, and the device 9030 has a relatively longer lifetime (at least compared to the embodiment of FIG. 18 that uses a reciprocal motor 9054, or to a technique that involves the motor moving the beam via mechanical linkage that moves and touches the beam).

In other embodiments, instead of having the motor 9054 immovably attached to the beam 9062, the device 9030 may include a motor that is immovably attached to the housing or to a frame within the housing. In such cases, the motor 9054 is configured to move the beam 9062 in an oscillatory manner via mechanical linkage, and the beam 9062 is configured to move relative to the motor 9054.

In some embodiments, device 9030 may include two or more motors acting (e.g., causing vibration) on a beam. The two or motors may be arranged orthogonally or at angles with respect to one another to provide vibratory control in multiple planes of motion.

In some embodiments, device 9030 includes two or more motors aligned in the same plane but spinning in opposite directions amplifying motion in a primary direction but canceling motion in a secondary lateral direction. In some embodiments, device 9030 includes two or motors acting on a beam to provide increased vibratory amplitude in a primary direction of motion.

In some embodiments, device 9030 includes a transmitter or transceiver, for example to communicate data to nearby devices including cell phones, computers, and smart watches.

In some embodiments, device 9030 is equipped with a biometric reader, for example a fingerprint or eye scanner or facial recognition software. Biometric reader may be configured to limit device 9030 use to one or more users.

In some embodiments, device 9030 includes electronics, software, and/or one or more parameters that limit device 9030 use to a prescribed number of treatments.

In some embodiments, device 9030 includes a display configured to display use data, a treatment duration, a treatment frequency, a treatment history, a prescribed treatment regimen, a frequency of vibration, an amplitude of vibration, etc. or to prompt a user to apply a treatment using device 9030.

In some embodiments, device 9030 includes a visual, auditory, and/or haptic modality for alerting a user that it is time to use device 9030 for a treatment session and/or that the prescribed duration of use has been achieved.

Turning now to effector tip 9018 and beam 9062. Effector tip 9018 functions as the treatment surface, for example for contacting a skin surface or an eye structure of a user. In some embodiments, effector tip 9018 includes or is formed of a plastic, for example acrylonitrile butadiene styrene, but may also be any other plastic or material known in the art. Effector tip 9018 is shaped and configured to have smooth contours to limit unintended abrasions during use but to elicit effective treatment. In some embodiments, a durometer of the effector tip 9018 is between 20 A to 80 A, 30 A to 70 A, 40 A to 60 A, 40 A to 50 A, 50 A to 60 A, 45 A to 55 A, or any range or subrange therebetween. The durometer of effector tip 9018 is configured to induce effective treatment while limiting unintended effects, such as abrasions.

In some embodiments, effector tip 9018 is replaceable and/or can be equipped with elastomers of varying stiffness to better meet the comfort needs of each user.

In some embodiments, effector tip 9018 includes a conductive heating element, for example a resistive coil to heat tissue while in operation. In other embodiments, effector tip 9018 includes a radiative heating element, for example an infrared light to heat tissue while in operation. The radiative heating element of some embodiments radiates electromagnetic energy between 400-1000 nm wavelength at effector tip 9018.

Effector tip 9018 is coupled to beam 9062 (e.g., two components coupled together or as a monolithic component) and oscillates as result of motor 9054 movement via contact with beam 9062 and effector tip 9018. The oscillation is dictated by a combination of the motor rotation and the weight and geometry of beam 9062 and the reactions at coupling element 9064. A stiff coupling element 9064 will result in a lower frequency whereas a loose coupling element 9064 will result in a higher frequency but also less force per revolution on a surface of the patient. The effector tip 9018 oscillates with a substantially fixed amplitude in air. For example, the substantially fixed amplitude is between about 0.1 and 2 mm, 0.2 mm and 1.8 mm, 0.25 mm and 2 mm, 0.25 mm and 1.5 mm, or any range or subrange therebetween. In some embodiments, the fixed amplitude is substantially 1 mm, greater than 0.1 mm, greater than 0.2 mm, less than 2 mm, less than 1.75 mm, less than 1.5 mm, or any value, range, or subrange therebetween.

The effector tip 9018 oscillates with a force, such force being related to a natural frequency of beam 9062 and a frequency of oscillation of motor 9054, as described in more detail elsewhere herein. In some embodiments, the effector tip oscillates with a force of substantially 0.5 N to 5 N, 1 N to 3 N, less than 5 N, less than 4 N, less than 3 N, greater than 0.5 N, greater than 0.75 N, greater than 1 N, or any value, range, or subrange therebetween.

The effector tip 9018 oscillates with a frequency, such frequency being related to a natural frequency of beam 9062 and a frequency of oscillation of motor 9054, as described in more detail elsewhere herein. In some embodiments, a frequency of oscillation of the effector tip 9018 is substantially 5 Hz to 500 Hz, 25 Hz to 400 Hz, 50 Hz to 300 Hz, 50 Hz to 250 Hz, greater than 25 Hz, greater than 50 Hz, less than 500 Hz, less than 300 Hz, less than 250 Hz, or any value, range, or subrange therebetween.

In some embodiments, a frequency, force, and/or amplitude of effector tip 9018 oscillation is dampened by an amount of force a user applies to the device 9030 against a surface 9058; in other embodiments, a frequency or force of effector tip 9018 oscillation is maintained regardless of an amount of force a user applies to the effector tip 9018 against a surface 9058, for example as shown in FIG. 18. For example, a user of device 9030 controls an intensity of a treatment session by controlling an output force and/or frequency of oscillation of effector tip 9018. The beam 9062 bends when a force is applied to the effector tip 9018, such that bending beam 9062 slows motor 9054 and reduces effector tip 9018 oscillation. Such force and/or frequency of effector tip 9018 is controlled by the user applying force to the effector tip 9018 during a treatment session. For example, a frequency of oscillation of the effector tip 9018 is dampable when a force of substantially 0.5 N, 0.6 N, 0.7 N, 0.8 N, 0.9 N, 1 N, 1.1 N, 1.2 N, 1.3 N, 1.4 N, 1.5 N, greater than 0.75 N, greater than 0.8 N, greater than 0.9 N, less than 1.2 N, less than 1.1 N, or any force value in between is applied to effector tip 9018. Correspondingly, the amplitude of oscillation of effector tip 9018 is dampable when a force of substantially 0.5 N, 1 N, 1.1 N, 1.2 N, 1.3 N, 1.4 N, 1.5 N, 1.6 N, 1.7 N, 1.8 N, 1.9 N, 2 N, 2.1 N, 2.2 N, 2.3 N, 2.4 N, 2.5 N, greater than 1.5 N, less than 2.5 N, or any force value therebetween is applied to effector tip 9018. The dampable nature of effector tip 9018 is critical for the atraumatic use of device 9030. In embodiments where effector tip 9018 is not dampable, a user applying a greater force than is required for effective treatment may result in abrasions on the skin surface or eye structure because a frequency or amplitude of oscillation of effector tip 9018 would not adjust in response to the applied force.

In some embodiments, device 9030 includes a motion sensor, for example an accelerometer, gyroscope, inertial sensor, etc. to measure vibratory output that may be fed into the device's control loop.

Figure 25:
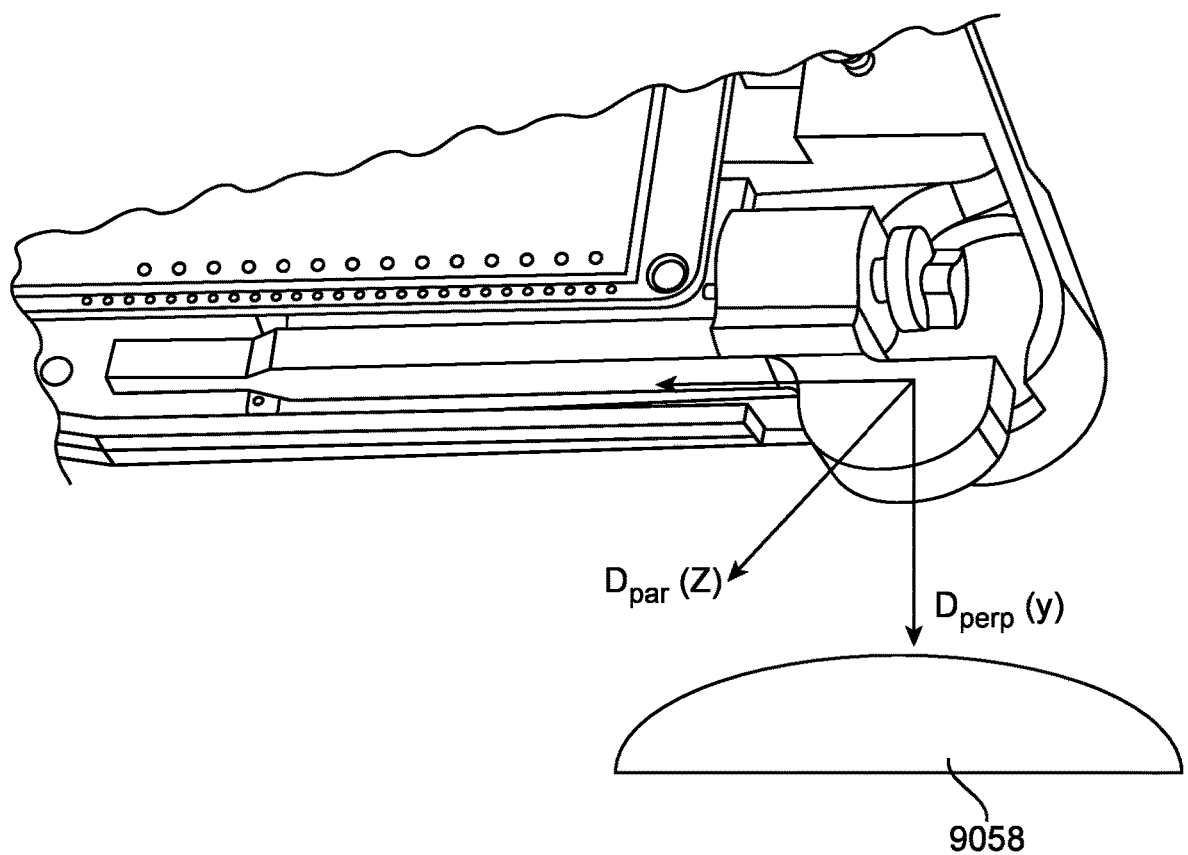
FIG. 25 depicts various dimensions of the device of FIG. 21.

In some embodiments, as shown in FIG. 24, device 9030 includes beam 9062 coupled to effector tip 9018. Beam 9062 is coupled to device 9030 via a coupling element 9064 (e.g., a bracket, joint, fastener, pivot point, hinge, etc.). Coupling element 9064 couples beam 9062 to housing 9024 or to a plate or surface to which the components are coupled. Beam 9062 functions to maintain oscillation of effector tip 9018 in substantially one dimension, for example perpendicular to a surface. In some embodiments, there is additional motion parallel to the surface. The beam 9062 constrains oscillation of the motor into substantially one direction (i.e., perpendicular to surface $D_{perp}$ in a direction y), as shown in FIG. 25, but, in some embodiments, there is also movement in a plane parallel to the surface $D_{par}$ in a direction z. In some embodiments, a ratio of movement parallel $D_{par}$ to the surface versus perpendicular $D_{perp}$ to the surface is 1:2, 1:4, 1:8, 1:12, 1:16, or any ratio therebetween. For example, for every one movement parallel to the surface there are four movements perpendicular to the surface. In some embodiments, movement in one direction parallel to the surface is less than 1 mm; in other embodiments, movement in one direction parallel to the surface is substantially 1 mm, 1-1.5 mm, 1.5-2 mm, 2-2.5 mm, 2.5-3 mm, less than 5 mm, or any value, range, or subrange therebetween.

In some embodiments, device 9030 includes a modular beam that can be changed or altered by a user or prescribing health professional to better match a frequency or amplitude of device output to a user's needs.

In some embodiments, device 9030 includes two or more beams. In some embodiments, the two or more beams are oriented to simultaneously stimulate tear production in left and right eye, for example by stimulating the external nasal nerve on both the right and left side of a nose of a user.

Further, the geometry of the beam 9062 results in beam 9062 having a natural frequency at substantially 200 Hz (e.g., 200 Hz±20 Hz); the oscillation frequency of the motor 9054 is set to substantially the natural frequency of beam 9062 or the natural frequency of beam 9062 plus coupling element 9064, so that the beam 9062 and the motor 9054 work synergistically. In some embodiments, the dimensions of beam 9062 are 4 mm wide, 3 mm deep and 50 mm in length. In other embodiments, the dimensions of beam 9062 range from 2-8 mm wide, 1-6 mm deep, and 25-75 mm in length, or any range or subrange therebetween. For example, since beam 9062 is substantially constrained to rotation in a plane, it is sufficient to consider its moment of inertia about an axis perpendicular to the plane. The following equation (1) may be used:

$$I = bd^3/12 \quad (1)$$

where I is the moment of inertia (angular mass or rotational inertia), b is the width of beam 9062, and d is the depth of beam 9062.

Figure 31:
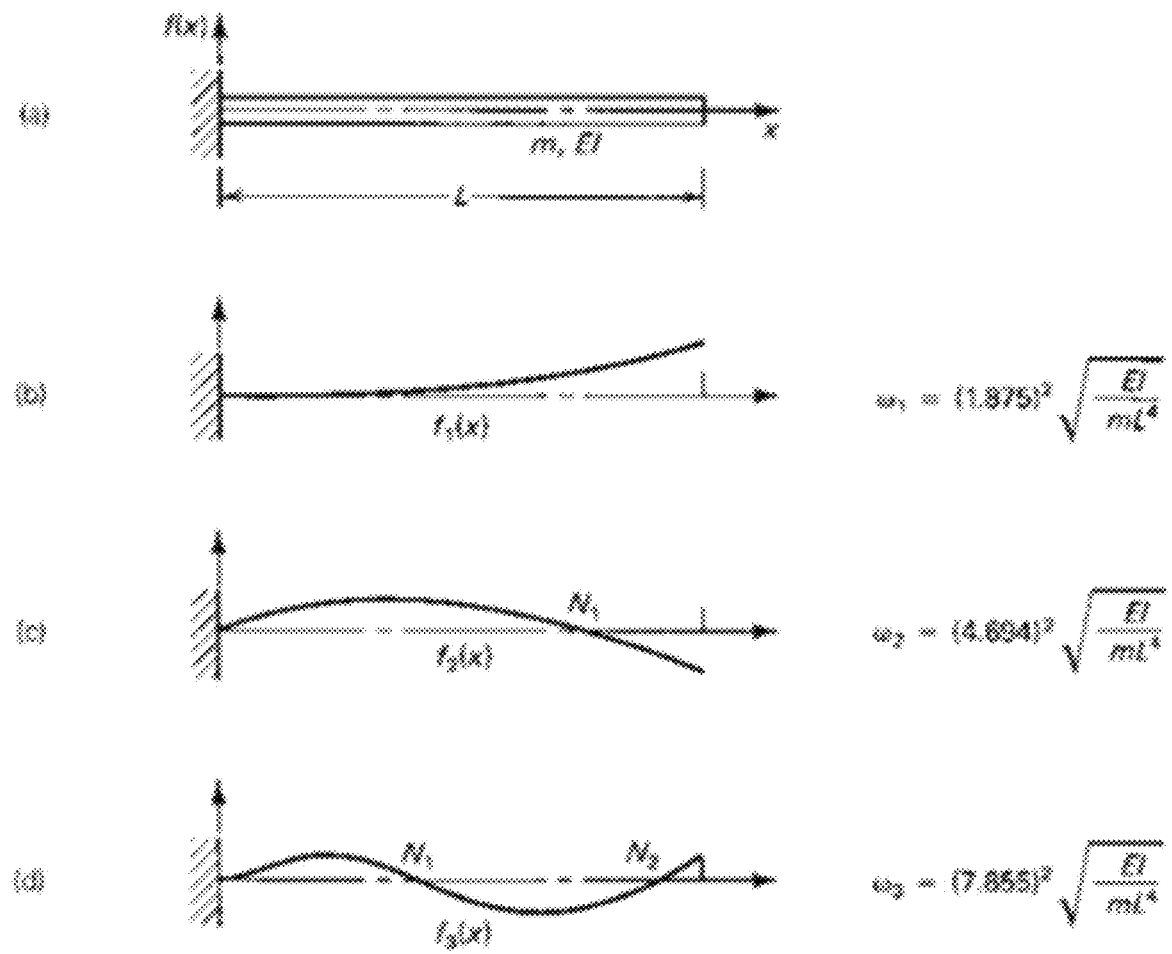
FIG. 31 depicts equations for calculating natural frequency of a cantilever beam.

A natural frequency of beam 9062 is calculated, for example, according to the equations (a) through (d) in FIG. 31, in which:

m is a mass per unit length of the beam 9062,

L is the distance from the fixed end of beam 9062,

E is the modulus of rigidity of the material of beam 9062,

I is the moment of inertia (calculated in (1)) of beam 9062,

ω is the natural frequency ($\omega_1$, $\omega_2$, $\omega_3$; first, second, third natural frequency, respectively) of beam 9062, f(x) is displacement in y direction at distance x from fixed end of beam 9062, and 1.875, 4.694, and 7.855 are constants $\alpha_n$.

The calculated or determined natural frequency of beam 9062 or beam 9062 plus coupling element 9064 can then be used to tune a frequency of oscillation of motor 9054. As will be described in further detail in connection with FIGS. 27-28B, even small changes or adjustments in the dimensions or geometry of beam 9062 can have profound effects on the natural frequency of beam 9062 and thus the frequency to which motor 9054 is tuned.

In some embodiments, oscillation frequency based on beam dimensions is simulated to account for a shape of beam 9062 and a motor 9054 mounted to the end of beam 9062 to model the complex geometries of beam 9062 and heterogenous material properties of beam 9062.

Figure 27:
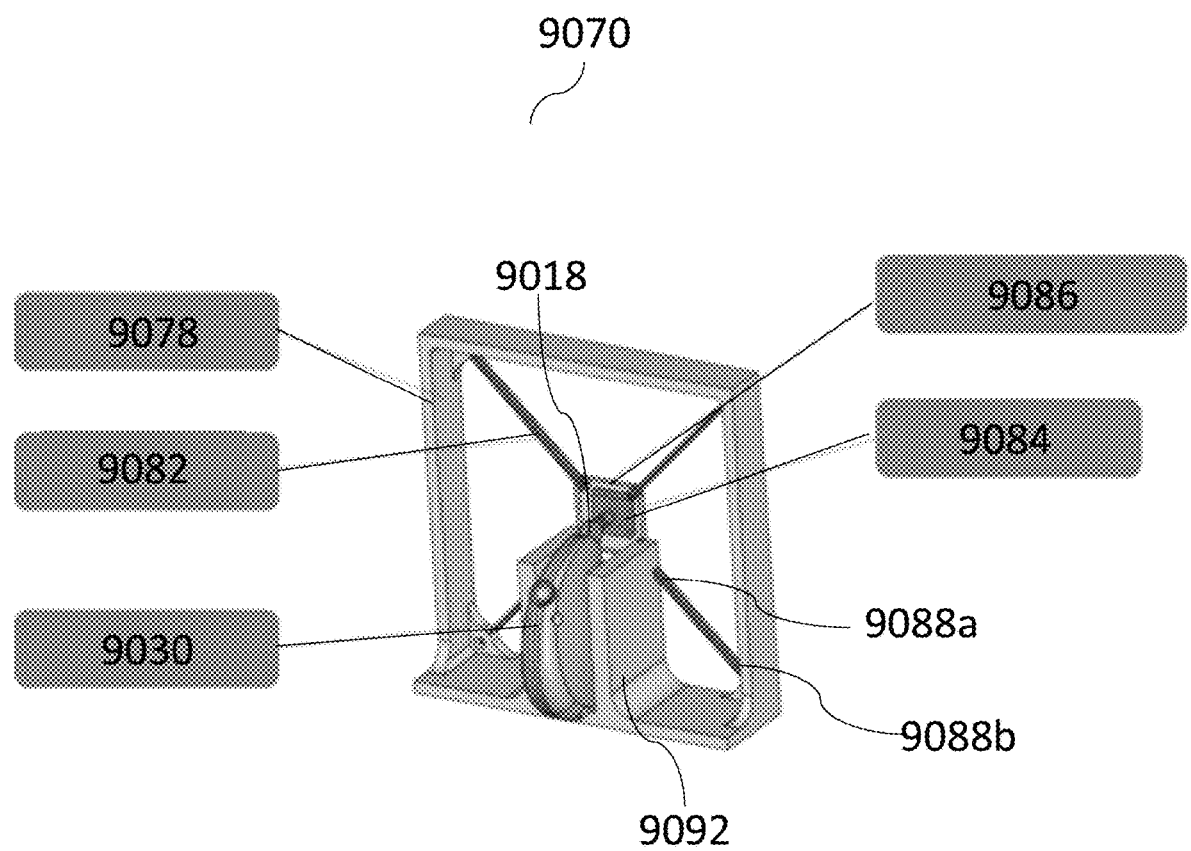
FIG. 27 depicts a test fixture for testing a device which generates vibratory motion.

Turning now to FIG. 27. FIG. 27 depicts a test fixture 9070 for testing a device, for example device 9030 or any device described elsewhere herein, to determine a force output of device 9030. Text fixture 9070 includes a frame 9078 including holder 9092, two or more members 9082, sensor 9084, and plate 9086. The two or more members 9082 are coupled to plate 9086 at a first end 9088a and to frame 9078 at a second end 9088b. Members 9082 suspend plate 9086 in frame 9078, as shown in FIG. 27. In some embodiments, members 9082 are elastic; in other embodiments, members 9082 are more rigid or inflexible. The material of members 9082 is dictated by a type of test to be conducted with test fixture 9070. Device 9030, or any device described elsewhere herein, rests in holder 9092 of frame 9078 during testing. Plate 9086 is a contact surface for effector tip 9018 during testing and includes one or sensors 9084. In some embodiments, sensor 9084 is a motion sensor (e.g., accelerometer, gyroscope, etc.); in other embodiments, sensor 9084 is a force sensor, pressure sensor, camera, temperature sensor, touch sensor, proximity sensor, optical sensor, colorimeter, tactile sensor, or any other sensor known in the art.

Figure 28A:
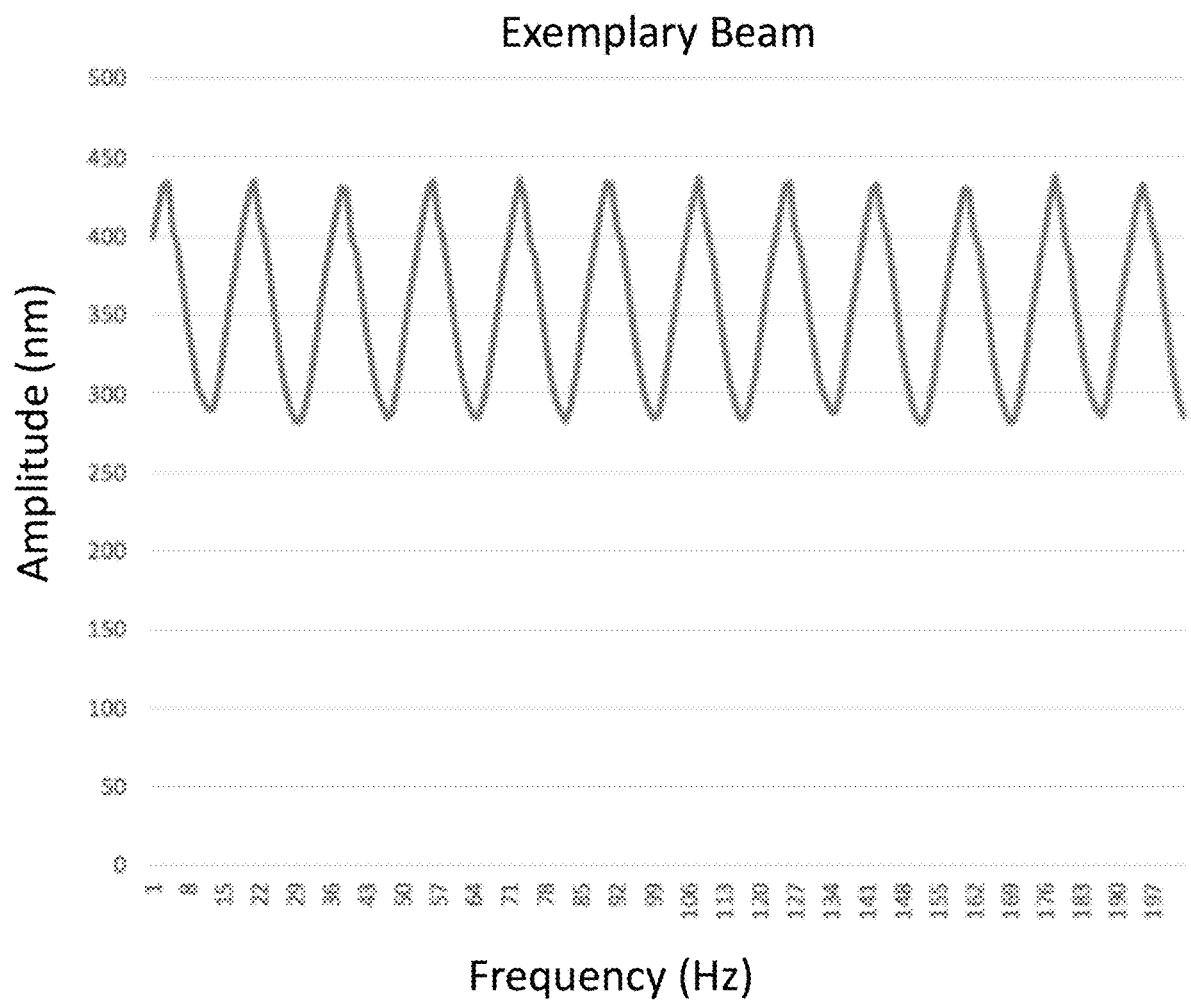
FIG. 28A depicts a frequency and amplitude of an effector tip of a device with one embodiment of a cantilever beam.
Figure 28B:
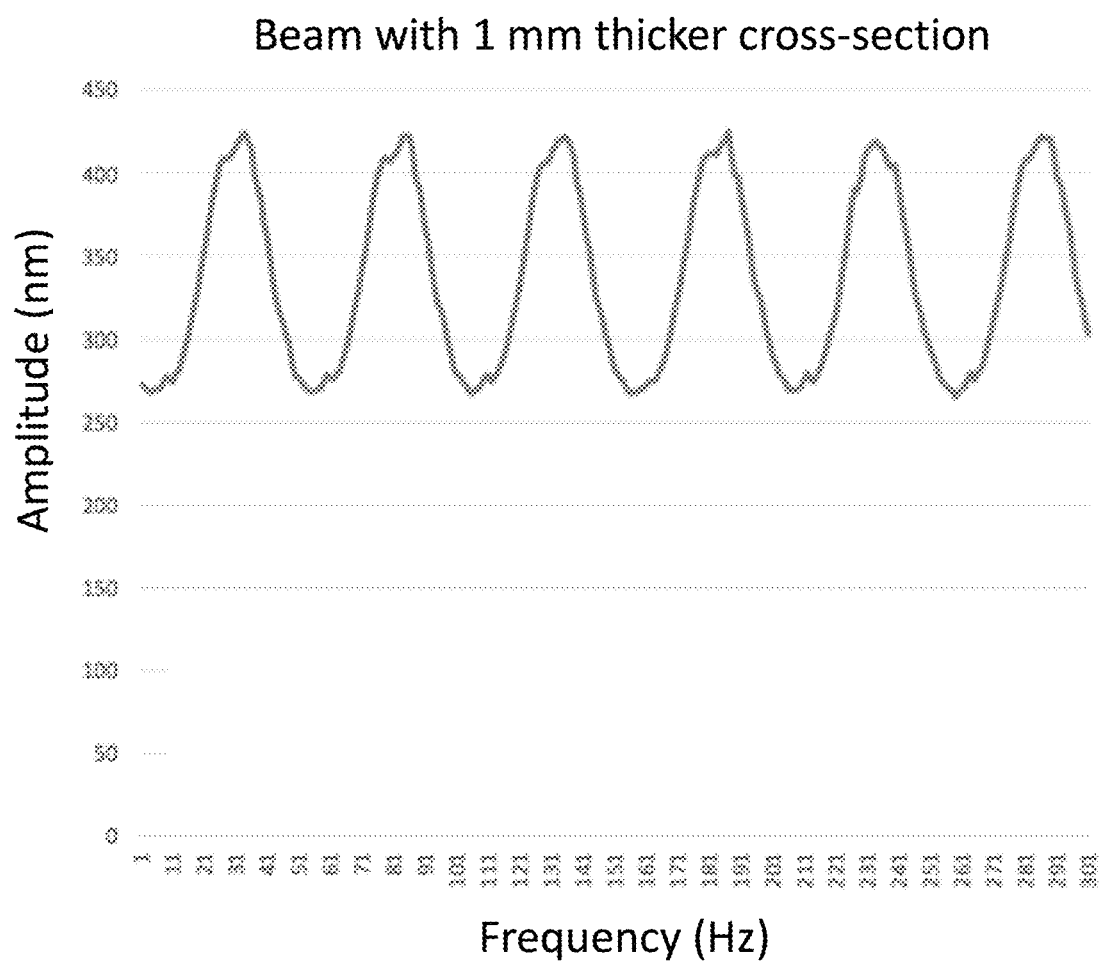
FIG. 28B depicts a frequency and amplitude of an effector tip of a device with another embodiment of a cantilever beam.

In the example shown in FIGS. 28A-28B, effector tip 9018 of device 9030 contacts sensor 9084, an accelerometer, on plate 9086 of text fixture 9070. The sensor 9084 measures the dynamic acceleration of effector tip 9018 as a voltage, which can then be used to calculate or estimate a force exerted by effector tip 9018. Since plate 9086 and sensor 9084 have a known mass, an output force of effector tip 9018 can be estimated using the following equation (2):

$$F = m*a \quad (2)$$

where F is the output force of effector tip 9018, m is a combined mass of plate 9086 and sensor 9084, and a is the acceleration as measured by sensor 9084.

The dynamic acceleration, shown as amplitude vs. frequency, of exemplary beam 9062 of device 9030 is shown in FIG. 28A and a beam with a thicker cross-section is shown in FIG. 28B. As shown in FIG. 28A, the geometry of the beam was selected to have a desired output frequency (Hz) and amplitude (mm), for example substantially 270 Hz and 148 mm, to produce a desired therapeutic effect elicited by effector tip 9018 of device 9030. In contrast, changing the geometry of the beam, even by 1 mm, drastically changes a frequency of effector tip oscillation. For example, as shown in FIG. 28B, increasing a thickness of the beam cross-section by 1 mm drastically reduced a frequency of effector tip oscillation (from substantially 230 Hz to substantially 78 Hz).

Using test fixture 9070 for commercially available devices reveals that these devices do not result in the same motion, frequency, amplitude, and/or force as device 9030. For example, commercially available back massage devices, Sonicare® devices, or devices using reciprocal motors to elicit beam movement do not output the correct motion or skin interface, nor the correct frequency, force, and/or amplitude to elicit a beneficial, atraumatic, and/or quiet therapeutic effect. As a consequence, these other commercially available devices do not deliver the therapeutic effect of inducing tears or providing relief from congestion, for example rhinosinusitis.

TABLE 1

Function and Efficacy of Commercially Available Devices

| Device | Frequency (Hz) | Force Output | Clinical Efficacy | Shape of interface |
|---|---|---|---|---|
| iTEARgen1 | 180 | 180 | Minimal | 90 degree angle |
| iTEARgen2 | 270 | 180 | Yes | 90 degree angle |
| Sonicare | 263 | 85 | Minimal | Smooth |
| Dr. Johnson | 130 | 141 | No | Smooth/Rounded |
| Wahl Deep Tissue | 90 | 95 | No | Smooth/Rounded |
| Evolved | 127 | 180 | No | Smooth/Rounded |
| First Time | 141 | 80 | No | Smooth/Rounded |

Table 1 above relates force and frequency measured by the test fixture 9070 to clinical efficacy in a selection of commercially available devices. The tips of the devices and the shape of the tips were chosen from a larger group of commercially available devices due to their potential to activate nerves related to lacrimation and nasal decongestion. The clinical efficacy is an increase in tearing from the lacrimal gland and a decrease in nasal congestion. As shown in Table 1, very few devices that were tested were clinically effective. This lack of clinical efficacy is likely due to the shape of the interface and the combined force and frequency output of the effector tip.

As shown in Table 1, iTEARgen1 was modestly effective in stimulating tear production and iTEARgen2 was more effective than iTEARgen1, producing the desired clinical effect in over 99% of patients. The frequency, force, and movement of iTEARgen2 makes it a significantly improved device compared to iTEARgen1. However, both are significantly better than commercially available massager devices which serve other purposes. The other devices (i.e., Sonicare, Dr. Johnson, Walh Deep Tissue, Evolved, First Time) in Table 1 are commercial devices sold as massagers for various body regions.

FIGS. 29A-29B depict various views of an effector tip, similar to the effector tip of iTEARgen1 and gen2, which was successful in clinical efficacy. As shown in FIGS. 29A-29B, the effector tip has sharp, 90 degree edges. In contrast, FIGS. 30A-30B depict various views of an end effector, which was clinically ineffective. As shown in FIGS. 30A-30B, the effector tip has rounded or smooth surfaces. As described herein with respect to device 9030 of FIGS. 21-26 and in direct contrast to the results presented in Table 1, the effector tip 9018 of device 9030 achieves clinical efficacy while also having a narrow smooth surface with defined edges on the effector tip 9018. Such efficacy is due in part to the shape and composition of the effector tip 9018 but also the unique mechanisms (e.g., eccentric motor, beam, etc.) of device 9030 that are used to induce effector tip 9018 vibration/oscillation.

There are additional differences between the commercially available devices which do not have an indication for dry eye and which do not work for dry eye. For example, effector tips on the commercially available devices do not move independently from the housing on the device. Such an arrangement is necessarily inefficient because the entire housing vibrates as opposed to all the force being delivered to the interface by the effector tip. In other words, the pressure is lower over the larger surface of the device which is less effective than higher pressure over the smaller surface area of the effector tip. In the currently described device 9030, the effector tip 9018 moves independently from the housing 9024, oscillating in and out of the housing or substantially outside the housing to apply its therapeutic benefit and maximizing the force applied to the patient's external nasal nerve. The motor 9054 is inside the housing 9024 and communicates with the effector tip 9018 through a physical connection which might be a mechanical linkage, an electromagnetic coupling, or a direct connection to the effector tip 9018. The housing 9024 is merely required so that the operator can hold the device 9030.

In one or more embodiments described herein, the device may be designed with low cost and form factor, which encourages compliance and facilitates its utilization.

As used in the description and claims, the singular form "a", "an" and "the" include both singular and plural references unless the context clearly dictates otherwise. For example, the term "effector" may include, and is contemplated to include, a plurality of effector tips. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range (e.g., to define a length or pressure), indicates approximations which may vary by (+) or (−) 10%, 5%, 1% 0.1%, or 0%. All numerical ranges provided herein are inclusive of the stated start and end numbers. The term "substantially" indicates mostly (i.e., greater than 50%) or essentially all of a device, substance, composition, a metric, a value, a parameter, etc.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a system or method consisting essentially of the elements as defined herein would not exclude other materials, features, or steps that do not materially affect the basic and novel characteristic(s) of the claimed disclosure. "Consisting of" shall mean that the devices, systems, and methods include the recited elements and exclude anything more than a trivial or inconsequential element or step. Embodiments defined by each of these transitional terms are within the scope of this disclosure.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

Although particular embodiments have been shown and described, it will be understood that it is not intended to limit the claimed inventions to the preferred embodiments, and it will be obvious to those skilled in the art that various changes and modifications may be made without department from the spirit and scope of the claimed inventions. The specification and drawings are, accordingly, to be regarded in an illustrative rather than restrictive sense. The claimed inventions are intended to cover alternatives, modifications, and equivalents.

What is claimed is:

1. A method of inducing tear production in an individual, comprising:
   receiving a switch signal generated based on a manipulation of a control switch at a handheld device; and
   activating a motor in response to the switch signal to oscillate a member at an oscillation frequency, the member having an elongated configuration, and having a portion for placement outside the individual;
   wherein the oscillation frequency is sufficient to induce tear production when the portion of the member is applied towards a surface of a body portion of the individual; and
   wherein when the member is oscillated, a part of the portion of the member moves in and out of a housing of the handheld device.

2. The method of claim 1, wherein the member comprises a cantilevered beam having a free end, the portion being at the free end of the cantilevered beam.

3. The method of claim 2, wherein the motor is activated to cause the cantilevered beam to undergo bending action in a reciprocating manner.

4. The method of claim 1, further comprising varying a speed of the motor in response to an amount of force received at the portion of the member.

5. The method of claim 1, further comprising varying the oscillation frequency of the member in response to an amount of force received at the portion of the member.

6. The method of claim 1, wherein the portion of the member oscillates with a substantially fixed amplitude in air.

7. The method of claim 6, wherein the substantially fixed amplitude is anywhere between 0.25 mm and 1.5 mm.

8. The method of claim 1, wherein the portion of the member has a durometer that is anywhere between 40 A to 60 A.

9. The method of claim 1, wherein the portion of the member oscillates with a force that is anywhere from 1 N to 3 N.

10. The method of claim 1, wherein the oscillation frequency of the member is anywhere from 50 Hz to 300 Hz.

11. The method of claim 1, further comprising storing information related to a treatment duration, a treatment start time, a treatment end time, an applied force, a treatment frequency, or any combination of the foregoing.

12. The method of claim 1, wherein the motor oscillates the member at the oscillation frequency to stimulate a nasal nerve to induce the tear production.

13. The method of claim 1, wherein the body portion comprises a nose region.

14. The method of claim 1, wherein the body portion comprises an eyelid.

15. The method of claim 1, wherein the portion of the member is configured for placement over an infraorbital nerve.

16. The method of claim 1, wherein the portion of the member is configured for placement over an anterior ethmoidal nerve.

17. The method of claim 1, wherein the portion of the member is configured for placement over an external nasal nerve.

18. The method of claim 1, wherein the portion of the member is configured for placement over a meibomian gland.

19. The method of claim 1, wherein the portion has a convex exterior surface.

20. The method of claim 1, wherein the control switch comprises a button, wherein the switch signal is generated in response to a pressing of the button, and wherein the method further comprises de-activating the handheld device when the button is un-pressed.

21. The method of claim 1, wherein the portion of the member oscillates outside the housing of the handheld device.

22. The method of claim 1, wherein the housing with an opening, and the portion of the member oscillates within the opening.

23. The method of claim 1, further comprising wirelessly transmitting data to an external device.

24. The method of claim 23, wherein the data indicates a usage of the handheld device, a force of application by the handheld device, the oscillation frequency, or a combination of the foregoing.

25. A method of inducing tear production in an individual, comprising:

receiving a switch signal generated based on a manipulation of a control switch at a handheld device;

activating a motor in response to the switch signal to cause a member to undergo bending action in a reciprocating manner to oscillate a portion of the member at an oscillation frequency, wherein the portion is configured for placement outside the individual; and wirelessly transmitting data to an external device, the data indicating a usage of the handheld device, a force of application by the handheld device, the oscillation frequency, or a combination of the foregoing;

wherein the oscillation frequency is sufficient to induce tear production when the portion of the member is applied toward a surface of a body portion of the individual; and wherein as the member undergoes the bending action, a part of the member moves in and out of a housing of the handheld device.

26. The method of claim 25, wherein the part of the member is moveable into the housing in response to a force applied to the portion of the member.

27. The method of claim 25, wherein the member comprises a cantilevered beam having a free end, the portion being at the free end of the cantilevered beam.

28. The method of claim 25, wherein the member comprises a cantilevered beam having a fixed end, wherein the fixed end affects an oscillation property of the cantilevered beam.

29. The method of claim 25, further comprising varying a speed of the motor in response to an amount of force received at the portion of the member.

30. The method of claim 25, further comprising varying the oscillation frequency of the member in response to an amount of force received at the portion of the member.

31. The method of claim 25, further comprising receiving power from a power source located in the housing of the handheld device.

32. The method of claim 31, wherein the power source is a rechargeable battery.

33. The method of claim 25, wherein the portion of the member oscillates with a substantially fixed amplitude in air.

34. The method of claim 33, wherein the substantially fixed amplitude is anywhere between 0.25 mm and 1.5 mm.

35. The method of claim 25, wherein the portion of the member has a durometer that is anywhere between 40 A to 60 A.

36. The method of claim 25, wherein the portion of the member oscillates with a force that is anywhere from 1 N to 3 N.

37. The method of claim 25, wherein the oscillation frequency of the member is anywhere from 50 Hz to 300 Hz.

38. The method of claim 25, further comprising storing information related to a treatment duration, a treatment start time, a treatment end time, an applied force, a treatment frequency, or any combination of the foregoing.

39. The method of claim 25, wherein the motor oscillates the member at the oscillation frequency to stimulate a nasal nerve to induce the tear production.

40. The method of claim 25, wherein the body portion comprises a nose region.

41. The method of claim 25, wherein the body portion comprises an eyelid.

42. The method of claim 25, wherein the portion of the member is configured for placement over an infraorbital nerve.

43. The method of claim 25, wherein the portion of the member is configured for placement over an eyelid or directly on a sclera of an eye.

44. The method of claim 25, wherein the portion of the member is configured to be inserted intra-nasally.

45. The method of claim 25, wherein the portion of the member is configured for placement along a distribution of a sensory portion of an ophthalmic nerve division of a trigeminal nerve.

46. The method of claim 25, wherein the portion of the member is configured for placement over an anterior ethmoidal nerve.

47. The method of claim 25, wherein the portion of the member is configured for placement over a meibomian gland.

48. The method of claim 25, wherein the portion has a convex exterior surface.

49. The method of claim 25, wherein the portion has a thickness that is anywhere from 0.5 mm to 3 mm, and an edge forming an angle that is anywhere from 65 degrees to 125 degrees.

50. The method of claim 25, wherein the control switch comprises a button, wherein the switch signal is generated in response to a pressing of the button, and wherein the method further comprises de-activating the handheld device when the button is un-pressed.

51. The method of claim 25, wherein the portion of the member oscillates outside the housing of the handheld device.

52. The method of claim 25, wherein the housing has an opening, and the portion of the member oscillates within the opening.

* * * * *